(12) United States Patent
Stonehouse et al.

(10) Patent No.: US 12,247,208 B2
(45) Date of Patent: Mar. 11, 2025

(54) OPTIMIZATION OF BIOMASS-BASED FERMENTATIONS

(71) Applicant: Lallemand Hungary Liquidity Management LLC, Budapest (HU)

(72) Inventors: Emily Agnes Stonehouse, Etna, NH (US); John Evan Eck McBride, Lyme, NH (US); Kristen M. Deleault, Canaan, NH (US); Zachary Losordo, Norwich, VT (US); Mitchell Codd, Lebanon, NH (US)

(73) Assignee: DANSTAR FERMENT AG, Zug (CH)

( * ) Notice: Subject to any disclaimer, the term of this patent is extended or adjusted under 35 U.S.C. 154(b) by 0 days.

(21) Appl. No.: 16/616,306

(22) PCT Filed: May 23, 2018

(86) PCT No.: PCT/IB2018/053663
§ 371 (c)(1),
(2) Date: Nov. 22, 2019

(87) PCT Pub. No.: WO2018/215956
PCT Pub. Date: Nov. 29, 2018

(65) Prior Publication Data
US 2020/0224209 A1    Jul. 16, 2020

Related U.S. Application Data

(60) Provisional application No. 62/510,107, filed on May 23, 2017.

(51) Int. Cl.
*C12N 15/81* (2006.01)
*C12N 1/16* (2006.01)
*C12P 7/14* (2006.01)

(52) U.S. Cl.
CPC .............. *C12N 15/81* (2013.01); *C12N 1/16* (2013.01); *C12P 7/14* (2013.01)

(58) Field of Classification Search
CPC .......... C12N 15/81; C12N 1/16; C12N 15/52; C12P 7/14
See application file for complete search history.

(56) References Cited

U.S. PATENT DOCUMENTS

| | | | |
|---|---|---|---|
| 8,956,851 B2 | 2/2015 | Argyros et al. | |
| 2006/0257983 A1* | 11/2006 | Bro | C12P 1/02 435/254.2 |
| 2011/0189744 A1 | 8/2011 | Mcbride et al. | |
| 2011/0312054 A1 | 12/2011 | Brevnova et al. | |
| 2012/0003701 A1 | 1/2012 | Brevnova et al. | |
| 2016/0194669 A1* | 7/2016 | Argyros | C12N 1/32 435/254.2 |

FOREIGN PATENT DOCUMENTS

| | | |
|---|---|---|
| WO | 2009/138877 A2 | 11/2009 |
| WO | 2010/056805 A2 | 5/2010 |
| WO | 2010/060056 A2 | 5/2010 |
| WO | 2010/075529 A2 | 7/2010 |
| WO | 2011/153516 A2 | 12/2011 |
| WO | 2012/138942 A1 | 10/2012 |
| WO | 2015/023989 A1 | 2/2015 |
| WO | 2017/037614 A1 | 3/2017 |

OTHER PUBLICATIONS

Hubmann et al, Gpd1 and Gpd2 Fine-Tuning for Sustainable Reduction of Glycerol Formation in *Saccharomyces cerevisiae*. Applied and Environmental Microbiology, Sep. 2011, p. 5857-5867.*
Ferreira et al, A Member of the Sugar Transporter Family, Stl1p Is the Glycerol/H Symporter in *Saccharomyces cerevisiae*. Molecular Biology of the Cell vol. 16, 2068-2076, Apr. 2005.*
Kunze et al, Expression in yeast of a Bacillus alpha-amylase gene by the ADHI promoter . Journal of Biotechnology, 7 (1988) 33-48.*
Noda et al, The quantitative Pho8Delta60 assay of nonspecific autophagy. Methods Enzymol. 2008;451:33-42.*
Ferreira et al, Glucose repression over *Saccharomyces cerevisiae* glycerol/H+ symporter gene STL1 is overcome by high temperature. FEBS Letters 581 (2007) 1923-1927.*
Lu et al, Shuffling of Promoters for Multiple Genes to Optimize Xylose Fermentation in an Engineered *Saccharomyces cerevisiae* Strain. Applied and Environmental Microbiology, Oct. 2007, p. 6072-6077.*
Peng et al, Controlling heterologous gene expression in yeast cell factories on different carbon substrates and across the diauxic shift: a comparison of yeast promoter activities. Microb Cell Fact (2015) 14:91.*
Albertyn et al, GPDJ, Which Encodes Glycerol-3-Phosphate Dehydrogenase, Is Essential for Growth under Osmotic Stress in *Saccharomyces cerevisiae*, and Its Expression Is Regulated by the High-Osmolarity Glycerol Response Pathway. Molecular and Cellular Biology, Jun. 1994, vol. 14, No. 6, p. 4135-4144.*
Valadi et al, Distinct Intracellular Localization of Gpd1p and Gpd2p, the Two Yeast Isoforms of NAD-dependent Glycerol-3-phosphate Dehydrogenase, Explains Their Different Contributions to Redox-driven Glycerol Production. J Biol Chem vol. 279, No. 38, Issue of Sep. 17, pp. 39677-39685, 2004.*

(Continued)

*Primary Examiner* — Ganapathirama Raghu
(74) *Attorney, Agent, or Firm* — Seed IP Law Group LLP

(57) ABSTRACT

The present disclosure concerns recombinant microbial host cell having, in glycolytic conditions, increased glycerol importing activity glycerol as well as, in high osmotic conditions, a decreased NAD-dependent glycerol-3-phosphate dehydrogenase (GPD) activity. The recombinant microbial host cell is particularly useful for the fermentation of sugarcane- or molasses-based medium for the production of ethanol.

17 Claims, 17 Drawing Sheets

Specification includes a Sequence Listing.

(56) References Cited

OTHER PUBLICATIONS

Chellappan SP., HOG on the Promoter: Regulation of the Osmotic Stress Response. Science's STKE, 2001, vol. 93, pp. 1-4. (Year: 2001).*

Kaino et al., Proline as a Stress Protectant in the Yeast *Saccharomyces cerevisiae*: Effects of Trehalose and PRO1 Gene Expression on Stress Tolerance. Biosci. Biotechnol. Biochem., 2009, vol. 73(9): 2131-2135. (Year: 2009).*

Liu et al., Characterization of glyceraldehyde-3-phosphate dehydrogenase gene RtGPD1 and development of genetic transformation method by dominant selection in oleaginous yeast Rhodosporidium toruloides. Appl Microbiol Biotechnol., 2013, vol. 97: 719-729. (Year: 2013).*

Matsuzawa et al., The gld1+ gene encoding glycerol dehydrogenase is required for glycerol metabolism in Schizosaccharomyces pombe. Appl Microbiol Biotechnol., 2010, vol. 87: 715-727. (Year: 2010).*

Perez-Torrado et al. Alternative Glycerol Balance Strategies among *Saccharomyces* Species in Response to Winemaking Stress. Frontiers in Microbiol., 2016, vol. 7, Article 435, pp. 1-13. (Year: 2016).*

Ferreira et al., A Member of the Sugar Transporter Family, Stl1p Is the Glycerol/H+ Symporter in *Saccharomyces cerevisiae*. Mol. Biol. Cell., 2005, vol. 16: 2068-2076. (Year: 2005).*

Babazadeh et al., The yeast osmostress response is carbon source dependent. Nature, Scientific Reports, 2017, vol. 7: 990, pp. 1-11. (Year: 2017).*

Chen et al., Cloning and characterization of a NAD1-dependent glycerol-3-phosphate dehydrogenase gene from Candida glycerinogenes, an industrial glycerol producer. FEMS Yeast Res., 2008, vol. 8: 725-734. (Year: 2008).*

Hubmann et al., Gpd1 and Gpd2 Fine-Tuning for Sustainable Reduction of Glycerol Formation in *Saccharomyces cerevisiae*. Appl. Environ. Microbiol., 2011, vol. 77(17): 5857-5867. (Year: 2011).*

Neves et al., Yeast orthologues associated with glycerol transport and metabolism. FEMS Yeast Res., 2004, vol. 5: 51-62. (Year: 2004).*

Noti et al. Short-term response of different *Saccharomyces cerevisiae* strains to hyperosmotic stress caused by inoculation in grape must: RT-qPCR study and metabolite analysis. Food Microbiol., 2015, vol. 52: 49-58. (Year: 2015).*

Argueso et al., "Genome structure of a *Saccharomyces cerevisiae* strain widely used in bioethanol production," *Genome Res.* 19:2258-2270, 2009.

Cao et al., "Overexpression of GLT1 in fps1ΔgpdΔ mutant for optimum ethanol formation by *Saccharomyces cerevisiae*," *Biomolecular Engineering* 24:638-642, 2007.

Kong et al., "Improved production of ethanol by deleting FPS1 and over-expressing GLT1 in *Saccharomyces cerevisiae*," *Biotechnol Lett* 28:2033-2038, 2006.

Kong et al., Over-expressing GLT1 in a gpd2Δ mutant of *Saccharomyces cerevisiae* to improve ethanol production, *Appl Microbiol Biotechnol* 75:1361-1366, 2007.

Pagliardini et al., "Quantitative evaluation of yeast's requirement for glycerol formation in very high ethanol performance fed-batch process," *Microbial Cell Factories* 9:36, 2010, 13 pages.

Wang et al., "Increasing ethanol titer and yield in a gpd1Δ gpd2Δ strain by simultaneous overexpression of GLT1 and STL1 in *Saccharomyces cerevisiae*," *Biotechnol Lett*, 2013, 6 pages.

Zhang et al., "Effect of FPS1 deletion on the fermentation properties of *Saccharomyces cerevisiae*," *Letters in Applied Microbiology* 44:212-217, 2007.

Ansell et al., "The two isoenzymes for yeast $NAD^+$-dependent glycerol 3-phosphate dehydrogenase encoded by GPD1 and GPD2 have distinct roles in osmoadaptation and redox regulation," *The EMBO Journal* 16(9):2179-2187, 1997.

Jung et al., "Dynamic Changes in the Subcellular Distribution of Gpd1p in Response to Cell Stress," *The Journal of Biological Chemistry* 285(9):6739-6749, Feb. 2010.

Kayingo et al., A permease encoded by STL1 is required for active glycerol uptake by *Candida albicans*, *Microbiology* 155:1547-1557, 2009.

Klein et al., "Glycerol metabolism and transport in yeast and fungi: established knowledge and ambiguities," *Environmental Microbiology* 19(3):878-893, 2017.

Lee et al., "Reciprocal Phosphorylation of Yeast Glycerol-3-Phosphate Dehydrogenases in Adaptation to Distinct Types of Stress," *Molecular and Cellular Biology* 32(22):4705-4717, Nov. 2012.

Valadi et al., "Distinct Intracellular Localization of Gpd1p and Gpd2p, the Two Yeast Isoforms of $NAD^+$-dependent Glycerol-3-phosphate Dehydrogenase, Explains Their Different Contributions to Redox-driven Glycerol Production," *The Journal of Biological Chemistry* 279(38):39677-39685, Sep. 2004.

* cited by examiner

OPTIMIZATION OF BIOMASS-BASED FERMENTATIONS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_409USPC_SEQUENCE_LISTING.txt. The text file is 56.4 KB, was created on Nov. 21, 2019, and is being submitted electronically via EFS-Web.

TECHNOLOGICAL FIELD

The present disclosure concerns recombinant microbial host cell as well as associated method for the fermentation of any type of biomass, including sugarcane, molasses or products derived therefrom (juice, must, etc.), into a fermented product, such as ethanol.

BACKGROUND

The conversion of biomass into ethanol is routinely completed through the use of microbial (e.g., yeast) fermentation. The conversion of sugarcane derived sugars like juice and/or molasses is unique in the sense that it usually involves the recycling and acid washing of the fermentation microorganisms. Fermenting microorganisms are often pitched either individually or together with other strains to start the crushing season, and then recycled (using acid washing) for the entire crushing season (~200 days).

*Saccharomyces cerevisiae* is the main organism used throughout the world for fuel ethanol production. The fuel ethanol industry converts sucrose from sugarcane into ethanol with yields up to 92% of theoretical conversion. Since more than half of the final cost of sugarcane ethanol is from the cost of sugarcane, any increase in ethanol yields from the cane would be a significant economic gain for manufacturers. For example, even a 1% increase in ethanol yield would mean >250 million extra liters of ethanol produced annually from the same amount of cane being crushed.

It would thus be desirable to be provided with a recombinant microbial host cell for the fermentation of sugarcane and/or molasses capable of providing an increased ethanol yield, especially under stressful conditions.

BRIEF SUMMARY

The present disclosure concerns recombinant microbial host cell having increased glycerol importing activity as well as decreased NAD-dependent glycerol-3-phosphate dehydrogenase (GPD) activity. The increased glycerol importing activity can be observed during glycolytic conditions. The decreased GPD activity can be observed in high osmotic conditions. The recombinant microbial host cell is particularly useful for the fermentation of carbohydrates, such as sugarcane- or molasses-based medium, for the production of ethanol.

In a first aspect, the present disclosure provides a recombinant microbial host cell: a) having a first genetic modification for increasing, optionally in glycolytic conditions, the activity of a first native and/or heterologous protein that functions to import glycerol into the recombinant host cell; b) having a second genetic modification for decreasing, optionally in high osmotic conditions, the activity of a NAD-dependent glycerol-3-phosphate dehydrogenase (GPD) protein; and c) expressing at least one native or heterologous GPD protein. In an embodiment, the at least one native or heterologous GPD protein is a GPD2 protein. In still another embodiment, the GPD2 protein is a native GPD2 protein expressed from a native GPD2 gene under the control of a native GPD2 promoter. In an embodiment, the first genetic modification comprises introducing a first heterologous nucleic acid molecule in the recombinant microbial host cell and wherein the first heterologous nucleic acid molecules comprises a first polynucleotide encoding the first heterologous protein that functions to import glycerol. In yet another embodiment, the first genetic modification comprises introducing a first heterologous nucleic acid molecule in the microbial host cell, wherein the first heterologous nucleic acid comprises and a second polynucleotide encoding a glycolytic promoter capable of being operably linked to a gene encoding the first native heterologous protein that functions to import glycerol. In still another embodiment, the first genetic modification comprises introducing a first heterologous nucleic acid molecule in the recombinant microbial host cell and wherein the first heterologous nucleic acid molecules comprises a first polynucleotide encoding the first heterologous protein that functions to import glycerol a second polynucleotide encoding a glycolytic promoter operably linked to the first polynucleotide. In yet another embodiment, the glycolytic promoter comprises a promoter from a ADH1 gene, a PGI1 gene, a PFK1 gene, a PFK2 gene, a FBA1 gene, a TPI1 gene, a TDH1 gene, a TDH2 gene, a TDH3 gene, a PGK1 gene, a GPM1 gene, a ENO1 gene, a ENO2 gene, a PYK2 gene and/or a CDC19 gene. In a further embodiment, the glycolytic promoter is a constitutive promoter. In still a further embodiment, the recombinant microbial host cell has at least 2, 4, 6 or 8 copies of the first heterologous nucleic acid molecule. In yet another embodiment, the first native and/or heterologous protein that functions to import glycerol is a glycerol proton symporter, such as, for example, a STL1 protein, a variant of a STL1 protein or a fragment of a STL1 protein. The STL1 protein can be derived, for example, from *Saccharomyces cerevisiae*. In another embodiment, the second genetic modification is for reducing the expression of a native glycerol-3-phosphate dehydrogenase-1 (GPD1) protein. In an embodiment, the second genetic modification comprises inhibiting the expression of the native glycerol-3-phosphate dehydrogenase-1 (GPD1) protein. In another embodiment, the second genetic modification comprises deleting at least one nucleotide of the gene encoding the native GPD1 protein. In still a further embodiment, the second genetic modification comprises introducing a second heterologous nucleic acid molecule in the recombinant microbial host cell and wherein the second heterologous nucleic acid molecules comprises a third polynucleotide encoding an heterologous GPD2 protein. In an embodiment, the second genetic modification comprises introducing a second heterologous nucleic acid molecule in the recombinant microbial host cell, wherein the second heterologous nucleic acid molecule comprises a fourth polynucleotide encoding an osmotic promoter capable of being operatively linked to a gene encoding an heterologous GPD2 protein. In still a further embodiment, the second genetic modification comprises introducing a second heterologous nucleic acid molecule in the recombinant microbial host cell and wherein the second heterologous nucleic acid molecule comprises a fifth polynucleotide encoding an heterologous GPD2 protein and a sixth polynucleotide encoding an osmotic promoter operably liked to the fifth polynucleotide. In another embodiment, the osmotic promoter is from a promoter from a GPD1 gene, a DAK1 gene and/or a TPS2 gene. In embodiments, the recombinant microbial host cell can be a recombinant yeast host cell. The recombinant yeast host cell can be from the genus *Saccharomyces* sp., for example, from the species *Saccharomyces cerevisiae*.

In a second aspect, the present disclosure provides a process for making a fermentation product, the process comprising contacting (i) a first fermentation medium comprising a carbohydrate with (ii) the recombinant microbial host cell described herein to obtain a first fermented medium under conditions to promote the production of the fermentation product. In an embodiment, the fermentation medium comprises sugarcane, a sugarcane derivative, molasses and/or a molasses derivative. In still another embodiment, the fermentation product is ethanol. In still another embodiment, the process further comprises at least one fermentation cycle comprising acid washing the recombinant microbial host cell present in the fermented medium to obtain an acid washed recombinant microbial host cell and contacting the acid washed recombinant microbial host cell with a second fermentation medium comprising a carbohydrate to obtain a second fermented medium under conditions to promote the production of the fermentation product. In still another embodiment, the process further comprises at least two or more fermentation cycles. In another embodiment, the process further comprises admixing the recombinant microbial host cell with a further microorganism, such as, for example, a non-genetically modified microorganism.

In a third aspect, the present disclosure provides a fermentation medium comprising the recombinant microbial host cell described herein. The fermentation medium may comprise, for example, a further microorganisms (such as, for example, a non-genetically modified microorganisms or a contaminating microorganism). The fermentation medium may also comprise sugarcane (or a sugarcane derivative) and/or molasses (or a molasses derivative). In some embodiments, the fermentation medium may also comprise ethanol and/or glycerol.

BRIEF DESCRIPTION OF THE DRAWINGS

Having thus generally described the nature of the invention, reference will now be made to the accompanying drawings, showing by way of illustration, a preferred embodiment thereof, and in which:

(FIG. 6A) Maximal growth rate ("MaxV" on a logarithmic scale, left axis and black bars) and the time to reach maximal growth rate ("time at MaxV" as measured in hours on a logarithmic scale, right axis and white squares) are provided for various strains grown on YP medium supplemented with sucrose. (FIG. 6B) Ethanol yield (provided as a percentage increase when compared to strain M7101) for strains M10648 (♦), M10686 (□) and M10682 (△) over 5 fermentation cycles (F1 to F5). (FIG. 6C) Percentage of decrease of glycerol production (when compared to strain M7101) for strains M10648 (darker grey bars), M10686 (white bars) and M10682 (lighter gray bars) for cycles F3 and F5. Glycerol production was not determined (N.D.) during cycles F1, F2 and F4. (FIG. 6D) $CO_2$ off-gas rates (provided as mL/min) over time (provided in hours) for strains M7101 (dark solid line), M10648 (dark broken line), M10686 (light solid line) and M10682 (light dashed line) at the third cycle of the fermentation. (FIG. 6E) $CO_2$ off-gas rates (provided as mL/min) over time (provided in hours) for strains M7101 (dark solid line), M10648 (dark broken line), M10686 (light solid line) and M10682 (light dashed line) at the fifth cycle of the fermentation. See Example II for a description of the various strains used.

or the change in ethanol production (right axis and circles). N=9. See Example III for a description of the various strains used.

Figure 9:
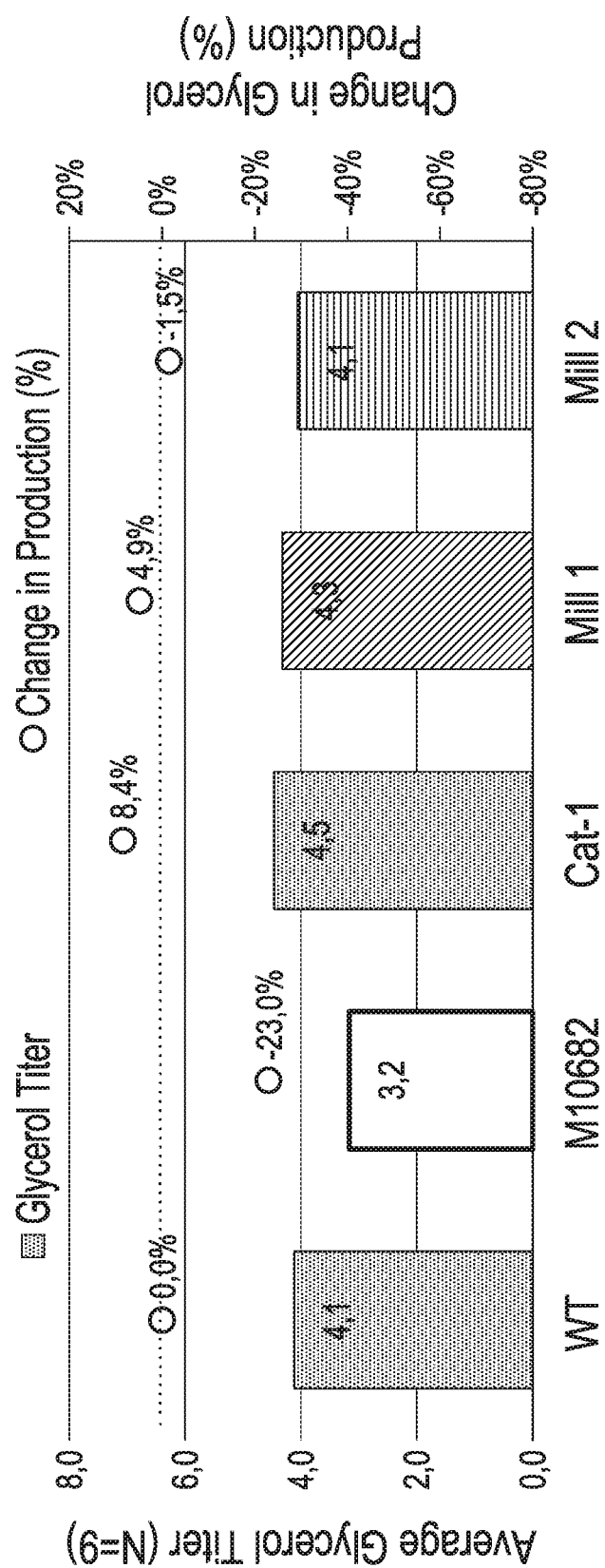

FIG. 9 compares glycerol production from sugarcane must fermentations using a recombinant yeast host cell (M10682) and yeast strains from the Brazilian ethanol industry (Cat-1, Mill 1 and Mill 2). Results are provided as the average glycerol titer (measured as g/L, left axis and bars) or the change in glycerol production (right axis and circles). N=9. See Example III for a description of the various strains used.

Figure 10:
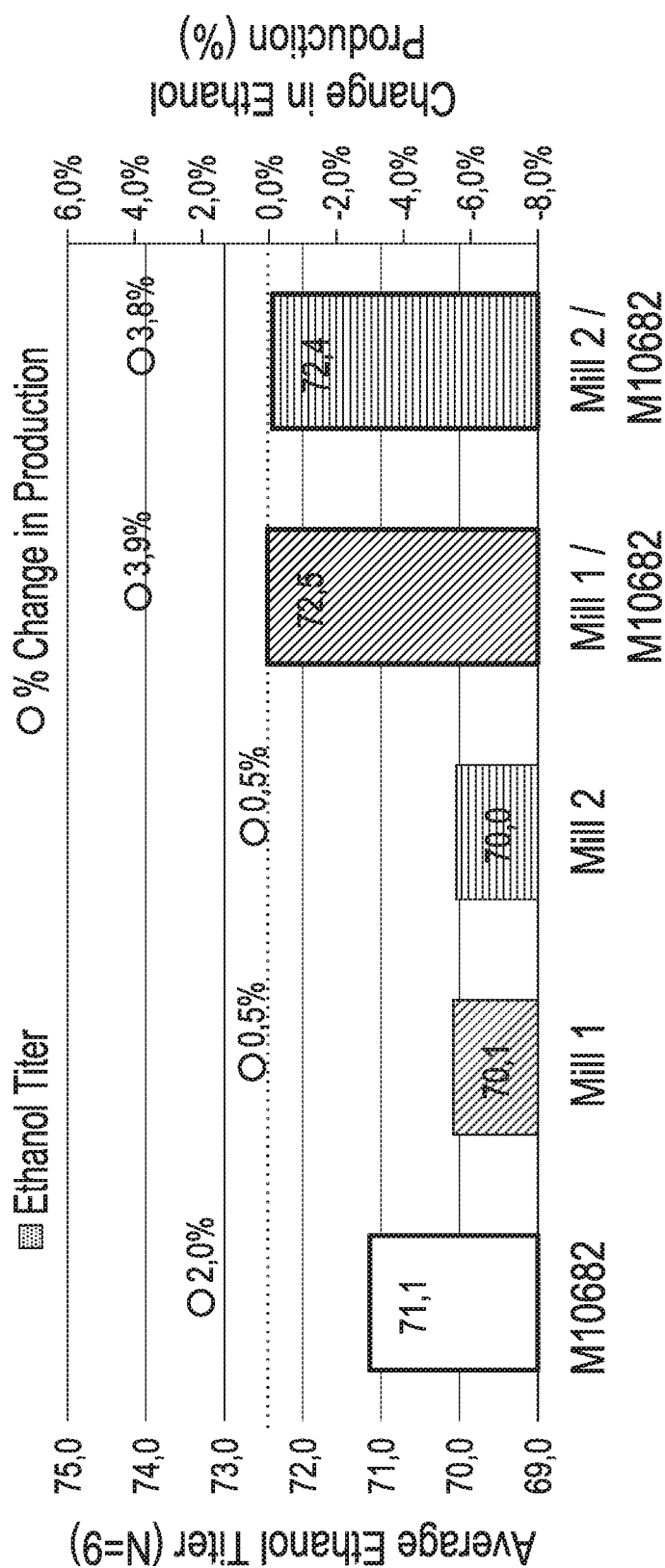

FIG. 10 compares ethanol production from sugarcane must fermentations using a recombinant yeast host cell (M10682) alone or in combination with yeast strains from the Brazilian ethanol industry (Mill 1 or Mill 2). Results are provided as the average ethanol titer (measured as g/L, left axis and bars) or the change in ethanol production (right axis and circles). N=9. See Example III for a description of the various strains used.

Figure 11:
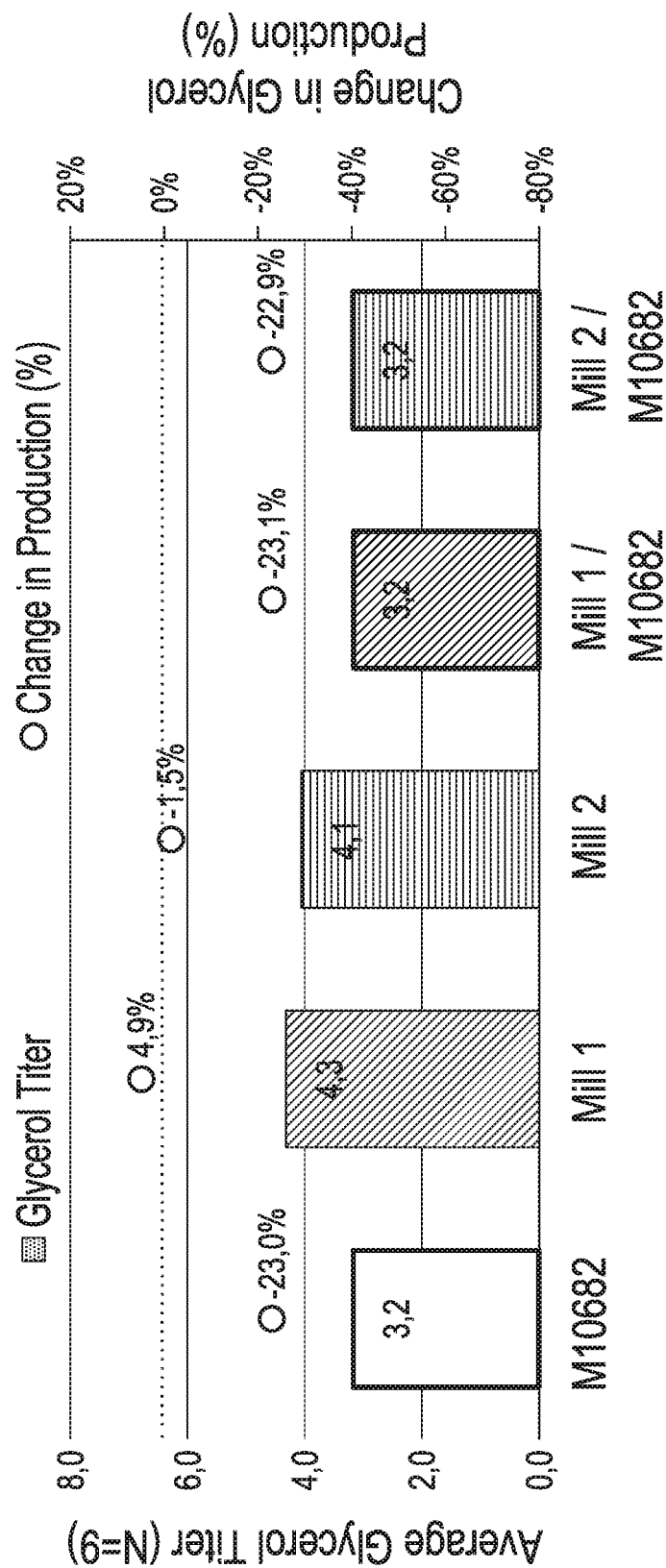

FIG. 11 compares glycerol production from sugarcane must fermentations using a recombinant yeast host cell (M10682) alone or in combination with yeast strains from the Brazilian ethanol industry (Mill 1 or Mill 2). Results are provided as the average glycerol titer (measured as g/L, left axis and bars) or the change in glycerol production (right axis and circles). N=9. See Example III for a description of the various strains used.

Figure 12:
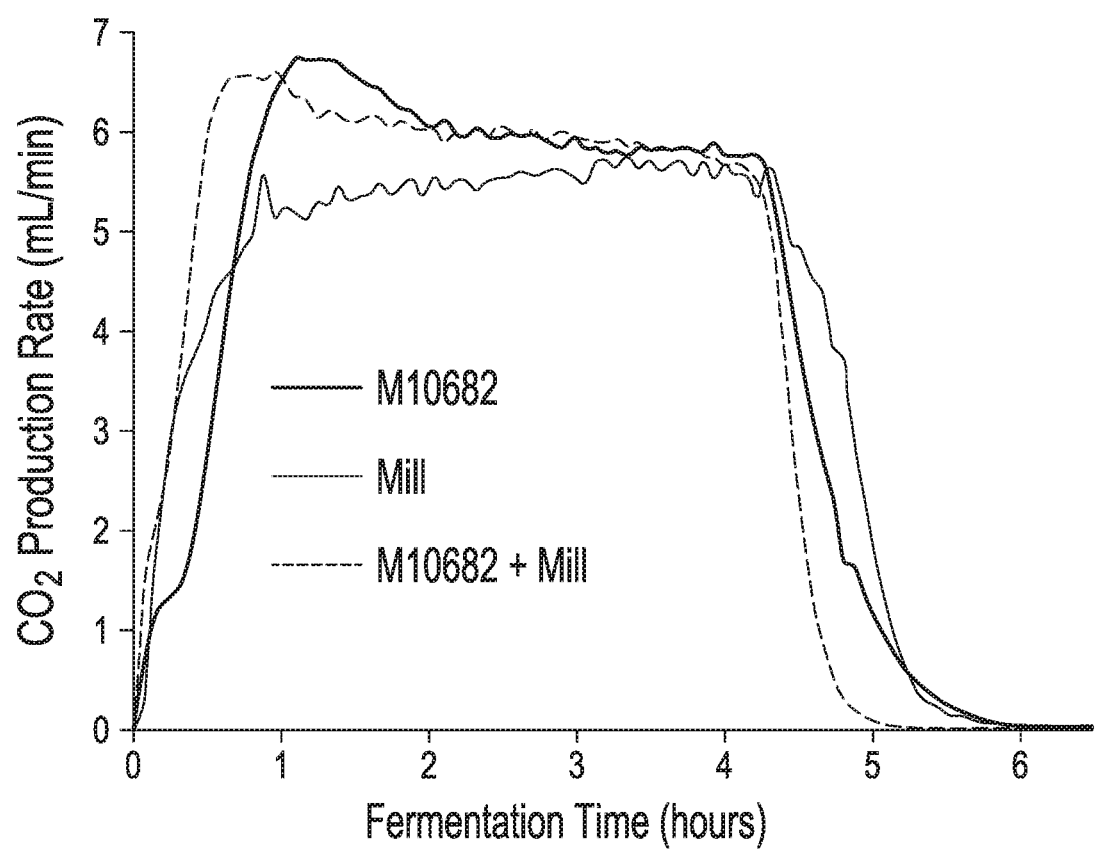

FIG. 12 compares the $CO_2$ off-gas rates for strains M10682 alone or in combination with yeasts from the Brazilian ethanol industry ("Mill"). Results are presented as $CO_2$ flow (mL/min) in function of time (hours) for strain M10682 (dark grey solid line), yeasts from the Brazilian ethanol industry (light grey solid line) or a combination of both (dark grey dashed line). See Example III for a description of the various strains used.

DETAILED DESCRIPTION

During microbial metabolism (and especially yeast metabolism) a major by-product of fermentation is glycerol. Glycerol is produced in microorganisms, such as yeasts, in response to a redox or osmotic stress. The glycerol produced is then exported from the cell where it is considered waste. While the production of glycerol is important to protect microorganisms from various stressors, it also tends to decrease ethanol yields, especially when the microorganisms are growing or encountering osmotic stress.

In yeasts, glycerol is a required metabolic end-product of ethanol fermentation allowing the yeast to balance its redox state and regenerate $NAD^+$ used as a cofactor during glycolysis. During anaerobic growth on carbohydrates, production of ethanol and carbon dioxide is redox neutral, while the reactions that create cell biomass and associated carbon dioxide are more oxidized relative to carbohydrates. The production of glycerol, which is more reduced relative to carbohydrates, functions as an electron sink to off-set cell biomass formation, so that overall redox neutrality is conserved. This is essential from a theoretical consideration of conservation of mass, and in practice strains unable to produce glycerol are unable to grow under anaerobic conditions.

As glycerol is a byproduct with low value, it can be an undesirable by-product of fermentation. There is a strong commercial incentive to reduce glycerol as a by-product during the production of fuels and chemicals, as reduction typically results in an increased yield of the desired compound.

Several strategies are available in the art for the conversion of glycerol to higher value products through biochemical or other means. In addition, various strategies have been employed to reduce glycerol production, which may lead to an improvement of overall sugar yield to ethanol or other desired end-products of metabolism. Through engineering of alternate pathways, with the simultaneous reduction or deletion of the glycerol pathway, alternate or replacement electron acceptors for the regeneration of $NAD^+$ can be used during yeast metabolism. Examples of such alternate or replacement electron acceptors include molecules such as formate or hydrogen.

The elimination of glycerol synthesis genes has been demonstrated but removal of this pathway completely blocked anaerobic growth of the yeast, preventing useful application during an industrial process. Other methods to bypass glycerol formation require the co-utilization of additional carbon sources, such as xylose or acetate, to serve as electron acceptors. The engineering of a pyruvate formate lyase from *E. coli*, which is capable of converting pyruvate to formate, was performed previously to increase formate production. As shown in WO 2012/138942, the use of a formate pathway as an alternate electron acceptor allows for glycerol formation to be bypassed and ethanol yield to be increased.

In addition to its known role during anaerobic growth, glycerol is also synthesized by *S. cerevisiae* in response to osmotic stress. The formation of glycerol is mediated in part by the activity of two glycerol-3-phosphate dehydrogenases: GPD1 and GPD2. Glycerol formed in response to osmotic stress is mediated primarily through the action of GPD1, whereas glycerol formed as an electron sink for excess electrons generated during production of biomass during anaerobic growth is mediated primarily through the action of GPD2. Glycerol is exported from the yeast cell through an aquaporin channel known as FPS1. This channel is closed in response to osmotic stress in order to reduce glycerol efflux from the cell, thereby enabling accumulation of higher levels of intracellular glycerol. In addition, yeasts can increase intracellular glycerol levels through uptake of glycerol from the extracellular environment through the action of another glycerol transporter known as STL1. The expression of STL1, however, is limited by transcriptional repression of the gene in the presence of glucose. As shown in WO 2015/023989, the overexpression of STL1, in combination with other heterologous proteins, can be used to improve ethanol yield.

Anaerobic glycerol production in response to osmotic stress, however, cannot occur in the absence of an accompanying oxidation reaction. Under anaerobic conditions, yeasts in stationary phase need to generate reducing power to make glycerol in response to osmotic stress. The net result is that, in addition to making glycerol in response to osmotic stress, the organism must also make an oxidized end product which further reduces the yield of the desired product.

It has been shown that an increase in acetate, pyruvate and succinate production accompanies anaerobic glycerol production in response to osmotic stress. The concentration of these metabolites, however, was only sufficient to produce approximately half of the necessary NADH needed to balance the increase in glycerol. Further, elevated levels of pyruvate, succinate, acetaldehyde, acetoin and 2,3-butanediol were observed in wine strains engineered to produce more glycerol. The production of these compounds was reflected in the redox and carbon balance although the relationship was not elaborated upon.

The present disclosure provides a recombinant microbial host cell producing less glycerol and more ethanol, especially when the host cell is placed in glycolytic conditions. The recombinant microbial host cell has at least two genetic modifications. The recombinant microbial yeast host cell has a first genetic modification allowing, preferably in glycolytic conditions, an increase in the activity of a (native and/or heterologous) protein that functions to import glycerol. The recombinant microbial host cell also has a second genetic modification allowing, preferably in high osmotic conditions, a reduction in the activity of a (native and/or heterologous) NAD-dependent glycerol-3-phosphate dehydrogenase (GPD) protein. Importantly, the recombinant yeast host cell of the present disclosure exhibits both glycerol import and NAD-dependent GPD activity, preferably in glycolytic conditions as well as in regular and low osmotic conditions.

i) Definitions

Unless defined otherwise, all technical and scientific terms used herein have the same meaning as commonly understood by one of ordinary skill in the art to which this invention belongs. Also, unless otherwise required by context, singular terms shall include pluralities and plural terms shall include the singular. All publications, patents and other references mentioned herein are incorporated by reference in their entireties for all purposes.

The term "heterologous" when used in reference to a polynucleotide, a gene, a polypeptide, or an enzyme refers to a nucleic acid, a polynucleotide, a gene, a protein, a polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes. The term "heterologous" when used in reference to a nucleic acid molecule (such as a promoter, a terminator or a coding sequence) or a protein refers to a nucleic acid molecule or a protein that is not natively found in the recombinant host cell. For example, a heterologous element could be derived from a different strain of host cell, or from an organism of a different taxonomic group (e.g., different kingdom, phylum, class, order, family genus, or species, or any subgroup within one of these classifications). A heterologous element may be derived from any source, e.g., eukaryotes, prokaryotes, viruses, or synthetic polynucleotide fragments.

The heterologous nucleic acid molecules or polynucleotides present in the recombinant host cell can be integrated in the host cell's genome. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies (e.g., 2, 3, 4, 5, 6, 7, 8, 9, 10, 11 or even more copies) in the microbial host cell's genome (at the same or different loci). Alternatively, the heterologous nucleic acid molecule can be independently replicating from the yeast's genome. In such embodiment, the nucleic acid molecule can be stable and self-replicating.

In some embodiments, heterologous nucleic acid molecules which can be introduced into the recombinant microbial host cells are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized heterologous nucleic acid molecule described herein corresponds to between about 0.8 and 1.0, between about 0.8 and 0.9, or about 1.0.

The heterologous nucleic acid molecule can be introduced in the recombinant microbial host cell using a vector. A "vector," e.g., a "plasmid", "cosmid" or "artificial chromosome" (such as, for example, a yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

In the context of the present disclosure, a "gene ortholog" is understood to be a gene in a different species that evolved from a common ancestral gene by speciation. It is understood that the protein encoded by a gene ortholog retains the same function as the protein encoded by the original gene.

The heterologous nucleic acid molecules/polynucleotides described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The term "promoter" is intended to include a polynucleotide that can transcriptionally control a gene-of-interest that it does not transcriptionally control in nature. In certain embodiments, the transcriptional control of a promoter results in an increase in expression of the gene-of-interest under certain circumstances. In certain embodiments, a promoter is placed 5' to the gene-of-interest. A promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of biomass to, e.g., ethanol.

The heterologous proteins or polypeptides can be a variant of a known/native protein or polypeptide. A variant comprises at least one amino acid difference when compared to the amino acid sequence of the native protein or polypeptide. As used herein, a variant refers to alterations in the amino acid sequence that do not adversely affect the biological functions of the protein or polypeptide. A substitution, insertion or deletion is said to adversely affect the protein when the altered sequence prevents or disrupts a biological function associated with the native protein or polypeptide. For example, the overall charge, structure or hydrophobic-hydrophilic properties of the protein can be altered without adversely affecting a biological activity. Accordingly, the amino acid sequence can be altered, for example, to render the peptide more hydrophobic or hydrophilic, without adversely affecting the biological activities of the food and/or feed enzyme. The protein or polypeptides variants have at least 50%, 55%, 60%, 65%, 70%, 75%, 80%, 85%, 90%, 95%, 96%, 97%, 98% or 99% identity to the native proteins and polypeptides described herein. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant proteins or polypeptides described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide. A "variant" of the food and/or feed enzyme can be a conservative variant or an allelic variant.

The heterologous proteins or polypeptides can be a fragment of a known/native/variant protein or polypeptide. A fragment comprises at least one less amino acid residue when compared to the amino acid sequence of the known/native/variant protein or polypeptide and still possess the biological activity of the native protein or polypeptide. In some embodiments, protein or polypeptide "fragments" have at least at least 100, 200, 300, 400, 500, 600, 700 or more consecutive amino acids of the known/native/variant protein or polypeptide. In some embodiments, fragments have at least 50%, 55%, 60%, 65%, 70%, 75%, 80%, 85%, 90%, 95%, 96%, 97%, 98% or 99% identity to the known/native/variant proteins and polypeptides described herein. In some embodiments, fragments can be employed for producing the corresponding full-length protein or polypeptide by peptide synthesis. Therefore, the fragments can be employed as intermediates for producing the full-length proteins.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

In the context of the present disclosure, the recombinant host cell is a microorganism and includes, without limitations, bacteria, yeasts, fungi, plant and mammalian cells. In an embodiment, the recombinant microbial host cell is a yeast and, in some additional embodiments, the yeast can be used in the production of biofuels. Suitable yeast host cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces, Torula* or *Yarrowia*. Suitable yeast species can include, for example, *S. cerevisiae, S. bulderi, S. barnetti, S. exiguus, S. uvarum, S. diastaticus, C. utilis, K. lactis, K. marxianus* or *K. fragilis*. In some embodiments, the yeast is selected from the group consisting of *Saccharomyces cerevisiae, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In some embodiment, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus Thraustochytrium or Schizochytrium). In an embodiment, the recombinant yeast host cell is from the genus *Saccharomyces* and, in some embodiments, from the species *Saccharomyces cerevisiae*.

ii) Glycerol Import Activity

In the context of the present disclosure, the recombinant microbial host cell has at least one first genetic modification allowing it to increase the (biological) activity of a protein which functions to import glycerol (e.g., actively transport glycerol inside the cell) and/or decrease the (biological) activity of a protein which functions to export glycerol (e.g., actively transport glycerol inside the cell). Still in the context of the present disclosure, the activity of the protein functioning to import/export glycerol in the recombinant microbial host cell is optionally modulated in glycolytic conditions. As shown in the Examples below, increasing the import of glycerol during glycolytic conditions is advantageous over modifying alternate pathways of glycerol production, because, amongst other things, it increased ethanol yield, decreases glycerol production while maintaining adequate robustness (growth rates, kinetics, at high temperatures or in the presence of bacterial contamination).

In an embodiment, the recombinant microbial host cells has at least one first genetic modification allowing it to increase the (biological) activity of a protein which functions to import glycerol (e.g., actively transport glycerol inside the cell). In some embodiments, the activity of the protein functioning to import glycerol in the recombinant microbial host cell is increased in glycolytic conditions. The STL1 protein is an exemplary protein which functions to import glycerol.

In another embodiment, the recombinant microbial host cells has at least one first genetic modification allowing it to decrease the (biological) activity of a protein which functions to export glycerol (e.g., actively transport glycerol outside the cell). In some embodiments, the activity of the protein functioning to export glycerol in the recombinant microbial host cell is decreased in glycolytic conditions. The FPS1 protein is an exemplary protein which functions to export glycerol. The FPS1 protein a channel protein located in the plasma membrane that controls the accumulation and release of glycerol in yeast osmoregulation. Null mutants of this strain accumulate large amounts of intracellular glycerol, grow much slower than wild-type, and consume the sugar substrate at a slower rate. As such, the first genetic modification can include reducing or deleting the expression of the gene encoding the FPS1 protein during glycolytic conditions.

As used in the context of the present disclosure, the expression "glycolytic conditions" refers to the presence of sufficient glucose in the environment surrounding the recombinant microbial host cell to trigger the uptake of that glucose by the cell. The increase in glycerol importing activity can be observed with respect to the same recombinant microbial cell that is not undergoing glycolysis (for example during the propagation phase of the recombinant microbial cell or in the absence of glucose). This increase can also be observed with respect to a corresponding recombinant microbial host cell lacking the first genetic modification. In the context of the present disclosure, it is not necessary that the increase in activity of the protein functioning to import glycerol be limited to circumstances in which the recombinant microbial host cell be in glycolytic conditions but it is important that the increase in activity be observed when the recombinant microbial host cell is placed in glycolytic conditions.

The recombinant microbial host cells of the present disclosure include a first genetic modification to introduce (one or more copies of) of an heterologous nucleic acid molecule encoding an heterologous protein functioning to import glycerol and/or to replace the promoter of the gene encoding the native protein functioning to import glycerol with a glycolytic promoter.

In order to increase the activity of the protein functioning to import glycerol, it is possible to include, in the recombinant microbial host cell, one or more copies of an heterologous nucleic acid molecule encoding the protein functioning to import glycerol. As indicated above, in the context of the present disclosure, a nucleic acid molecule is considered "heterologous", even though it is derived from the microbial host cell, when it is reintroduced in one or more loci which are native for this nucleic acid molecule. For example, the recombinant microbial host cell can have one, two, three, four, five, six, seven, eight, nine, ten, eleven, twelve or more copies of the heterologous nucleic acid molecule encoding the protein functioning to import glycerol. In an embodiment, the recombinant microbial host cell comprises between four and eight copies of the heterologous nucleic acid molecule encoding the protein functioning to import glycerol. In an embodiment, the recombinant microbial host cell comprises at least (and in some additional embodiments no more than) two copies of the heterologous nucleic acid molecule encoding the protein functioning to import glycerol. In another embodiment, the recombinant microbial host cell comprises at least (and in some additional embodiments no more than) three copies of the heterologous nucleic acid molecule encoding the protein functioning to import glycerol. In yet another embodiment, the recombinant microbial host cell comprises at least (and in some additional embodiments no more than) four copies of the heterologous nucleic acid molecule encoding the protein functioning to import glycerol. In still another embodiment, the recombinant microbial host cell comprises at least (and in some additional embodiments no more than) five copies of the heterologous nucleic acid molecule encoding the protein functioning to import glycerol. In a further embodiment, the recombinant microbial host cell comprises at least (and in some additional embodiments no more than) six copies of the heterologous nucleic acid molecule encoding the protein functioning to import glycerol. In yet a further embodiment, the recombinant microbial host cell comprises at least (and in some additional embodiments no more than) seven copies of the heterologous nucleic acid molecule encoding the protein functioning to import glycerol. In still a further embodiment, the recombinant microbial host cell comprises at least (and in some additional embodiments no more than) eight copies of the heterologous nucleic acid molecule encoding the protein functioning to import glycerol. The heterologous nucleic acid molecule can be independently replicating or integrated in the recombinant microbial host cell. When the heterologous nucleic acid molecule is integrated in the recombinant microbial host cell, it is preferably positioned at neutral integration site. When more than one copy of the heterologous nucleic acid molecule encoding the protein functioning to import glycerol is introduced in the recombinant microbial host cell, each of the copy can be integrated at one or more (the same or different) integration sites.

In order to achieve the expression (or, in some embodiments, the overexpression) of the activity of the protein functioning to import glycerol in glycolytic conditions, it may be necessary to include a glycolytic promoter to control the expression of the gene encoding the protein functioning to import glycerol. In the context of the present disclosure, a "glycolytic promoter" is a promoter (or a combination of promoters) allowing the expression (or, in some embodiments, the overexpression) of a gene operatively associated thereto when the recombinant microbial cell is in placed in glycolytic conditions. The glycolytic promoter can be included in the recombinant microbial host cell either to control the expression of a native and/or an heterologous gene encoding the protein functioning to import glycerol. The glycolytic promoter can be a constitutive promoter or a glucose-inducible promoter. Glycolytic promoters exclude glucose-repressible promoters. Glucose-inducible promoters are usually associated with genes encoding enzymes in the glycolytic pathway and promoters controlling the expression of enzymes which are upregulated in the glycolytic pathway can be used in the recombinant microbial host cell of the present disclosure. Enzymes of the glycolytic pathway whose expression is upregulated in the presence of glucose include, but are not limited to, those encoded by an alcohol dehydrogenase gene, a glucose-6-phosphate isomerase gene, a phosphofructokinase gene, an aldolase gene, a triosephosphate isomerase gene, a glyceraldehyde-3-phosphate dehydrogenase gene, a 3-phosphoglycerate kinase gene, a phosphoglycerate mutase, an enolase and a pyruvate kinase gene. As such, in the context of the present disclosure, the glycolytic promoter can be a promoter (or a combination of promoters) from an alcohol dehydrogenase gene, a glucose-6-phosphate isomerase gene, a phosphofructokinase gene, an aldolase gene, a triosephosphate isomerase gene, a glyceraldehyde-3-phosphate dehydrogenase gene, a 3-phosphoglycerate kinase gene, a phosphoglycerate mutase, an enolase and/or a pyruvate kinase gene.

In *Saccharomyces cerevisiae*, enzymes of the glycolytic pathway whose expression is upregulated in the presence of glucose include, but are not limited to, those encoded by a ADH1 gene, a PGI1 gene, a PFK1 gene, a PFK2 gene, a FBA1 gene, a TPI1 gene, a TDH1 gene, a TDH2 gene, a TDH3 gene, a PGK1 gene, a GPM1 gene, a ENO1 gene, a ENO2 gene, a PYK2 gene and a CDC19 gene. As such, in the context of the present disclosure, the glycolytic promoter can be a promoter (or a combination of promoters) from a ADH1 gene (referred to as the ADH1 promoter or adh1p), a PGI1 gene (referred to as the PGI1 promoter or pgi1p), a PFK1 gene (referred to as the PFK1 promoter or pfki1p), a PFK2 gene (referred to as the PFK2 promoter or the pfk2p), a FBA1 gene (referred to as the FBA1 promoter or fba1p), a TPI1 gene (referred to as a TPI1 promoter or tpi1p), a TDH1 gene (referred to as the TDH1 promoter or tdh1p), a TDH2 gene (referred to as the TDH2 promoter or tdh2p), a TDH3 gene (referred to as the TDH3 promoter or tdh3p), a PGK1 gene (referred to as the PGK1 promoter or pgk1p), a GPM1 gene (referred to as the GPM1 promoter or gpm1p), a ENO1 gene (referred to as the ENO1 promoter or eno1p), a ENO2 gene (referred to as the ENO2 promoter or eno2p), a PYK2 gene (referred to as the PYK2 promoter or pyk2p) and/or a CDC19 gene (referred to as the CDC19 or cdc19p).

Exemplary proteins capable of functioning to import glycerol include aquaporins as well as glycerol facilitators. The FPS1 protein (encoded by Gene ID 850683 in *Saccharomyces cerevisiae*) is a glycerol facilitator capable of importing glycerol. As such, the protein capable of functioning to import glycerol can be a FPS1 protein or a protein encoded by a FPS1 gene ortholog. The FPS1 protein can be derived, for example, from *Saccharomyces cerevisiae* or a corresponding ortholog found in *Pachysolen tannophilus*, *Komagataella pastoris*, *Yarrowia lipolytica* and/or *Cyberlindnera jadinii*

Another exemplary protein capable of functioning to import glycerol is the glucose-inactivated glycerol/proton symporter STL1. The native function of the STL1 protein is the uptake of glycerol from the extracellular environment. STL1 is a member of the Sugar Porter Family which is part of the Major Facilitator Superfamily (MFS). STL1 transports glycerol by proton symport meaning that the glycerol and protons are co-transported through STL1 into the cell. In *S. cerevisiae*, STL1 expression and glycerol uptake is typically repressed when there are other carbon sources such as glucose available. When the cells undergo high osmotic shock, STL1 is expressed in order to help deal with the osmotic shock by transporting the osmoprotectant glycerol into the cell and increasing the intracellular glycerol concentration. In the context of the present disclosure, the protein functioning to import glycerol can be the STL1 protein, a variant of the STL1 protein or a fragment of the STL1 protein. In the embodiments in which the protein functioning to import glycerol is a variant or a fragment of the STL1 protein, the variant or the fragment need to exhibit at least some of the biological activity of the native STL1 protein, namely the ability to act as a proton symport as indicated above.

The heterologous protein functioning to import glycerol can be encoded by a STL1 gene. The STL1 protein is natively expressed in yeasts and fungi, therefore the heterologous protein functioning to import glycerol can be derived from yeasts and fungi. STL1 genes encoding the STL1 protein include, but are not limited to, *Saccharomyces cerevisiae* Gene ID: 852149 (encoded by SEQ ID NO: 1 and shown in SEQ ID NO: 2), *Candida albicans* (encoded by SEQ ID NO: 3 and shown in SEQ ID NO: 4), *Kluyveromyces lactis* Gene ID: 2896463, *Ashbya gossypii* Gene ID: 4620396, *Eremothecium sinecaudum* Gene ID: 28724161, *Torulaspora delbrueckii* Gene ID: 11505245, *Lachancea thermotolerans* Gene ID: 8290820, *Phialophora attae* Gene ID: 28742143, *Penicillium digitatum* Gene ID: 26229435, *Aspergillus oryzae* Gene ID: 5997623, *Aspergillus fumigatus* Gene ID: 3504696, *Talaromyces atroroseus* Gene ID: 31007540, *Rasamsonia emersonii* Gene ID: 25315795, *Aspergillus flavus* Gene ID: 7910112, *Aspergillus terreus* Gene ID: 4322759, *Penicillium chrysogenum* Gene ID: 8310605, *Alternaria alternata* Gene ID: 29120952, *Paraphaeosphaeria sporulosa* Gene ID: 28767590, *Pyrenophora tritici-repentis* Gene ID: 6350281, *Metarhizium robertsii* Gene ID: 19259252, *Isaria fumosorosea* Gene ID: 30023973, *Cordyceps militaris* Gene ID: 18171218, *Pochonia chlamydosporia* Gene ID: 28856912, *Metarhizium majus* Gene ID: 26274087, *Neofusicoccum parvum* Gene ID: 19029314, *Diplodia corticola* Gene ID: 31017281, *Verticillium dahliae* Gene ID: 20711921, *Colletotrichum gloeosporioides* Gene ID: 18740172, *Verticillium alboatrum* Gene ID: 9537052, *Paracoccidioides lutzii* Gene ID: 9094964, *Trichophyton rubrum* Gene ID: 10373998, *Nannizzia gypsea* Gene ID: 10032882, *Trichophyton verrucosum* Gene ID: 9577427, *Arthroderma benhamiae* Gene ID: 9523991, *Magnaporthe oryzae* Gene ID: 2678012, *Gaeumannomyces graminis* var. *tritici* Gene ID: 20349750, *Togninia minima* Gene ID: 19329524, *Eutypa lata* Gene ID: 19232829, *Scedosporium apiospermum* Gene ID: 27721841, *Aureobasidium namibiae* Gene ID: 25414329, *Sphaerulina musiva* Gene ID: 27905328 as well as *Pachysolen tannophilus* GenBank Accession Numbers JQ481633 and JQ481634, *Saccharomyces paradoxus* STL1 (encoded by SEQ ID NO: 7 and shown in SEQ ID NO: 8) and *Pichia sorbitophilia* (encoded by SEQ ID NO: 5 and shown in SEQ ID NO: 6). In an embodiment, the STL1 protein is encoded by *Saccharomyces cerevisiae* Gene ID: 852149.

The heterologous protein functioning to import glycerol can be encoded by a STL1 gene as indicated herein or a STL1 gene ortholog. The heterologous protein functioning to import glycerol can be a STL1 protein as defined herein, a variant of the STL1 protein and/or a fragment of the STL1 protein. In addition, when more than one copy of the heterologous STL1 is included in the recombinant microbial cell, the plurality of heterologous nucleic acid molecules encoding the STL1 protein could be the same or different, integrated at the same or different integration sites.

iii. NAD-Dependent Glycerol-3-Phosphate Activity

In the context of the present disclosure, the recombinant microbial host cell has at least one second genetic modification allowing it to decrease its NAD-dependent glycerol-3-phosphate (biological) activity optionally in high osmotic conditions. In some embodiments, the recombinant microbial host cell retains substantially the same NAD-dependent glycerol-3-phosphate (biological) activity in normal to low osmotic conditions. As shown in the Examples below, the decreased NAD-dependent glycerol-3-phosphate activity in high osmotic conditions coupled to the maintenance of the NAD-dependent glycerol-3-phosphate activity in normal to low osmotic conditions allowed, amongst other things, to further increase ethanol yield, reduce glycerol production and to maintain adequate fermentation kinetics. That is why the recombinant microbial host cell of the present expresses at least one GPD protein (which can be native or heterologous to the microbial host cell).

As used herein, the expression "high osmotic conditions" refers to the presence of a high osmotic pressure, usually caused by an increase in the solute concentration in the environment surrounding the recombinant microbial host cell. In some embodiments, "high osmotic conditions" are associated with an upregulation of the HOG pathway, a concentration of sugars higher than about 50 g/L and/or equivalent to at least 1 g/L of a salt (such as NaCl) when the recombinant microbial host cell is a yeast host cell. This decrease in NAD-dependent glycerol-3-phosphate activity can be observed with respect to the same recombinant cell in normal or low osmotic conditions or with respect to a recombinant microbial host cell lacking the second genetic modification. As also used in the present disclosure, the expression "normal or low osmotic conditions" refers to conditions that are not associated with high osmotic pressure.

Most mammalian cells express two different glycerol-3-phosphate dehydrogenases (GPDs) which are necessary for glycerol production and they are expressed in response to different cellular signals: the GPD1 and the GPD2 proteins. Both proteins share 75% amino acid identity and, while they catalyze the same reaction, the differences in their amino acid sequence make them more efficient enzymes under the environmental conditions that induce their expression. GPD2 is known to be unable to fully substitute for GPD1 in the production of osmotically induced glycerol production suggesting that this enzyme has lower activity than GPD1 under osmotic stress. As shown in the Examples, below, replacing the coding sequence of the GPD1 gene by the coding sequence of the GPD2 gene allowed the recombinant yeast host cell to decrease its NAD-dependent glycerol-3-phosphate (biological) activity during high osmotic conditions while maintaining its NAD-dependent glycerol-3-phosphate (biological) activity during normal or low osmotic conditions. As also shown in Examples, modulating the expression of GPD1 and GPD2 can impair growth rate and kinetics.

The recombinant microbial host cells of the present disclosure can include a second genetic modification to inhibit (at least partially or totally) the expression of the NAD-dependent glycerol-3-phosphate activity 1 (GPD1) protein or a GPD1 gene ortholog. The second genetic modification can include a deletion, deletion or substitution of one or more of a nucleic acid residue(s) in a gene (or a gene ortholog) encoding the GPD1 protein (particularly in the gene's coding sequence) which would cause a reduction in the activity of the GPD1 protein in high osmotic conditions. In an embodiment, the second genetic modification can include the deletion of all of the coding sequence of a gene (or a gene ortholog) encoding the GPD1 protein. Alternatively or in combination, the recombinant microbial host cell can express an heterologous GPD1 protein variant or fragment having a reduced activity during high osmotic conditions when compared to the native GPD1 protein.

The GPD1 protein is natively expressed in yeasts, fungi, mammalian and plant cells. GPD1 genes encoding the GPD1 protein include, but are not limited to *Saccharomyces cerevisiae* Gene ID: 851539, *Schizosaccharomyces pombe* Gene ID: 2540547, *Schizosaccharomyces pombe* Gene ID: 2540455, *Neurospora crassa* Gene ID: 3873099, *Candida albicans* Gene ID: 3643924, *Scheffersomyces stipitis* Gene ID: 4840320, *Spathaspora passalidarum* Gene ID: 18874668, *Trichoderma reesei* Gene ID: 18482691, *Nectria haematococca* Gene ID: 9668637, *Candida dubliniensis* Gene ID: 8046432, *Chlamydomonas reinhardtii* Gene ID: 5716580, *Brassica napus* Gene ID: 106365675, *Chlorella variabilis* Gene ID: 17355036, *Brassica napus* Gene ID: 106352802, *Mus musculus* Gene ID: 14555, *Homo sapiens* Gene ID: 2819, *Rattus norvegicus* Gene ID: 60666, *Sus scrofa* Gene ID: 100153250, *Gallus gallus* Gene ID: 426881, *Bos taurus* Gene ID: 525042, *Xenopus tropicalis* Gene ID: 448519, *Pan troglodytes* Gene ID: 741054, *Canis lupus familiaris* Gene ID: 607942, *Callorhinchus milii* Gene ID: 103188923, *Columba livia* Gene ID: 102088900, *Macaca fascicularis* Gene ID: 101865501, *Myotis brandtii* Gene ID: 102257341, *Heterocephalus glaber* Gene ID: 101702723, *Nannospalax galili* Gene ID: 103746543, *Mustela putorius furo* Gene ID: 101681348, *Callithrix jacchus* Gene ID: 100414900, *Labrus bergylta* Gene ID: 109980872, *Monopterus albus* Gene ID: 109969143, *Castor canadensis* Gene ID: 109695417, *Paralichthys olivaceus* Gene ID: 109635348, *Bos indicus* Gene ID: 109559120, *Hippocampus comes* Gene ID: 109507993, *Rhinolophus sinicus* Gene ID: 109443801, *Hipposideros armiger* Gene ID: 109393253, *Crocodylus porosus* Gene ID: 109324424, *Gavialis gangeticus* Gene ID: 109293349, *Panthera pardus* Gene ID: 109249099, *Cyprinus carpio* Gene ID: 109094445, *Scleropages formosus* Gene ID: 108931403, *Nanorana parkeri* Gene ID: 108789981, *Rhinopithecus bieti* Gene ID: 108543924, *Lepidothrix coronata* Gene ID: 108509436, *Pygocentrus nattereri* Gene ID: 108444060, *Manis javanica* Gene ID: 108406536, *Cebus capucinus imitator* Gene ID: 108316082, *Ictalurus punctatus* Gene ID: 108255083, *Kryptolebias marmoratus* Gene ID: 108231479, *Miniopterus natalensis* Gene ID: 107528262, *Rousettus aegyptiacus* Gene ID: 107514265, *Coturnix japonica* Gene ID: 107325705, *Protobothrops mucrosquamatus* Gene ID: 107302714, *Parus major* Gene ID: 107215690, *Marmota marmota marmota* Gene ID: 107148619, *Gekko japonicus* Gene ID: 107122513, *Cyprinodon variegatus* Gene ID: 107101128, *Acinonyx jubatus* Gene ID: 106969233, *Poecilia latipinna* Gene ID: 106959529, *Poecilia mexicana* Gene ID: 106929022, *Calidris pugnax* Gene ID: 106891167, *Sturnus vulgaris* Gene ID: 106863139, *Equus asinus* Gene ID: 106845052, *Thamnophis sirtalis* Gene ID: 106545289, *Apteryx australis mantelli* Gene ID: 106499434, *Anser* cygnoides domesticus Gene ID: 106047703, Dipodomys ordii Gene ID: 105987539, Clupea harengus Gene ID: 105897935, Microcebus murinus Gene ID: 105869862, Propithecus coquereli Gene ID: 105818148, Aotus nancymaae Gene ID: 105709449, Cercocebus atys Gene ID: 105580359, Mandrillus leucophaeus Gene ID: 105527974, Colobus angolensis palliatus Gene ID: 105507602, Macaca nemestrina Gene ID: 105492851, Aquila chrysaetos canadensis Gene ID: 105414064, Pteropus vampyrus Gene ID: 105297559, Camelus dromedarius Gene ID: 105097186, Camelus bactrianus Gene ID: 105076223, Esox lucius Gene ID: 105016698, Bison bison bison Gene ID: 105001494, Notothenia coriiceps Gene ID: 104967388, Larimichthys crocea Gene ID: 104928374, Fukomys damarensis Gene ID: 04861981, Haliaeetus leucocephalus Gene ID: 104831135, Corvus cornix cornix Gene ID: 104683744, Rhinopithecus roxellana Gene ID: 104679694, Balearica regulorum gibbericeps Gene ID: 104630128, Tinamus guttatus Gene ID: 104575187, Mesitornis unicolor Gene ID: 104539793, Antrostomus carolinensis Gene ID: 104532747, Buceros rhinoceros silvestris Gene ID: 104501599, Chaetura pelagica Gene ID: 104385595, Leptosomus discolor Gene ID: 104353902, Opisthocomus hoazin Gene ID: 104326607, Charadrius vociferus Gene ID: 104284804, Struthio camelus australis Gene ID: 104144034, Egretta garzetta Gene ID: 104132778, Cuculus canorus Gene ID: 104055090, Nipponia nippon Gene ID: 104011969, Pygoscelis adeliae Gene ID: 103914601, Aptenodytes forsteri Gene ID: 103894920, Serinus canaria Gene ID: 103823858, Manacus vitellinus Gene ID: 103760593, Ursus maritimus Gene ID: 103675473, Corvus brachyrhynchos Gene ID: 103613218, Galeopterus variegatus Gene ID: 103598969, Equus przewalskii Gene ID: 103546083, Calypte anna Gene ID: 103536440, Poecilia reticulata Gene ID: 103464660, Cynoglossus semilaevis Gene ID: 103386748, Stegastes partitus Gene ID: 103355454, Eptesicus fuscus Gene ID: 103285288, Chlorocebus sabaeus Gene ID: 103238296, Orycteropus afer afer Gene ID: 103194426, Poecilia formosa Gene ID: 103134553, Erinaceus europaeus Gene ID: 103118279, Lipotes vexillifer Gene ID: 103087725, Python bivittatus Gene ID: 103049416, Astyanax mexicanus Gene ID: 103021315, Balaenoptera acutorostrata scammoni Gene ID: 103006680, Physeter catodon Gene ID: 102996836, Panthera tigris altaica Gene ID: 102961238, Chelonia mydas Gene ID: 102939076, Peromyscus maniculatus bairdii Gene ID: 102922332, Pteropus alecto Gene ID: 102880604, Elephantulus edwardii Gene ID: 102844587, Chrysochloris asiatica Gene ID: 102825902, Myotis davidii Gene ID: 102754955, Leptonychotes weddellii Gene ID: 102730427, Lepisosteus oculatus Gene ID: 102692130, Alligator mississippiensis Gene ID: 102576126, Vicugna pacos Gene ID: 102542115, Camelus ferus Gene ID: 102507052, Tupaia chinensis Gene ID: 102482961, Pelodiscus sinensis Gene ID: 102446147, Myotis lucifugus Gene ID: 102420239, Bubalus bubalis Gene ID: 102395827, Alligator sinensis Gene ID: 102383307, Latimeria chalumnae Gene ID: 102345318, Pantholops hodgsonii Gene ID: 102326635, Haplochromis burtoni Gene ID: 102295539, Bos mutus Gene ID: 102267392, Xiphophorus maculatus Gene ID: 102228568, Pundamilia nyererei Gene ID: 102192578, Capra hircus Gene ID: 102171407, Pseudopodoces humilis Gene ID: 102106269, Zonotrichia albicollis Gene ID: 102070144, Falco cherrug Gene ID: 102047785, Geospiza fortis Gene ID: 102037409, Chinchilla lanigera Gene ID: 102014610, Microtus ochrogaster Gene ID: 101990242, Ictidomys tridecemlineatus Gene ID: 101955193, Chrysemys picta Gene ID: 101939497, Falco peregrinus Gene ID: 101911770, Mesocricetus auratus Gene ID: 101824509, Ficedula albicollis Gene ID: 101814000, Anas platyrhynchos Gene ID: 101789855, Echinops telfairi Gene ID: 101641551, Condylura cristata Gene ID: 101622847, Jaculus jaculus Gene ID: 101609219, Octodon degus Gene ID: 101563150, Sorex araneus Gene ID: 101556310, Ochotona princeps Gene ID: 101532015, Maylandia zebra Gene ID: 101478751, Dasypus novemcinctus Gene ID: 101446993, Odobenus rosmarus divergens Gene ID: 101385499, Tursiops truncatus Gene ID: 101318662, Orcinus orca Gene ID: 101284095, Oryzias latipes Gene ID: 101154943, Gorilla gorilla Gene ID: 101131184, Ovis aries Gene ID: 101119894, Felis catus Gene ID: 101086577, Takifugu rubripes Gene ID: 101079539, Saimiri boliviensis Gene ID: 101030263, Papio anubis Gene ID: 101004942, Pan paniscus Gene ID: 100981359, Otolemur garnettii Gene ID: 100946205, Sarcophilus harrisii Gene ID: 100928054, Cricetulus griseus Gene ID: 100772179, Cavia porcellus Gene ID: 100720368, Oreochromis niloticus Gene ID: 100712149, Loxodonta africana Gene ID: 100660074, Nomascus leucogenys Gene ID: 100594138, Anolis carolinensis Gene ID: 100552972, Meleagris gallopavo Gene ID: 100542199, Ailuropoda melanoleuca Gene ID: 100473892, Oryctolagus cuniculus Gene ID: 100339469, Taeniopygia guttata Gene ID: 100225600, Pongo abelii Gene ID: 100172201, Ornithorhynchus anatinus Gene ID: 100085954, Equus caballus Gene ID: 100052204, Mus musculus Gene ID: 100198, Xenopus laevis Gene ID: 399227, Danio rerio Gene ID: 325181, Danio rerio Gene ID: 406615, Melopsittacus undulatus Gene ID: 101872435, Ceratotherium simum simum Gene ID: 101408813, Trichechus manatus latirostris Gene ID: 101359849 and Takifugu rubripes Gene ID: 101071719). In the present disclosure, the recombinant microbial cell can reduce or inhibit the expression of a GPD1 gene (or a GPD1 gene ortholog) encoding a GPD1 protein, variant or fragment.

Alternatively or in combination, the second genetic modification can include modifying the recombinant host cell to express, optionally in high osmotic conditions, a NAD-dependent glycerol-3-phosphate dehydrogenase 2 (GPD2) protein. This can be done, for example, by expressing a native and/or an heterologous gene (or gene ortholog) encoding the GPD2 protein using an osmotic promoter. In such embodiment, it is important that at least a single native copy of the gene (or the gene ortholog) encoding the GPD2 protein be under the control of the native GPD2 promoter.

In the context of the present disclosure, an "osmotic promoter" can be a promoter (or a combination of promoters) allowing the expression (or, in some embodiments, the overexpression) of a gene when the recombinant microbial host cell is placed in high osmotic conditions but refraining the expression (or, in some embodiments, the overexpression) of a gene when the recombinant microbial host cell is placed in normal or low osmotic conditions. In this embodiment, the osmotic promoter can be an inducible promoter. Osmotic promoters are usually associated with genes in the HOG1 pathway and promoters controlling the expression of genes which are upregulated in the HOG1 pathway can be used in the recombinant microbial host cell of the present disclosure. Enzymes in the HOG1 pathway whose expression is upregulated in high osmotic conditions include, but are not limited to, a NAD-dependent glycerol-3-phosphate dehydrogenase 1 gene, a dihydroxyacetone kinase gene and a trehalose-phosphatase gene. As such, in the context of the present disclosure, the osmotic promoter can be a promoter (or a combination of promoters) from a NAD-dependent glycerol-3-phosphate dehydrogenase 1 gene, a dihydroxyacetone kinase gene and/or a trehalose-phosphatase gene. In *Saccharomyces cerevisiae*, enzymes in the HOG1 pathway whose expression is upregulated in the presence of high osmotic conditions include, but are not limited to, a GPD1 gene, a DAK1 gene and a TPS2 gene. As such, in the context of the present disclosure, the osmotic promoter can be a promoter (or a combination of promoters) from a GPD1 gene (referred to as the GPD1 promoter or gpd1p), a DAK1 gene (referred to as the DAK1 promoter or dak1p) and/or a TPS2 gene (referred to as the TPS2 promoter or tps2p).

An "osmotic promoter" can also be a constitutive promoter which allows the expression of coding sequences operatively associated thereto during osmotic conditions. In some embodiments, it is preferred that the constitutive promoter be a "low" constitutive promoter. Exemplary "low" constitutive promoters could be associated with the expression of housekeeping genes, and, for example, can include the promoter of the CYC1 gene. In some embodiment, the osmotic promoter is not a high constitutive promoter.

As indicated above, the recombinant microbial host cell expresses at least one copy of a native or heterologous GPD protein. In an embodiment, the native or heterologous GPD protein is a native or heterologous GPD2 protein. In the embodiment in which the at least one GPD protein is the GPD2 protein, the recombinant microbial host cell can, in some embodiments, express one, two or more copies of an heterologous gene encoding for the GPD2 protein or a corresponding GPD2 ortholog. When one or more copies of the GPD2 gene or the GPD2 gene ortholog is present in the recombinant microbial host cell, it can be expressed under the control of one or more osmotic promoter(s). In yet a further embodiment, the heterologous GPD2 gene or GPD2 gene ortholog of the recombinant microbial host cell is expressed under the control of the GPD1 promoter, for example, by replacing one or both of the coding sequence of the GPD1 gene by the coding sequence of the GPD2 gene (or the GPD2 gene ortholog).

The GPD2 protein is expressed in bacteria, yeasts, fungi, mammalian and plant cells. GPD2 genes encoding the GPD2 protein include, but are not limited to *Mus musculus* Gene ID: 14571, *Homo sapiens* Gene ID: 2820, *Saccharomyces cerevisiae* Gene ID: 854095, *Rattus norvegicus* Gene ID: 25062, *Schizosaccharomyces pombe* Gene ID: 2541502, *Mus musculus* Gene ID: 14380, *Danio rerio* Gene ID: 751628, *Caenorhabditis elegans* Gene ID: 3565504, *Mesocricetus auratus* Gene ID: 101825992, *Xenopus tropicalis* Gene ID: 779615, *Macaca mulatta* Gene ID: 697192, *Bos taurus* Gene ID: 504948, *Canis lupus familiaris* Gene ID: 478755, *Cavia porcellus* Gene ID: 100721200, *Gallus gallus* Gene ID: 424321, *Pan troglodytes* Gene ID: 459670, *Oryctolagus cuniculus* Gene ID: 100101571, *Candida albicans* Gene ID: 3644563, *Xenopus laevis* Gene ID: 444438, *Macaca fascicularis* Gene ID: 102127260, *Ailuropoda melanoleuca* Gene ID: 100482626, *Cricetulus griseus* Gene ID: 100766128, *Heterocephalus glaber* Gene ID: 101715967, *Scheffersomyces stipitis* Gene ID: 4838862, *Ictalurus punctatus* Gene ID: 108273160, *Mustela putorius furo* Gene ID: 101681209, *Nannospalax galili* Gene ID: 103741048, *Callithrix jacchus* Gene ID: 100409379, *Lates calcarifer* Gene ID: 108873068, *Nothobranchius furzeri* Gene ID: 07384696, *Acanthisitta chloris* Gene ID: 103808746, *Acinonyx jubatus* Gene ID: 106978985, *Alligator mississippiensis* Gene ID: 102562563, *Alligator sinensis* Gene ID: 102380394, *Anas platyrhynchos, Anolis carolinensis* Gene ID: 100551888, *Anser cygnoides domesticus* Gene ID: 106043902, *Aotus nancymaae* Gene ID: 105719012, *Apaloderma vittatum* Gene ID: 104281080, *Aptenodytes forsteri* Gene ID: 103893867, *Apteryx australis mantelli* Gene ID: 106486554, *Aquila chrysaetos canadensis* Gene ID: 105412526, *Astyanax mexicanus* Gene ID: 103029081, *Austrofundulus limnaeus* Gene ID: 106535816, *Balaenoptera acutorostrata scammoni* Gene ID: 103019768, *Balearica regulorum gibbericeps, Bison bison bison* Gene ID: 104988636, *Bos indicus* Gene ID: 109567519, *Bos mutus* Gene ID: 102277350, *Bubalus bubalis* Gene ID: 102404879, *Buceros rhinoceros silvestris* Gene ID: 104497001, *Calidris pugnax* Gene ID: 106902763, *Callorhinchus milii* Gene ID: 103176409, *Calypte anna* Gene ID: 103535222, *Camelus bactrianus* Gene ID: 105081921, *Camelus dromedarius* Gene ID: 105093713, *Camelus ferus* Gene ID: 102519983, *Capra hircus* Gene ID: 102176370, *Cariama cristata* Gene ID: 104154548, *Castor canadensis* Gene ID: 109700730, *Cebus capucinus imitator* Gene ID: 108316996, *Cercocebus atys* Gene ID: 105576003, *Chaetura pelagica* Gene ID: 104391744, *Charadrius vociferus* Gene ID: 104286830, *Chelonia mydas* Gene ID: 102930483, *Chinchilla lanigera* Gene ID: 102017931, *Chlamydotis macqueenii* Gene ID: 104476789, *Chlorocebus sabaeus* Gene ID: 103217126, *Chrysemys picta* Gene ID: 101939831, *Chrysochloris asiatica* Gene ID: 102831540, *Clupea harengus* Gene ID: 105902648, *Colius striatus* Gene ID: 104549356, *Colobus angolensis palliatus* Gene ID: 105516852, *Columba livia* Gene ID: 102090265, *Condylura cristata* Gene ID: 101619970, *Corvus brachyrhynchos, Coturnix japonica* Gene ID: 107316969, *Crocodylus porosus* Gene ID: 109322895, *Cuculus canorus* Gene ID: 104056187, *Cynoglossus semilaevis* Gene ID: 103389593, *Dasypus novemcinctus* Gene ID: 101428842, *Dipodomys ordii* Gene ID: 105996090, *Echinops telfairi* Gene ID: 101656272, *Egretta garzetta* Gene ID: 104135263, *Elephantulus edwardii* Gene ID: 102858276, *Eptesicus fuscus* Gene ID: 103283396, *Equus asinus* Gene ID: 106841969, *Equus caballus* Gene ID: 100050747, *Equus przewalskii* Gene ID: 103558835, *Erinaceus europaeus* Gene ID: 103114599, *Eurypyga helias* Gene ID: 104502666, *Falco cherrug* Gene ID: 102054715, *Falco peregrinus* Gene ID: 101912742, *Felis catus* Gene ID: 101089953, *Ficedula albicollis* Gene ID: 101816901, *Fukomys damarensis* Gene ID: 104850054, *Fundulus heteroclitus* Gene ID: 105936523, *Galeopterus variegatus* Gene ID: 103586331, *Gavia stellata* Gene ID: 104250365, *Gavialis gangeticus* Gene ID: 109301301, *Gekko japonicus* Gene ID: 107110762, *Geospiza fortis* Gene ID: 102042095, *Gorilla gorilla* Gene ID: 101150526, *Haliaeetus albicilla* Gene ID: 104323154, *Haliaeetus leucocephalus* Gene ID: 104829038, *Haplochromis burtoni* Gene ID: 102309478, *Hippocampus comes* Gene ID: 109528375, *Hipposideros armiger* Gene ID: 109379867, *Ictidomys tridecemlineatus* Gene ID: 101965668, *Jaculus jaculus* Gene ID: 101616184, *Kryptolebias marmoratus* Gene ID: 108251075, *Labrus bergylta* Gene ID: 109984158, *Larimichthys crocea* Gene ID: 104929094, *Latimeria chalumnae* Gene ID: 102361446, *Lepidothrix coronata* Gene ID: 108501660, *Lepisosteus oculatus* Gene ID: 102691231, *Leptonychotes weddellii* Gene ID: 102739068, *Leptosomus discolor* Gene ID: 104340644, *Lipotes vexillifer* Gene ID: 103074004, *Loxodonta africana* Gene ID: 100654953, *Macaca nemestrina* Gene ID: 105493221, *Manacus vitellinus* Gene ID: 103757091, *Mandrillus leucophaeus* Gene ID: 105548063, *Manis javanica* Gene ID: 108392571, *Marmota marmota marmota* Gene ID: 107136866, *Maylandia zebra* Gene ID: 101487556, *Mesitornis unicolor* Gene ID: 104545943,

*Microcebus murinus* Gene ID: 105859136, *Microtus ochrogaster* Gene ID: 101999389, *Miniopterus natalensis* Gene ID: 107525674, *Monodelphis domestica* Gene ID: 100014779, *Monopterus albus* Gene ID: 109957085, *Myotis brandtii* Gene ID: 102239648, *Myotis davidii* Gene ID: 102770109, *Myotis lucifugus* Gene ID: 102438522, *Nanorana parkeri* Gene ID: 108784354, *Nestor notabilis* Gene ID: 104399051, *Nipponia nippon* Gene ID: 104012349, *Nomascus leucogenys* Gene ID: 100590527, *Notothenia coriiceps* Gene ID: 104964156, *Ochotona princeps* Gene ID: 101530736, *Octodon degus* Gene ID: 101591628, *Odobenus rosmarus divergens* Gene ID: 101385453, *Oncorhynchus kisutch* Gene ID: 109870627, *Opisthocomus hoazin* Gene ID: 104338567, *Orcinus orca* Gene ID: 101287409, *Oreochromis niloticus* Gene ID: 100694147, *Ornithorhynchus anatinus* Gene ID: 100081433, *Orycteropus afer afer* Gene ID: 103197834, *Oryzias latipes* Gene ID: 101167020, *Otolemur garnettii* Gene ID: 100966064, *Ovis aries* Gene ID: 443090, *Pan paniscus* Gene ID: 100970779, *Panthera pardus* Gene ID: 109271431, *Panthera tigris altaica* Gene ID: 102957949, *Pantholops hodgsonii* Gene ID: 102323478, *Papio anubis* Gene ID: 101002517, *Paralichthys olivaceus* Gene ID: 109631046, *Pelodiscus sinensis* Gene ID: 102454304, *Peromyscus maniculatus bairdii* Gene ID: 102924185, *Phaethon lepturus* Gene ID: 104624271, *Phalacrocorax carbo* Gene ID: 104049388, *Physeter catodon* Gene ID: 102978831, *Picoides pubescens* Gene ID: 104296936, *Poecilia latipinna* Gene ID: 106958025, *Poecilia mexicana* Gene ID: 106920534, *Poecilia reticulata* Gene ID: 103473778, *Pongo abelii* Gene ID: 100452414, *Propithecus coquereli* Gene ID: 105807399, *Protobothrops mucrosquamatus* Gene ID: 107289584, *Pseudopodoces humilis* Gene ID: 102109711, *Pterocles gutturalis* Gene ID: 104461236, *Pteropus alecto* Gene ID: 102879110, *Pteropus vampyrus* Gene ID: 105291402, *Pundamilia nyererei* Gene ID: 102200268, *Pygocentrus nattereri* Gene ID: 108411786, *Pygoscelis adeliae* Gene ID: 103925329, *Python bivittatus* Gene ID: 103059167, *Rhincodon typus* Gene ID: 109920450, *Rhinolophus sinicus* Gene ID: 109445137, *Rhinopithecus bieti* Gene ID: 108538766, *Rhinopithecus roxellana* Gene ID: 104654108, *Rousettus aegyptiacus* Gene ID: 107513424, *Saimiri boliviensis* Gene ID: 101027702, *Salmo salar* Gene ID: 106581822, *Sarcophilus harrisii* Gene ID: 100927498, *Scleropages formosus* Gene ID: 108927961, *Serinus canaria* Gene ID: 103814246, *Sinocyclocheilus grahami* Gene ID: 107555436, *Sorex araneus* Gene ID: 101543025, *Stegastes partitus* Gene ID: 103360018, *Struthio camelus australis* Gene ID: 104138752, *Sturnus vulgaris* Gene ID: 106861926, *Sugiyamaella lignohabitans* Gene ID: 30033324, *Sus scrofa* Gene ID: 397348, *Taeniopygia guttata* Gene ID: 100222867, *Takifugu rubripes* Gene ID: 101062218, *Tarsius syrichta* Gene ID: 103254049, *Tauraco erythrolophus* Gene ID: 104378162, *Thamnophis sirtalis* Gene ID: 106538827, *Tinamus guttatus* Gene ID: 104572349, *Tupaia chinensis* Gene ID: 102471148, *Tursiops truncatus* Gene ID: 101330605, *Ursus maritimus* Gene ID: 103659477, *Vicugna pacos* Gene ID: 102533941, *Xiphophorus maculatus* Gene ID: 102225536, *Zonotrichia albicollis* Gene ID: 102073261, *Ciona intestinalis* Gene ID: 100183886, *Meleagris gallopavo* Gene ID: 100546408, *Trichechus manatus latirostris* Gene ID: 101355771, *Ceratotherium simum simum* Gene ID: 101400784, *Melopsittacus undulatus* Gene ID: 101871704, *Esox lucius* Gene ID: 10502249 and *Pygocentrus nattereri* Gene ID: 108411786. In an embodiment, the GPD2 protein is encoded by *Saccharomyces cerevisiae* Gene ID: 854095.

The heterologous GPD2 protein can be encoded by a GPD2 gene or a GPD2 gene ortholog as defined herein. The heterologous GPD2 protein can also be a variant of the GPD2 protein and/or a fragment of the GPD2 protein. In addition, when more than one copy of the heterologous GPD2 gene or gene ortholog is included in the recombinant microbial cell, the plurality of heterologous nucleic acid molecules encoding the GPD2 protein could be the same or different, integrated at the same or different integration sites.

iv) Additional Modifications and Combinations

The recombinant microbial host cell of the present disclosure does not need to have additional genetic modifications besides those made for the purpose of increasing the activity of the protein functioning to import glycerol during glycolytic conditions and for decreasing the activity of NAD$^+$-dependent glycerol-3-phosphate dehydrogenase during high osmotic conditions. However, in some embodiments, the recombinant microbial host cell can include one or more additional genetic modifications coding for an enzyme, can be co-cultured with additional recombinant host cells including additional genetic modifications coding for enzymes or can be used with heterologous (purified) enzymes described herein.

For example, the additional enzyme can allow for the production of an heterologous glucoamylase. Many microbes produce an amylase to degrade extracellular starches. In addition to cleaving the last α(1-4) glycosidic linkages at the non-reducing end of amylose and amylopectin, yielding glucose, γ-amylase will cleave α(1-6) glycosidic linkages. The heterologous glucoamylase can be derived from any organism. In an embodiment, the heterologous protein is derived from a γ-amylase, such as, for example, the glucoamylase of *Saccharomycoces filbuligera* (e.g., encoded by the glu 0111 gene). The GLU0111 polypeptide includes the following amino acids (or correspond to the following amino acids) which are associated with glucoamylase activity and include, but are not limited to amino acids located at positions 41, 237, 470, 473, 479, 485, 487 of SEQ ID NO: 9. Examples of recombinant yeast host cells expressing such enzymes are described in WO 2011/153516 as well as in WO 2017/037614.

In yet another example, the enzyme can reduce the production of one or more native enzyme that functions to catabolize (breakdown) formate. As used in the context of the present disclosure, the expression "native polypeptides that functions to catabolize formate" refers to polypeptides which are endogenously found in the recombinant yeast host cell. Native enzymes that functions to catabolize formate include, but are not limited to, the FDH1 and the FDH2 polypeptides (also referred to as FDH1 and FDH2 respectively). In an embodiment, the recombinant yeast host cell bears a genetic modification in at least one of the FDH1 gene (encoding the FDH1 polypeptide), the FDH2 gene (encoding the FDH2 polypeptide) or orthologs thereof. In another embodiment, the recombinant yeast host cell bears genetic modifications in both the FDH1 gene (encoding the FDH1 polypeptide) and the fdh2 gene (encoding the FDH2 polypeptide) or orthologs thereof. Examples of recombinant yeast host cells bearing such genetic modification(s) leading to the reduction in the production of one or more native enzymes that functions to catabolize formate are described in WO 2012/138942. Preferably, the recombinant yeast host cell has genetic modifications (such as a genetic deletion or insertion) in the FDH1 gene and in the FDH2 gene which would cause the host cell to have knocked-out FDH1 and FDH2 genes.

In still another example, the enzyme can increase the production of an heterologous enzyme that functions to anabolize (form) formate. As used in the context of the present disclosure, "an enzyme that functions to anabolize formate" refers to polypeptides which may or may not be endogenously found in the recombinant yeast host cell and that are purposefully introduced into the recombinant yeast host cells. In some embodiments, the heterologous enzyme that functions to anabolize formate is an heterologous pyruvate formate lyase (PFL), an heterologous acetaldehyde dehydrogenases, an heterologous alcohol dehydrogenases, and/or and heterologous bifunctional acetylaldehyde/alcohol dehydrogenases (AADH) such as those described in U.S. Pat. No. 8,956,851 and WO 2015/023989. More specifically, PFL and AADH enzymes for use in the recombinant yeast host cells can come from a bacterial or eukaryotic source. Heterologous PFL of the present disclosure include, but are not limited to, the PFLA polypeptide, a polypeptide encoded by a PFLA gene ortholog, the PFLB polypeptide or a polypeptide encoded by a PFLB gene ortholog. Heterologous AADHs of the present disclosure include, but are not limited to, the ADHE polypeptides or a polypeptide encoded by an ADHE gene ortholog. In an embodiment, the recombinant yeast host cell of the present disclosure comprises at least one of the following heterologous enzymes that functions to anabolize formate: the PFLA polypeptide, the PFLB polypeptide and/or the ADHE polypeptide. In an embodiment, the recombinant yeast host cell of the present disclosure comprises at least two of the following heterologous enzymes that functions to anabolize formate: the PFLA polypeptide, the PFLB polypeptide and/or the ADHE polypeptide. In another embodiment, the recombinant yeast host cell of the present disclosure comprises the following heterologous enzymes that functions to anabolize formate: the PFLA polypeptide, the PFLB polypeptide and the ADHE polypeptide.

In some embodiments, the enzyme involved in the cleavage or hydrolysis of its substrate (e.g., a lytic enzyme and, in some embodiments, a saccharolytic enzyme). In still another embodiment, the enzyme can be a glycoside hydrolase. In the context of the present disclosure, the term "glycoside hydrolase" refers to an enzyme involved in carbohydrate digestion, metabolism and/or hydrolysis, including amylases, cellulases, hemicellulases, cellulolytic and amylolytic accessory enzymes, inulinases, levanases, trehalases, pectinases, sucranases, dextranase, and pentose sugar utilizing enzymes. In another embodiment, the enzyme can be a protease. In the context of the present disclosure, the term "protease" refers to an enzyme involved in protein digestion, metabolism and/or hydrolysis. In yet another embodiment, the enzyme can be an esterase. In the context of the present disclosure, the term "esterase" refers to an enzyme involved in the hydrolysis of an ester from an acid or an alcohol, including phosphatases such as phytases.

The additional enzyme can be an "amylolytic enzyme", an enzyme involved in amylose digestion, metabolism and/or hydrolysis. The term "amylase" refers to an enzyme that breaks starch down into sugar. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In an embodiment, the heterologous protein is derived from a α-amylase such as, for example, from the α-amylase of Bacillus amyloliquefaciens. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Another amylolytic enzyme is α-glucosidase that acts on maltose and other short malto-oligosaccharides produced by α-, β-, and γ-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullulan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

The additional enzyme can be a "dextranase". Dextran is a complex branched polysaccharide composed of glucose monomer units. It contains a straight chain of α-1,6 glycosidic linkages, and branches linked by α-1,2, α-1,3, or α-1,4 glycosidic bonds. Several enzymes participate in the breakdown of dextran. Dextranase (EC 3.2.1.11), also known as alpha-1,6-glucan-6-glucanohydrolase, is an enzyme that carries out the endohydrolysis of α-1,6 glycosidic bonds in dextran. Other enzymes that act to break down dextran include: glucan-1,6-α-D-glucosidases (EC3.2.1.70), glucan-1,6-α-isomaltosidases (EC3.2.1.94), dextran 1,6-α-isomaltotriosidases (EC3.2.1.95), branched-dextran exo-1,2-α-glucosidases (EC3.2.1.115), α-glucosidase (EC3.2.1.20) and cycloisomaltooligosaccharide glucanotransferase (CITase).

The additional enzyme can be a "cellulolytic enzyme", an enzyme involved in cellulose digestion, metabolism and/or hydrolysis. The term "cellulase" refers to a class of enzymes that catalyze cellulolysis (i.e. the hydrolysis) of cellulose. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

The additional enzyme can have "hemicellulolytic activity", an enzyme involved in hemicellulose digestion, metabolism and/or hydrolysis. The term "hemicellulase" refers to a class of enzymes that catalyze the hydrolysis of cellulose. Several different kinds of enzymes are known to have hemicellulolytic activity including, but not limited to, xylanases and mannanases.

The additional enzyme can have "xylanolytic activity", an enzyme having the is ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. The heterologous protein can also be a "xylose metabolizing enzyme", an enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein. A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

The additional enzyme can have "mannanic activity", an enzyme having the is ability to hydrolyze the terminal, non-reducing β-D-mannose residues in β-D-mannosides. Mannanases are capable of breaking down hemicellulose, one of the major components of plant cell walls. Xylanases include those enzymes that correspond to Enzyme Commission Number 3.2.25.

The additional enzyme can be a "pectinase", an enzyme, such as pectolyase, pectozyme and polygalacturonase, commonly referred to in brewing as pectic enzymes. These enzymes break down pectin, a polysaccharide substrate that is found in the cell walls of plants.

The additional enzyme can have "phytolytic activity", an enzyme catalyzing the conversion of phytic acid into inorganic phosphorus. Phytases (EC 3.2.3) can be belong to the histidine acid phosphatases, β-propeller phytases, purple acid phosphatases or protein tyrosine phosphatase-like phytases family.

The additional enzyme can have "proteolytic activity", an enzyme involved in protein digestion, metabolism and/or hydrolysis, including serine proteases, threonine proteases, cysteine proteases, aspartate proteases, glutamic acid proteases and metalloproteases.

When the recombinant yeast host cell expresses an heterologous protein, it can be further modified to increase its robustness at high temperatures. Genetic modifications for increasing the robustness of a genetically-modified recombinant yeast host cell are described in WO2017/037614.

In some embodiments, the recombinant microbial host cells of the present disclosure do not have (e.g., exclude) a genetic modification in its NADH-consuming glutamate synthase gene. In *Saccharomyces cerevisiae*, the NADH-consuming glutamate synthase gene is known as GLT1 (as described in Wang et al., 2013).

In still another embodiment, the recombinant microbial host cells of the present disclosure do not have (e.g., exclude) genetic modifications in genes encoding heterologous enzymes that functions in one or more engineered metabolic pathways to convert a carbohydrate source to an alcohol, such as those described in WO2015/023989.

v) Fermentation Processes

The biomass that can be fermented with the recombinant host cell described herein includes any type of biomass known in the art and described herein. For example, the biomass can include, but is not limited to, starch, sugar and lignocellulosic materials. Starch materials can include, but are not limited to, mashes such as corn, wheat, rye, barley, rice, or milo. Sugar materials can include, but are not limited to, sugar beets, artichoke tubers, sweet sorghum, molasses or sugarcane. The terms "lignocellulosic material", "lignocellulosic substrate" and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants and sugar-processing residues. The terms "hemicellulosics", "hemicellulosic portions" and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan and galactoglucomannan), pectins (e.g., homogalacturonans, rhamnogalacturonan I and II, and xylogalacturonan) and proteoglycans (e.g., arabinogalactan-protein, extensin, and pro line-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (AVICEL®), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, molasses, sugarcane, leaves, agricultural and forestry residues, grasses such as switchgrass, ruminant digestion products, municipal wastes, paper mill effluent, newspaper, cardboard or combinations thereof.

Paper sludge is also a viable feedstock for lactate or acetate production. Paper sludge is solid residue arising from pulping and paper-making, and is typically removed from process wastewater in a primary clarifier. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

In some embodiments, the present disclosure provides method for hydrolyzing a substrate comprising the biomass as described above, for example a substrate comprising molasses, sugar cane or a derivative therefrom, by contacting the substrate with a recombinant microbial host cell described herein. In some embodiments, the present disclosure provides a method for hydrolyzing a substrate, for example substrate comprising molasses, sugar cane or a derivative therefrom, by contacting the substrate with a co-culture comprising the recombinant microbial host cells described and another microorganism, such as, for example, a non-genetically-modified microorganism. In some embodiments, the method can also comprise including a purified enzyme to allow or facilitate the hydrolysis of the substrate or of an intermediary product made by the recombinant microbial host cell of the present disclosure.

The production of ethanol can be performed, for example, at temperatures of at least about 30° C., about 31° C., about 32° C., about 33°, about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the production of ethanol from cellulose can be performed, for example, at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments, the recombinant microbial host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the production of ethanol (or other products and co-products) can further be performed according to the "Brazil process." Under the "Brazil process," non-sterilized sugarcane juice and/or molasses is fermented at a high inoculum to achieve fast fermentations. During the fermentation process, the yeast is repeatedly recycled over the 200+ day crop season by centrifuging the cells and washing them in sulphuric acid to decrease contamination and break up flocculation of cells. Industrial strains isolated from ethanol fermentations in Brazil have been shown to have characteristics that allow them to survive the acid washing and fermentation conditions better than typical lab yeast or other industrial yeast isolates. One commonly used *S. cerevisiae* strain in Brazil, PE-2, is a wild isolate from sugarcane ethanol fermentation (see Argueso et al., 2009, see also JAY291 genome, *Saccharomyces* Genome Database (SGD), yeastgenome.org). In the Brazil cane ethanol fermentations, PE-2 and other industrial strains produce an average of 4.5 g/L glycerol. In some embodiments, the PE-2 strain, or a modified version thereof, is used as the host organism. In certain embodiments, ethanol is produced through the fermentation of a recombinant microbial host cell according to the Brazil process. In some embodiments, the recombinant microbial host cell is used to ferment a carbohydrate source wherein the microorganisms are reused after one or more fermentations (e.g., cycles), and wherein the microorganisms are washed with an acid (e.g., acid washed) following each fermentation. In some embodiments, the acid has a pH of between 2.0 and 2.2. In certain embodiments, the acid is sulphuric acid. In some additional embodiments, the acid washing cycle can be repeated more than once, for example, 2, 3, 4, 5, 6, 7, 8, 9, 10, 11, 12, 13, 14, 15, 16, 17, 18, 19, 20, 25, 30, 35, 40, 45, 50, 55, 60 or more acid washing cycles can be performed.

In some embodiments, methods of producing ethanol can comprise contacting the fermentation substrate with a recombinant microbial host cell or co-culture as described herein and additionally contacting the substrate with externally produced enzymes which can be provided in a purified form. Exemplary externally produced enzymes include, but are not limited to starch degrading enzymes, dextran degrading enzymes, phytase, protease, cellulases and/or xylose isomerase. Specific externally produced (and optionally purified) enzymes include, but are not limited to, trehalases, glucoamylases, alpha-amylases, alpha-glucosidases, glucanases (endo/exo), pullulanases, phytases and/or proteases.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter or at least about 15 g per hour per liter.

In some embodiments, the recombinant microbial host cells can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, at least about 500 mg per hour per liter, at least about 600 mg per hour per liter, at least about 700 mg per hour per liter, at least about 800 mg per hour per liter, at least about 900 mg per hour per liter, at least about 1 g per hour per liter, at least about 1.5 g per hour per liter, at least about 2 g per hour per liter, at least about 2.5 g per hour per liter, at least about 3 g per hour per liter, at least about 3.5 g per hour per liter, at least about 4 g per hour per liter, at least about 4.5 g per hour per liter, at least about 5 g per hour per liter, at least about 5.5 g per hour per liter, at least about 6 g per hour per liter, at least about 6.5 g per hour per liter, at least about 7 g per hour per liter, at least about 7.5 g per hour per liter, at least about 8 g per hour per liter, at least about 8.5 g per hour per liter, at least about 9 g per hour per liter, at least about 9.5 g per hour per liter, at least about 10 g per hour per liter, at least about 10.5 g per hour per liter, at least about 11 g per hour per liter, at least about 11.5 g per hour per liter, at least about 12 g per hour per liter, at least about 12.5 g per hour per liter, at least about 13 g per hour per liter, at least about 13.5 g per hour per liter, at least about 14 g per hour per liter, at least about 14.5 g per hour per liter, at least about 15 g per hour per liter or more than a control strain (e.g., a wild-type strain, such as, for example, strain M7101) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. The present invention will be more readily understood by referring to the following examples which are given to illustrate the invention rather than to limit its scope.

EXAMPLES

Example I—Comparison Between Different Glycerol Reducing Pathways

Various *Saccharomyces cerevisiae* strains (all derived from the wild-type M7101 strain) were genetically engineered to reduce glycerol production during ethanol production to determine if it could increase ethanol production. Two strains were developed to use an alternate electron acceptor to replace the NADH/NAD$^+$ balancing function of glycerol production. Strain M8690 used formate as the alternate electron accepter. More specifically, strain M8690 overexpressed an heterologous pyruvate formate lyase and acetaldehyde dehydrogenase and did not express its native formate dehydrogenase and reduced the expression of glycerol-3-phosphate dehydrogenase genes. Strain M8376 used the acetic acid conversion to ethanol as an electron sink. More specifically, strain M8376 was made by overexpressing an acetaldehyde dehydrogenase and deleting gpd2, one of the glycerol-3-phosphate dehydrogenase genes. Strain M7772 was made by overexpressing the native glycerol transporter (e.g., STL1) which not normally active during fermentation to limit glycerol production. Strains M7762, M7763 and M7764 were made by inactivating the gene encoding for the aquaglyercoporin FPS1 (e.g., a protein capable of exporting glycerol out of the cell). The genotype of the various strains used in this example is presented in Table 1.

TABLE 1

Genotype of the Various Strains Used in this Example

| Name | Genotype |
|---|---|
| M7101 | Non genetically modified (wild-type) *Saccharomyces cerevisiae* |
| M7762 | Δfps1 |
| M7763 | Δfps1 |
| M7764 | Δfps1 |
| M7768 | Ime1 Δ::STL1 (4X) |
| M7769 | Ime1 Δ::STL1 (4X) |
| M7772 | Δfcy:: STL1 (4x) |
| M8690 | Δ296W::*B. adolescentis* pflA/pflB/adhE Δfdh2 Δfdh1 Δgpd2:: *B. adolescentis* pflA/pflB/adhE |
| M8376 | Δgpd2:: *B. adolescentis* adhE |
| M8397 | Δ296W:: STL1 (4x) Δfcy:: STL1 (4x) |
| M10753 | ime1Δ::STL1 (4x) fcy1Δ::STL1 (4x) |
| M10761 | ime1Δ::STL1 (4x) 296WΔ::STL1 (4x) fcy1Δ::STL1 (4x) |

Lab scale fermentations were carried out using 50 mL or 2 L vessels filled with yeast cream either from propagation, or from a previous fermentation, at a level to reproduce standard yeast concentrations in Brazilian ethanol fermentations (~10% wet cell mass). This yeast cream was subjected to acid treatment under conditions identical to Brazilian industrial practice. A feeding system was then used to provide a feed of substrate or "must" (sugar cane juice, molasses, or a mixture, sourced from operating Brazilian facilities), again at rates and concentrations dictated by average conditions occurring in Brazilian facilities. This feed stream was provided via a syringe pump to provide excellent accuracy with respect to the amount of substrate fed to each reactor. Fermentations were held under temperature controlled conditions and gently agitated, and were allowed to proceed until the evolution of $CO_2$ falls below a minimum threshold. Once complete, samples were taken for analysis by HPLC to compare the production of ethanol, glycerol, organic acids, and other compounds.

Monitoring the $CO_2$ off-gas rate of the fermentation allows an indirect determination of the sugar consumption and ethanol production rates. After feeding starts (at time=0), the fermentation rate rises to a maximum, and then stays at that maximum until feeding is finished after about 4.5 hours. After feeding is complete, the strains utilize the remaining sugars.

Figure 1:
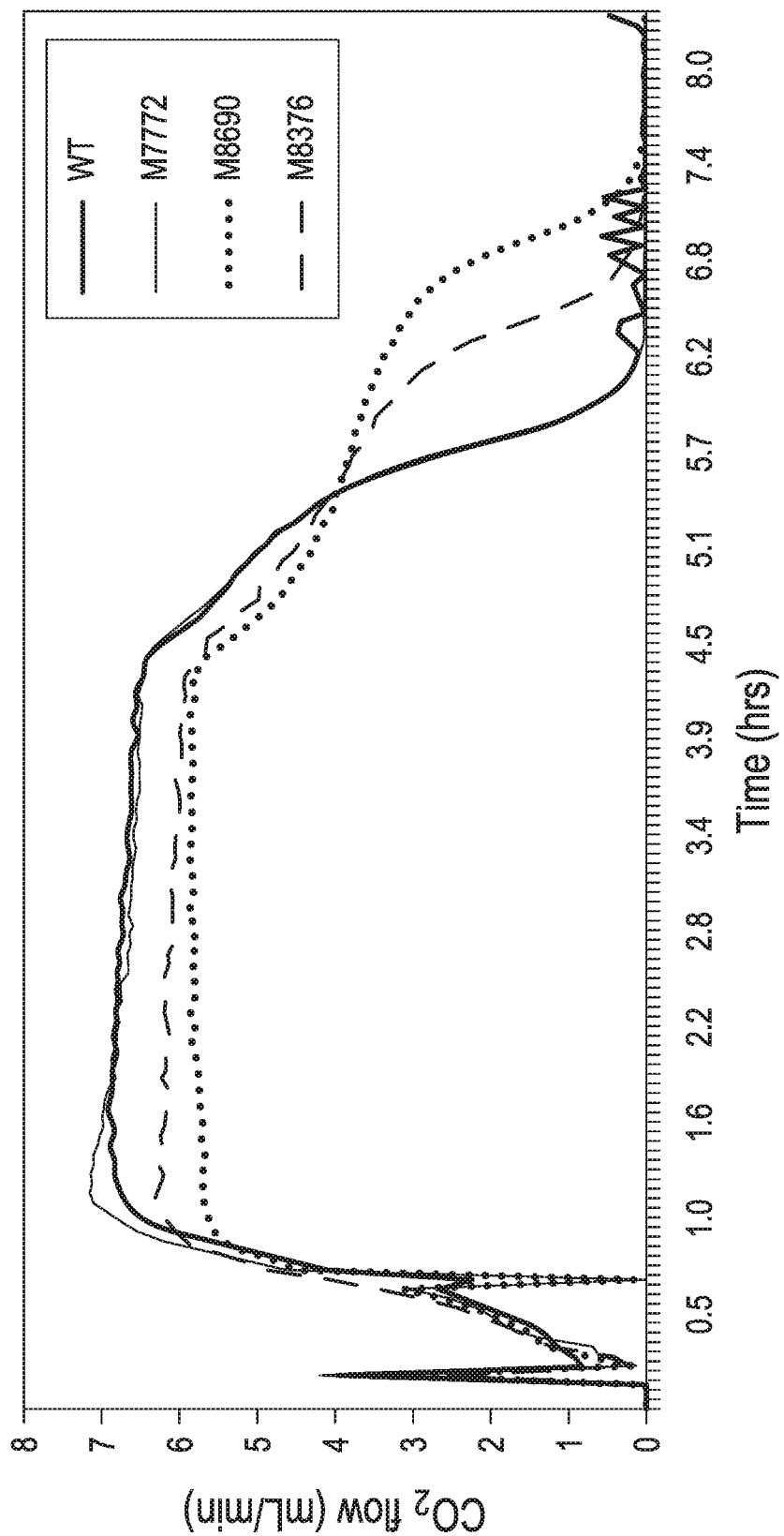
FIG. 1 compares the $CO_2$ off-gas rates of fed-batch fermentations with strains M7101 (wild-type, thick black line), M7772 (thin black line), M8690 (dotted line) or M8376 (dashed line). Results are presented as $CO_2$ flow (mL/min) in function of time (hours) for the different strains tested. See Example I for a description of the various strains used.

Strains M7101, M7772, M8690 and M8376 were subjected to 56 rounds of fermentation and acid washing. For strain M8690, the first 20 rounds of fermentation showed that it could achieve a 1.8% increase in ethanol yield, and 27% decrease in glycerol production relative to strain M7101. However, its viability decreased rapidly after fermentation 20 and strain M8690 began to leave sugars unfermented in the reaction (data not shown). In addition, as is shown in FIG. 1, the ability of strain M8690 to quickly finish fermentation was compromised as finishing the process required an additional hour relative to strain M7101 (e.g., about a 16% increase in time when compared to strain M7101).

Strain M8376 showed a 2.1% increase in ethanol yield and a 32% decrease in glycerol production over 56 cycles (data not shown). However, strain M8376 also showed a slower fermentation rate compared to the fermentation rate of strain M7101. The results presented on FIG. 1 indicate that strain M8376 finished the fermentation about 30 minutes slower than M7101 2 (e.g., about a 16% increase in time when compared to strain M7101).

Strain M7772 showed a 1.1% ethanol yield increase and a 14% decrease in glycerol production over 56 cycles (data not shown). Unlike strains M8690 and M8376, strain M7772 showed a very fast fermentation rate throughout the rounds of fermentation. As shown in FIG. 1, strain M7772 was able to ferment sugar as fast or faster than strain M7101, and was also able to finish the fermentation quickly.

Figure 2:
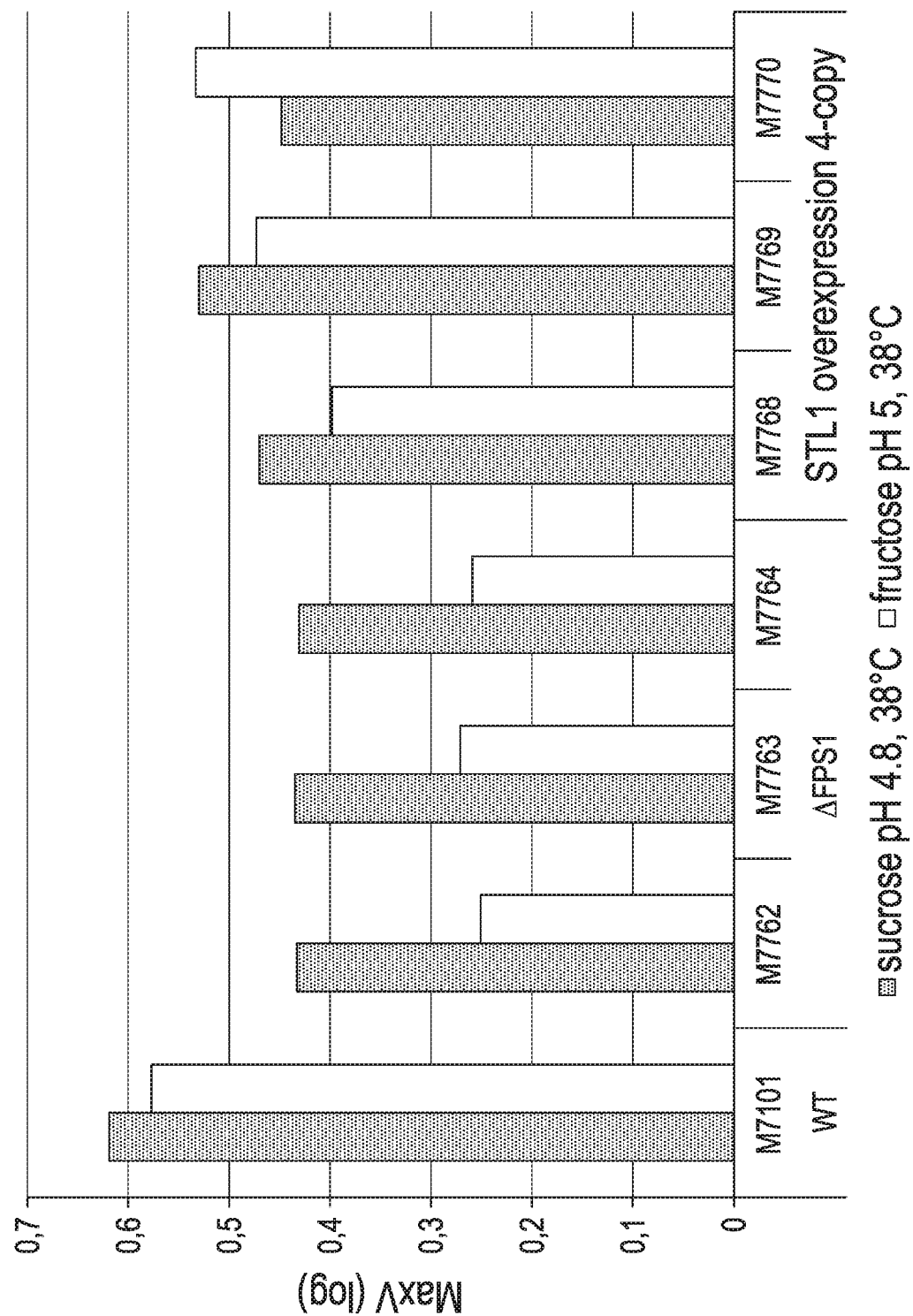
FIG. 2 compares the maximal growth rate (on a logarithmic scale) of strains M7101, M7762, M7763, M7764, M7768, M7769 and M7770 grown in either sucrose (grey bars) or fructose (white bars) at 38° C. See Example I for a description of the various strains used.

The impact of inhibiting the expression level of the FPS1 gene was assessed. The robustness of three different strains in which the FPS1 gene has been deleted (e.g., M7762, M7763 and M7764) has been compared to the robustness of three different strains overexpressing the STL1 gene (e.g., M7768, M7769 and M7770). Briefly, strains were pre-cultured on YP medium supplemented with sucrose and then were diluted into fresh YP+sucrose or YP+fructose media for growth rate comparison. The optical density of the culture was monitored anaerobically using a BIOTEK® plate reader inside of an anaerobic chamber at a temperature of 38° C. and enabled the calculation of the maximum growth rate of the cultures as well as the time at which the maximum growth rate was reached. As shown on FIG. 2, strains in which the FPS1 gene has been deleted grew more slowly in both sucrose and fructose when placed at 38° C.

Figure 3:
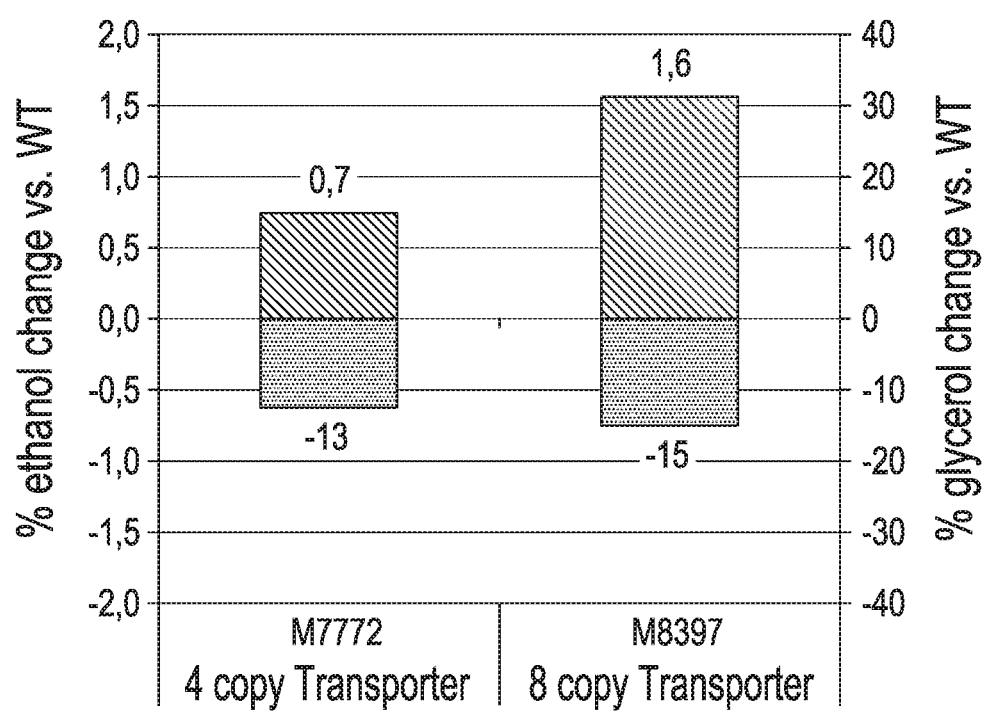
FIG. 3 compares the percentage increase in ethanol yield (when compared to the wild-type strain M7101, as shown in diagonal hatch bars, left axis) and the percentage of glycerol reduction (when compared to the wild-type strain M7101, as show in dotted bars, right axis) between strains M7772 and M8397. See Example I for a description of the various strains used.

The impact of increasing the expression level of the STL1 gene was then assessed in additional genetically modified strains derived from strain M7101. The percentage of ethanol increase/glycerol reduction (when compared to parental strain M7101) of strain M7772 was compared to strain M8397 (which includes 4 heterologous additional copies of the STL1 gene). As shown in FIG. 3, the inclusion of 4 additional copies of STL1 in strain M8397 increased ethanol yield and decreased glycerol production when compared to strain M7772.

Figure 4:
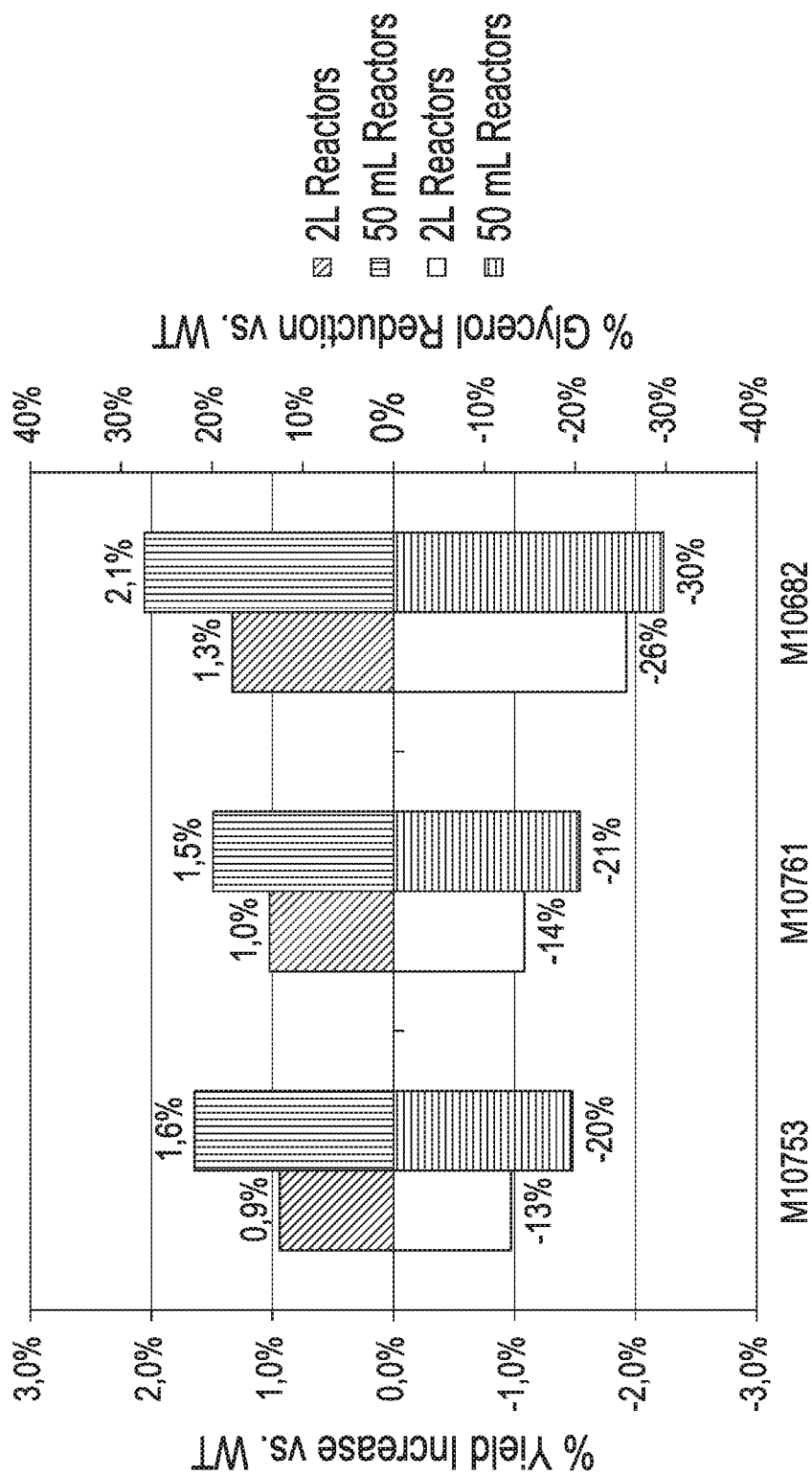
FIG. 4 compares the percentage increase in ethanol yield (when compared to the wild-type strain M7101, as show in diagonal hatch bars (2 L reactor) or vertical bars (50 mL reactor), left axis) and the percentage of glycerol reduction (when compared to the wild-type strain M7101, as shown in the white bars (2 L reactor) or horizontal bars (50 mL reactor), right axis) between strains M10753, M10761 and M10682. See Example II for a description of the various strains used.

Strain M10753 was made by including 8 copies of the STL1 gene whereas strain M10761 was made by including 12 copies of the STL1 gene. Strains M10753, M10671 and M10682 were tested in fed-batch fermentation and acid recycle at both the 50 mL scale as well as at the 2 L scale as described above. FIG. 4 shows that the ethanol yield for strain M10761 was not increased relative to strain M10753, with both strains providing about a 1 to 1.5% ethanol yield increase and a 15 to 20% decrease in glycerol production.

Figure 5:
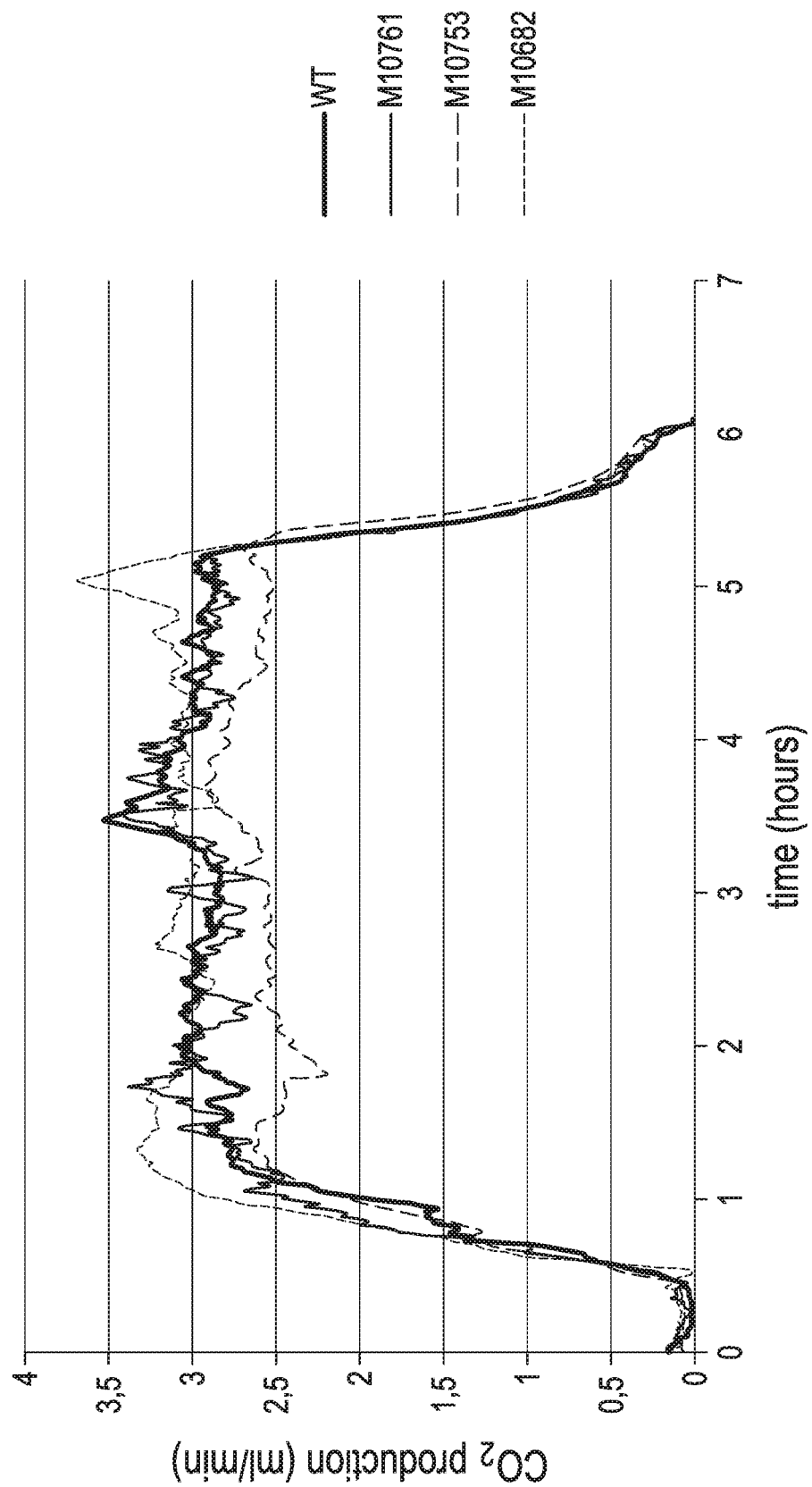
FIG. 5 compares the $CO_2$ off-gas rates for strains M7101 (thick black line), M10761 (thin black line), M10753 (dashed (long) line) and M10682 (dashed (short) line) in the 2 L fermentation system. Results are presented as $CO_2$ flow (mL/min) as a function of time (hours) for the different strains tested. See Example II for a description of the various strains used.

The impact of increasing the expression level of the STL1 gene on the fermentation kinetics was then determined. FIG. 5 provides the fermentation rate data from one of the fermentation rounds carried out in the 2 L fermenters, and shows that, as seen in FIG. 1, the overexpression of the STL1 gene did not negatively impact the rate of fermentation or the time needed to complete the fermentation.

Example II—Combinations with Modifications in the Glycerol-3-Phosphate Dehydrogenase The impact of modifying the expression of the glycerol-3-phosphate dehydrogenase was investigated. All the strains used in this example were derived from strain M7101 and their genotype is provided in Table 2.

TABLE 2

Genotype of the Various Strains Used in this Example

| Name | Genotype |
|---|---|
| M7101 | Non genetically modified (e.g., wild-type) *Saccharomyces cerevisiae* |
| M7772 | Δfcy:: STL1 (4x) |
| M8190 | Δ gpd2::GDP1 |
| M8262 | Δ gpd1::GPD2 |
| M8397 | Δ296W:: STL1 (4x) Δfcy:: STL1 (4x) |
| M8376 | Δgpd2:: *B. adolescentis* adhE |
| M10648 | Δ ime1::STL1 (4x) |
| M10682 | Δ ime1::STL1 (4x) Δ fcy1::STL1 (4x) Δ gpd1::GPD2 |
| M10686 | Δ gpd2::GPD1 Δime1::STL1 (4x) Δfcy1::STL1 (4x) |
| M10715 | Δ gpd1::GPD2 Δimel::STL1 (4x) |
| M10716 | Δ gpd2::GPD1 Δ ime1::STL1 (4x) |
| M10753 | Δ ime1::STL1 (4x) Δfcy1::STL1 (4x) |
| M10761 | Δ ime1::STL1 (4x) Δ296W::STL1 (4x) Δ fcy1::STL1 (4x) |

Figure 6A:
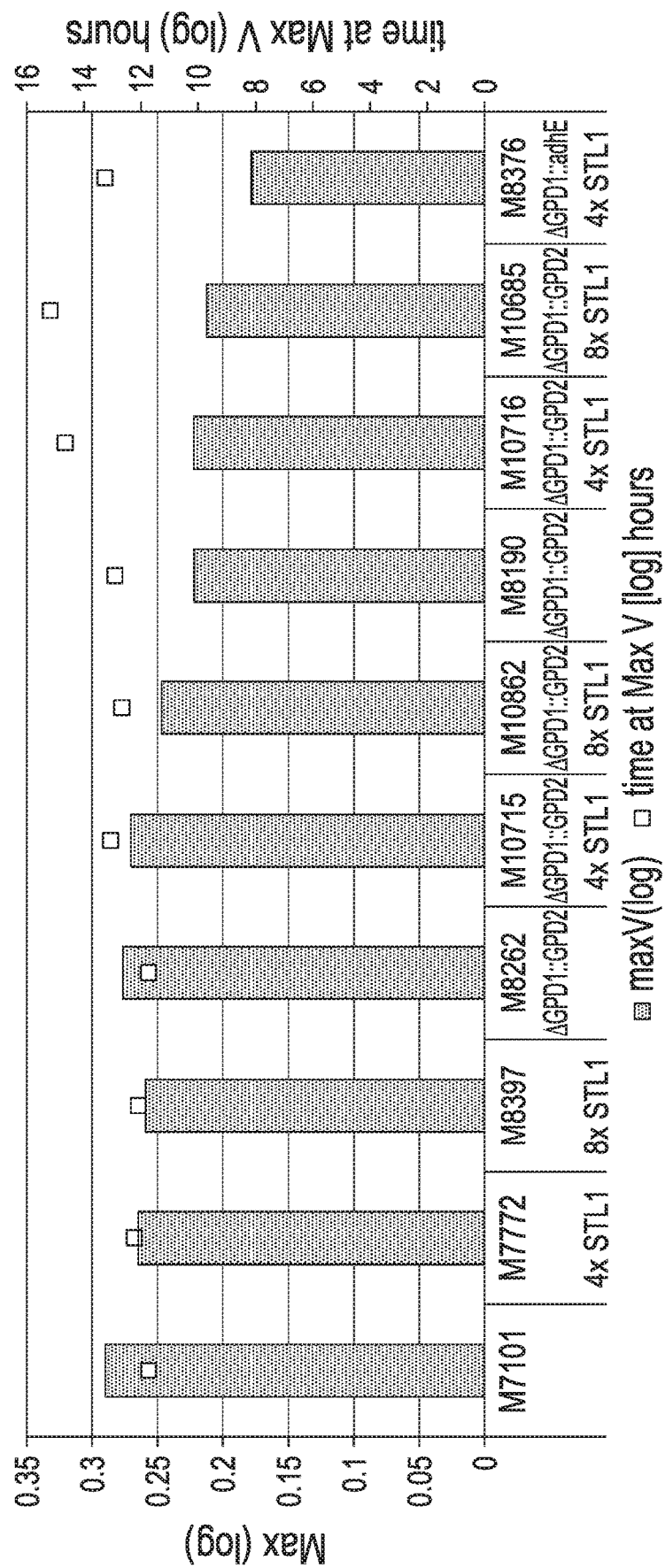
FIGS. 6A to 6E compare the growth rate, the percentage increase of ethanol yield, the percentage of glycerol reduction and the $CO_2$ off-gas rates for various strains bearing modifications in the GPD1 or the GPD2 gene.

Glycerol-3-phosphate dehydrogenase (GPD) knock-down strains M8262 and M8190 were created in order to maintain GPD activity from both the GPD1 and GPD2 promoter which differentially express GPD. Growth rates of these strains were compared to wild-type M7101 on YP medium supplemented with sucrose. Briefly, strain were pre-cultured on YP medium supplemented with sucrose and then were diluted into fresh YP medium supplemented with sucrose for anaerobic growth rate comparison. The optical density of the culture was monitored using a BIOTEK® plate reader and enabled the calculation of the maximum growth rate of the cultures as well as the time at which the maximum growth rate was reached. It was determined that deletion of GPD2 impaired growth (M8190) while deletion of GPD1 and expressing GPD2 from the GPD1 promoter (M8262) maintained a growth rate similar to wild-type M7101 (see FIG. 6A). STL1 overexpression had minimal effect on the growth rate (MaxV) of the GPD knockdown (FIG. 6A).

Figure 6B:
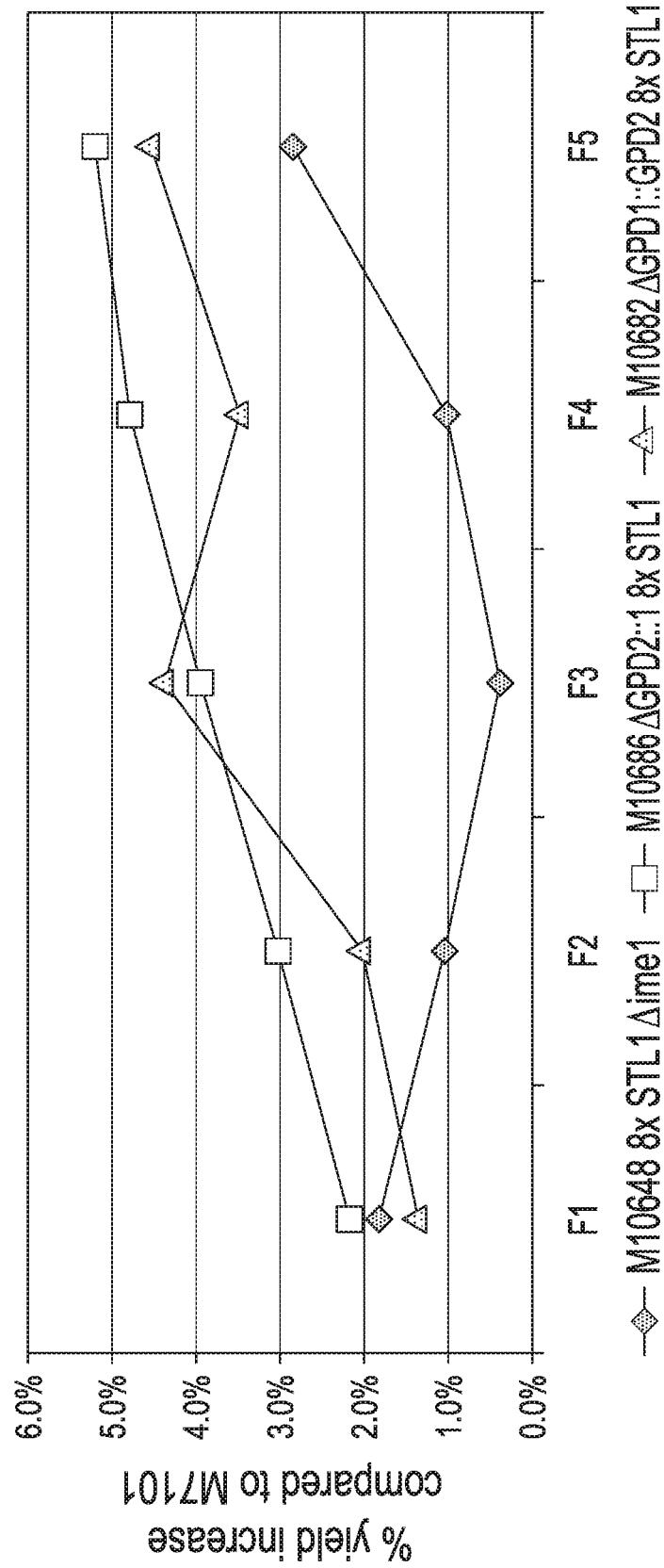
Figure 6C:
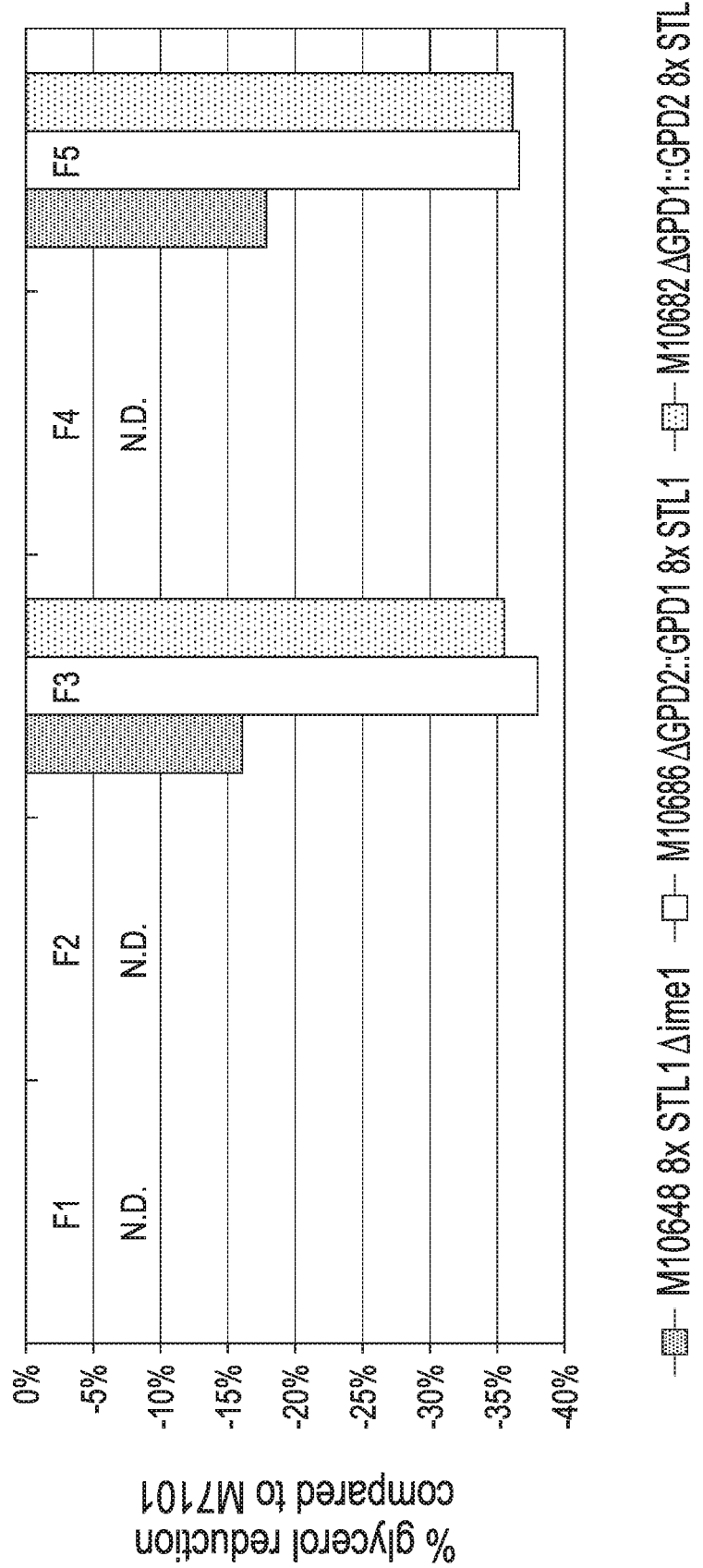
Figure 6D:
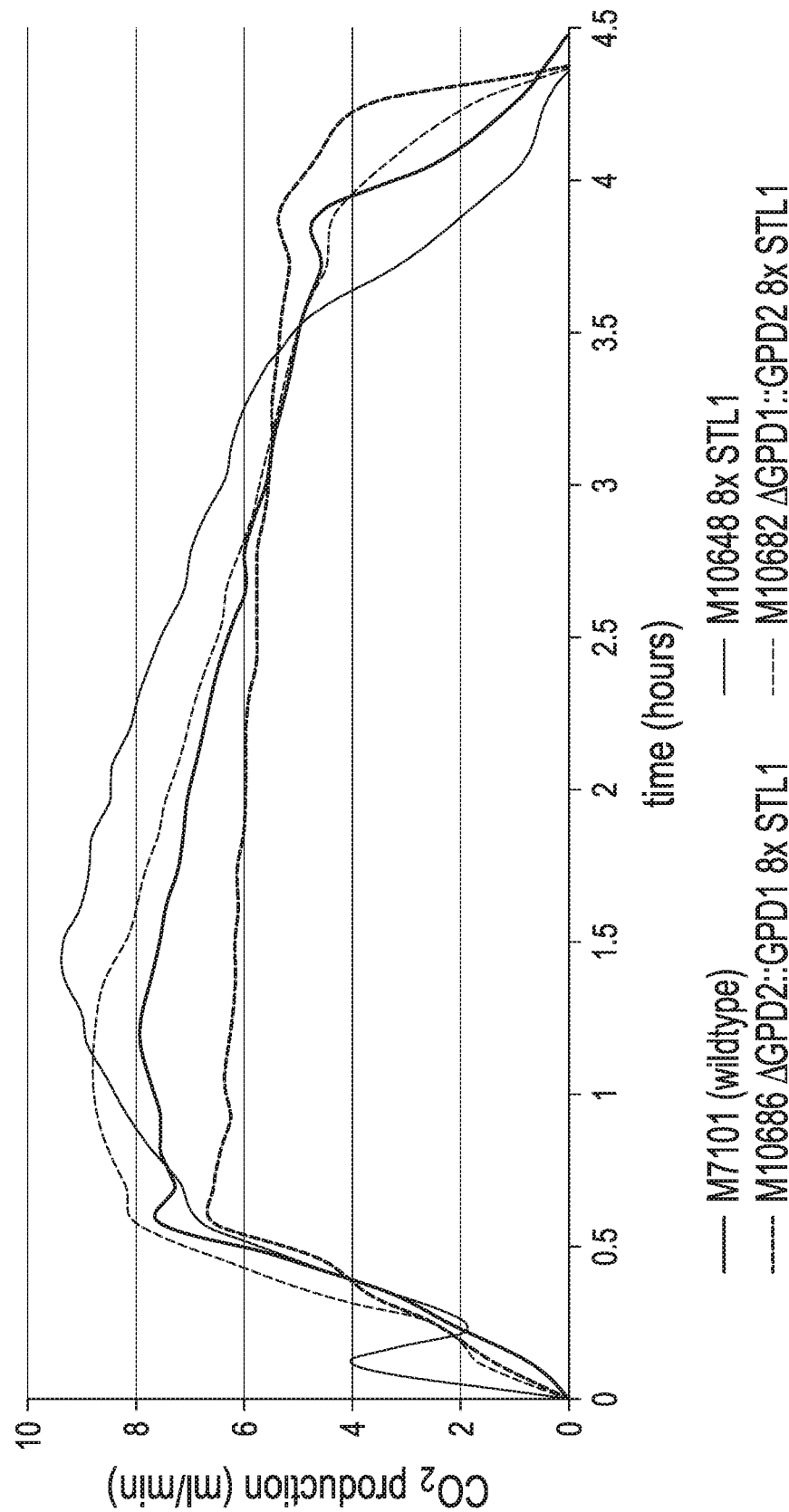
Figure 6E:
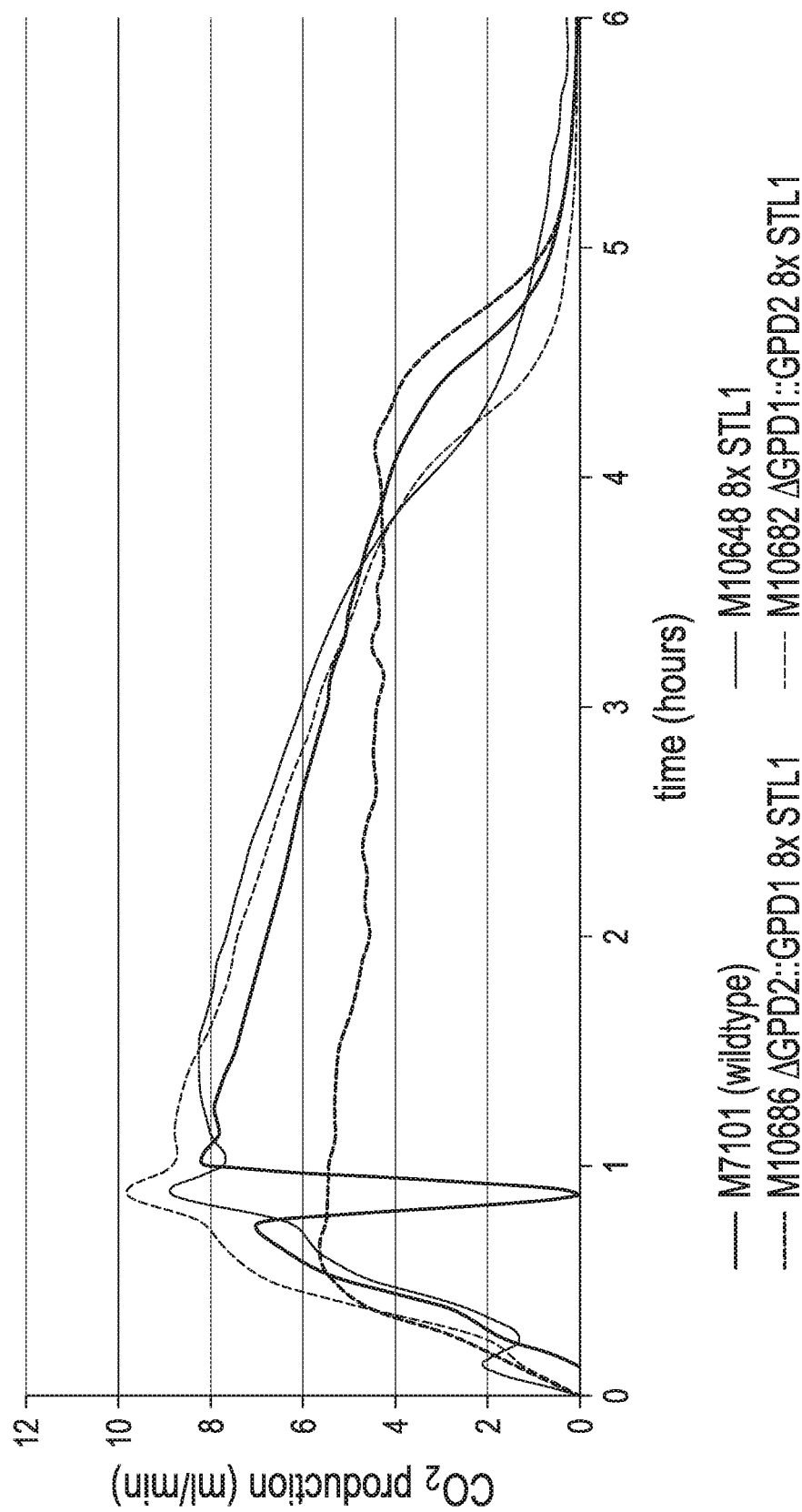

To further test the effect of the GPD knockdown with STL1, some of the stains were tested in the 50 mL lab scale system for five rounds of fermentation and acid treatment as explained in Example I. Fermentation ethanol yields, glycerol reduction (measured by HPLC) and $CO_2$ production were measured and compared to wild-type M7101 in each fermentation. While strain M10686 had higher yields over the five cycles of fermentation (FIGS. 6B and 6C), the kinetics of this strain was slower than strain M10682 (FIGS. 6D and 6E).

FIGS. 4 and 5 provide the fermentation results for strain M10682 relative to the strains overexpressing the STL1 gene (strain M10753 and strain M10761). The results presented in FIGS. 4 and 5 show that modifying the GPD1 locus lead to further ethanol yield improvement and decreased glycerol production relative to STL1 overexpression alone. In addition, and surprisingly as shown on FIG. 5, the rate of fermentation of strain M10682 is practically identical to strains M7101, M10753 and M10761.

Example III—Comparison to Non-Genetically Modified Yeasts

Strain M10682 has been compared to a variety of yeast strains that are regularly in use in Brazil for the production of fuel alcohol. A description of the various strains used in this example is provided in Table 3.

TABLE 3

Description and Genotype of the Various Strains Used in this Example

| Name | Genotype |
|---|---|
| M7101 | Non genetically modified (wild-type) *Saccharomyces cerevisiae* |
| Cat-1 | Non genetically modified *Saccharomyces cerevisiae* used in the Brazilian ethanol industry that can be obtained from LNF Latino America |
| Mill 1 | Non genetically modified "wild" *Saccharomyces cerevisiae* obtained from an operating mill in Brazil |
| Mill 2 | Non genetically modified "wild" *Saccharomyces cerevisiae* obtained from an operating mill in Brazil |
| M10682 | Δ ime1::STL1 (4x) <br> Δ fcy1::STL1 (4x) <br> Δ gpd1::GDP2 |

Figure 7A:
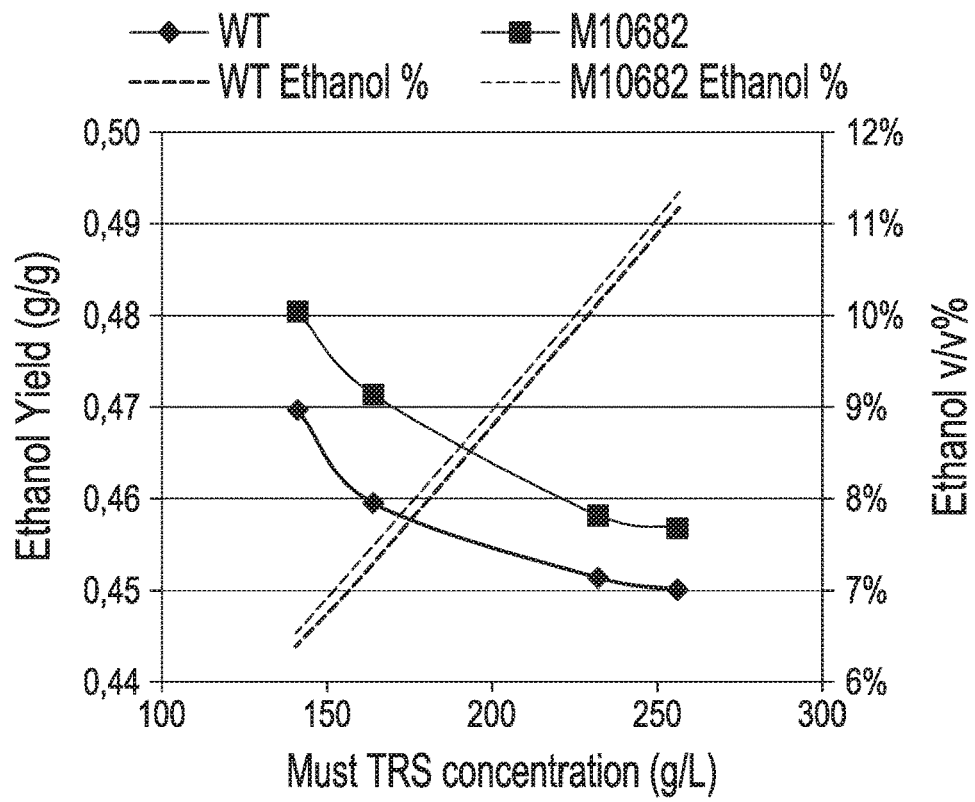
FIGS. 7A to 7C compares the robustness of strain M10682 to strain M7101 in increasing sugar concentration and in the presence of bacterial contamination. In (FIG. 7A), results are shown as the ethanol yield (g/g, left axis, M7101 (■), M10682 (♦)) or ethanol titer (v/v, right axis, M7101: dark dashed line, M10682: light dashed line) for strains cultured in increasing amount of must total reducing sugar concentration (g/L). In (FIG. 7B), the results are provided as the percentage of ethanol yield increase when compared to the M7101 strain in the absence of bacterial contamination (control), the presence of a contamination of $10^8$ bacterial cells or the presence of a contamination of $10^9$ bacterial cells. In (FIG. 7C), the results are shown as the $CO_2$ off-gas rates (provided as mL/min) in function of time (hours) for strain M7101 in the absence (dark solid line) or presence (dark dashed line) of a bacterial contamination ($10^9$ bacterial cells) and for strain M10682 in the absence (light solid line) or presence (light dashed line) of a bacterial contamination ($10^9$ bacterial cells). See Example III for a description of the various strains used.
Figure 7B:
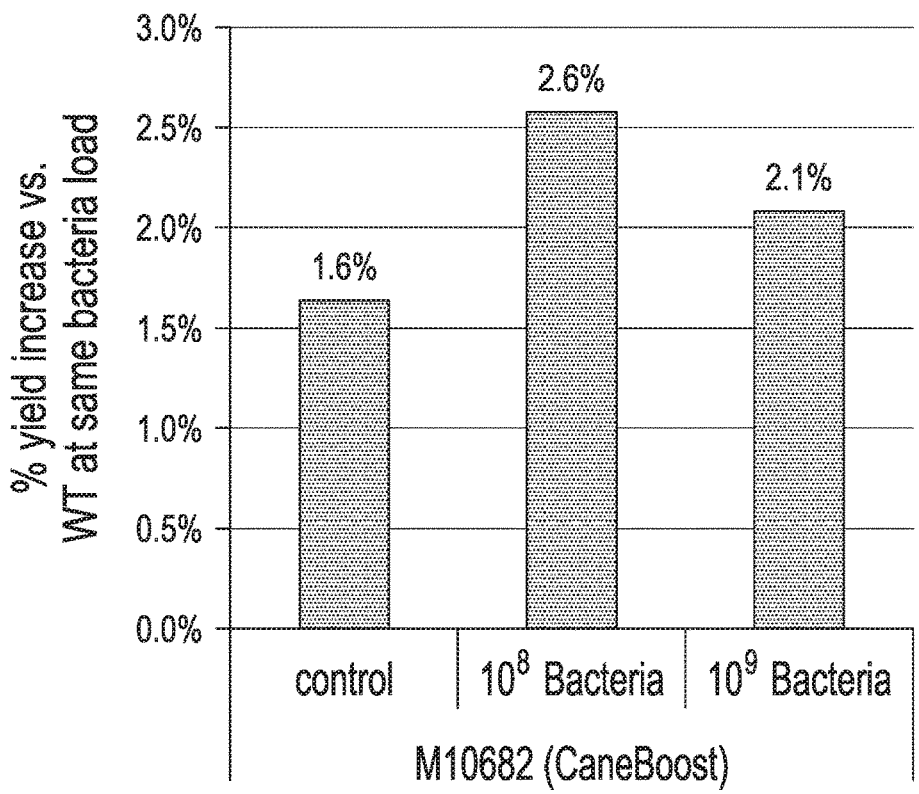
Figure 7C:
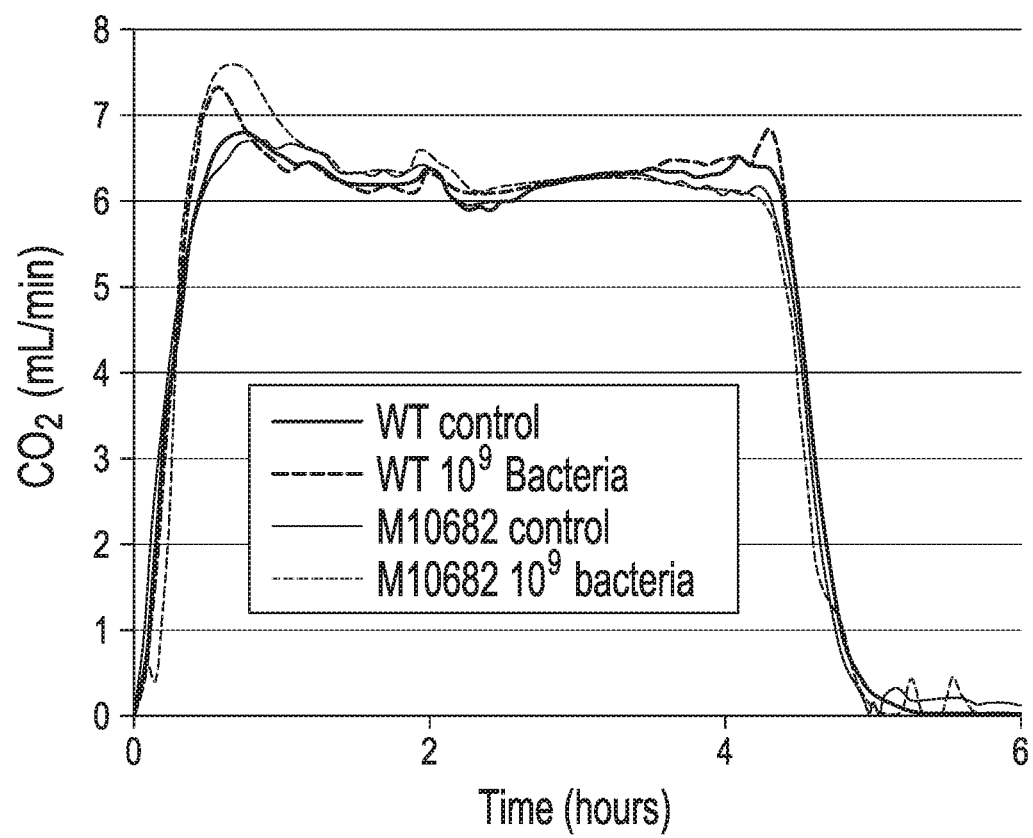

First, strain M10682 has been compared to a wild-type strain (M7101) over various stressful conditions to test its robustness. Strain M10682 and strain M7101 were run in parallel temperature/acid/sugar treatments and fermentations on the same must fed under standard conditions. Briefly, the strains were compared in a lab scale (50 mL) system over several fermentation cycles. Strains were run in duplicate reactors on Brazil sourced must. For the sugar stress testing (FIG. 7A), both strains were tested at various must total reducing sugars to produce fermentations creating between 7-11% v/v ethanol and reported as the average of nine consecutive rounds of fermentation and acid washing at each sugar concentration. For the bacterial contamination stress testing (FIGS. 7B and 7C), a mix of four different species of bacteria (*Lactobacillus fermentum* (39% of inoculum), *Lactobacillus reuteri* (29% of inoculum), *Weissella* sp. (27% of inoculum) and *Lactobacillus farraginis* (6% of inoculum)) was used to inoculate the challenged reactors at $10^8$ or $10^9$ bacterial cells/mL. The average ethanol and glycerol titers from the end of the fermentations was measured by HPLC and the $CO_2$ production rate was measured as indicated in Example I. The performance of strain M10682 relative to the performance of strain M7101 was assessed under temperature stress (39° C.) (Table 4), weak acid stress (Table 5), a range of total sugars loadings (FIG. 7A) and bacterial contamination challenge (FIGS. 7B and 7C).

TABLE 4

Comparison of the Robustness of Strain M10682 and Strain M7101 at Elevated Temperatures

| Strain | Temp. | Avg. Ethanol (g/l) | Yield Increase % | Avg. Glyc. (g/l) | Glycerol Reduction % | Avg. Viability Drop per fermentation |
|---|---|---|---|---|---|---|
| M7101 | 33° C. | 66.70 | | 3.50 | | 0.0% |
| | 39° C. | 67.38 | | 3.95 | | 3.6% |
| M10682 | 33° C. | 67.88 | 1.8% | 2.55 | −27.3% | 0.2% |
| | 39° C. | 67.96 | 0.8% | 3.11 | −21.1% | 4.7% |

TABLE 5

Comparison of the Robustness of Strain M10682 and Strain M7101 in Acidic Stress Conditions (at 33° C.)

| Strain | Acid Condition | Avg. Ethanol (g/l) | Yield Increase % | Avg. Glyc. (g/l) | Glycerol Reduction % | Avg. Biomass Production (g) | Avg Viability Drop per fermentation |
|---|---|---|---|---|---|---|---|
| M7101 | Control | 67.16 | | 3.41 | | 0.84 | 0.7% |
| | Low Acid* | 69.24 | | 2.28 | | 0.62 | 1.3% |
| | High Acid^ | 70.41 | | 2.86 | | 0.65 | 5.5% |
| M10682 | Control | 68.54 | 2.1% | 2.51 | −26.5% | 0.78 | 0.4% |
| | Low Acid* | 70.69 | 2.1% | 2.11 | −7.4% | 0.56 | 1.9% |
| | High Acid^ | 70.98 | 0.8% | 2.22 | −22.4% | 0.53 | 1.2% |

*Low acid conditions contain 2.5 g/L lactic acid and 2.5 g/: acetic acid
^High acid conditions contain 5 g/L lactic acid and 5 g/L acetic acid In the various stress tests the robustness of strain M10682 was equal or better than the baseline strain M7101. In addition, over all of the conditions tested, strain M10682 provided an ethanol yield increase compared to the baseline strain M7101.

Second, strain M10682 was further compared to other yeast strains. Strains M7101 and CAT-1 are often included either individually or together with other strains to start the crushing season, and then recycled for the entire crushing season (~200 days). This means that the populations of non-genetically-modified yeast undergo changes throughout the season, which can include adaptation via epigenetic modifications, genetic modifications, and/or displacement of the starting strains with strains originating with the fed must or molasses (i.e. "wild" yeast strains). In order to compare populations of yeast that have been adapted and/or changed during operations of mills, samples (referred to as "Mill 1" and "Mill 2") of operating sugarcane facilities in Brazil were obtained on a regular basis throughout their crushing season, and the yeast populations present in their process were used as a basis of comparison. Mill 1 and Mill 2 were both inoculated with a mixture of M7101 and CAT-1 at the beginning of the season, and so pure versions of M7101 and CAT-1 were included as controls.

Strains M7101 and M10682 were placed into four separate 50 mL reactors each (quadruplicate), while strain CAT-1 and samples Mill 1, and Mill 2 were placed into two separate 50 mL reactors each (duplicate). The strains and samples were put through twelve fermentations and acid wash cycles. The data obtained from the first three fermentations was not used as the mill yeast samples had not adjusted to conditions after being stored and shipped and so were leaving sugars behind during fermentation. After the initial three adjustment fermentations, data from the subsequent nine fermentations (36 data points each for strains M7101 and M10682, 18 data points each for strain CAT-1 and samples Mill 1, and Mill 2) were averaged to compare ethanol production yields.

Figure 8:
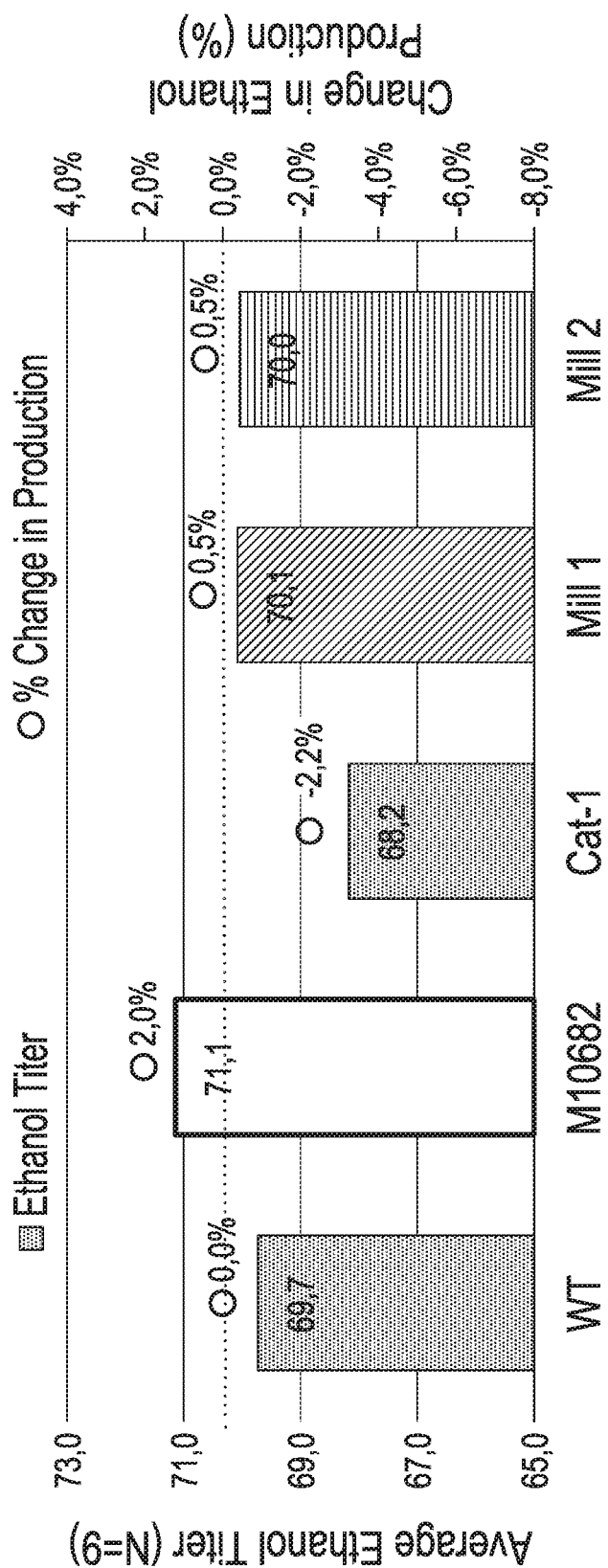
FIG. 8 compares ethanol production from sugarcane must fermentations using a recombinant yeast host strain (M10682) and yeast strains from the Brazilian ethanol industry (Cat-1, Mill 1 and Mill 2). Results are provided as the average ethanol titer (measured as g/L, left axis and bars)

FIG. 8 provides the results of the comparison for ethanol production. The average titer for strain M10682 was more than 1 gram per liter higher than that of all the other samples, or ~2% higher than the titer obtained from strain M7101. In addition, the performance of M7101 and the samples from the two Mills was nearly identical, showing how the ethanol yield performance of strains that have been used throughout the season is very close to that of the pure strain that producers use to begin their season.

FIG. 9 provides the results for the comparison of glycerol production during fermentation. The average titer of glycerol for strain M10682 was 0.9 g/L less than strain M7101, or 23% lower. In addition, the production of glycerol by strain M7101 and the samples from the two mills was nearly identical, again demonstrating that these samples perform very similarly to pure cultures the seasons are started with.

As indicated above, in Brazil, yeast strain populations in operating commercial facilities are not pure cultures. This is due in part to contamination of the population from "wild" yeast entering the fermentation, in part because of the evolution of the original population present in the fermenter, and in part because it is common practice to include more than one yeast strain as an inoculant at the beginning of the crushing season. Therefore, the ability of strain M10682 to perform in the presence wild yeasts was further examined.

In order to do so, fermentations were carried out as indicated in Example I, except that additional fermentations were added (in duplicate) to test the performance of a mixture of M10682 with the yeast sample from Mill 1 and from Mill 2. As above, both the average titers for the experiment (18 or 36 individual data points) and the percentage change compared to strain M7101 were reported. A 50/50 mixture of the yeast strains on a wet basis was measured and calculated.

The results of FIGS. 10 and 11 show, under the fermentation conditions used, a striking and surprising synergism between M10682 and the mill yeast samples. Where a pure culture of M10682 provides a 2% ethanol yield increase relative to M7101, and the mill yeast an ~0.5% increase, the 50/50 mixtures provide an almost 4% yield increase. This is matched by a reduction in glycerol production that is about the same for the mixtures as compared to pure cultures of M10682 even though only 50% of the population is comprised of M10682.

In addition to the synergy observed in terms of yield of ethanol production, the data gathered also showed a clear synergy of M10682 and mill yeast samples in terms of the rate of fermentation. FIG. 11 presents fermentation off-gas rates for the 11$^{th}$ round of fermentation during the test fermentation, and was typical of all the fermentation rate data. Data is shown for strain M10682, yeast samples from Mill 1, and the mixture of the two. The mixture of strain M10682 with the yeast sample from Mill 1 produced the fastest fermentation, finishing about an hour faster than either strain M10682 or the yeast sample Mill 1 alone, which is a 17% increase in productivity.

While the invention has been described in connection with specific embodiments thereof, it will be understood that the scope of the claims should not be limited by the preferred embodiments set forth in the examples, but should be given the broadest interpretation consistent with the description as a whole.

REFERENCES

U.S. Pat. No. 8,956,851
U.S. Patent Application Publication No. 2011/0189744
U.S. Patent Application Publication No. 2011/0312054
U.S. Patent Application Publication No. 2012/0003701
International Publication No. WO 2009/138877
International Publication No. WO 2010/056805
International Publication No. WO 2010/060056
International Publication No. WO 2010/075529
International Publication No. WO 2011/153516
International Publication No. WO 2012/138942
International Publication No. WO 2015/023989
International Publication No. WO 2017/037614
Argueso J L, Carazzolle M F, Mieczkowski P A, Duarte F M, Netto O V, Missawa S K, Galzerani F, Costa G G, Vidal R O, Noronha M F, Dominska M, Andrietta M G, Andrietta S R, Cunha A F, Gomes L H, Tavares F C, Alcarde A R, Dietrich F S, McCusker J H, Petes T D, Pereira G A. Genome structure of a *Saccharomyces cerevisiae* strain widely used in bioethanol production. *Genome Res.* 2009 December; 19(12):2258-70.
Wang J, Liu W, Ding W, Zhang G, Liu J. Increasing ethanol titer and yield in a gpd1Δ gpd2Δ strain by simultaneous overexpression of GLT1 and STL1 in *Saccharomyces cerevisiae*. *Biotechnol Lett.* 2013 November; 35(11): 1859-64.

What is claimed is:

1. A recombinant yeast host cell:
   a) comprising a first genetic modification for expressing, in glycolytic conditions, a heterologous glycerol proton symporter STL1 protein;
   b) comprising a second genetic modification for inactivating a native NAD-dependent glycerol-3-phosphate dehydrogenase (GPD) protein, wherein the native GPD protein is GPD1; and
   c) comprising a third genetic modification for expressing, in high osmotic conditions, a heterologous NAD-dependent glycerol-3-phosphate dehydrogenase (GPD) protein, wherein the heterologous GPD protein is GPD2;

wherein the recombinant yeast host cell is from the genus *Saccharomyces* sp.; and wherein the recombinant yeast host cell produces more ethanol and a reduced level of glycerol when compared to a wild-type host cell.

2. The recombinant yeast host cell of claim 1, further comprising a native GPD2 protein expressed from a native GPD2 gene under the control of a native GPD2 promoter.

3. The recombinant yeast host cell of claim 1, wherein the first genetic modification comprises introducing a first heterologous nucleic acid molecule in the recombinant yeast host cell and wherein the first heterologous nucleic acid molecule comprises a first polynucleotide encoding the STL1 protein and a second polynucleotide encoding a glycolytic promoter operably linked to the first polynucleotide.

4. The recombinant yeast host cell of claim 3, wherein the glycolytic promoter comprises one or more of a promoter from a ADH1 gene, a PGI1 gene, a PFK1 gene, a PFK2 gene, a FBA1 gene, a TPI1 gene, a TDH1 gene, a TDH2 gene, a TDH3 gene, a PGK1 gene, a GPM1 gene, a ENO1 gene, a ENO2 gene, a PYK2 gene or a CDC19 gene.

5. The recombinant yeast host cell of claim 3, wherein the glycolytic promoter is a constitutive promoter.

6. The recombinant yeast host cell of claim 3, wherein the recombinant yeast host cell comprises 2, 4, 6 or 8 copies of the first heterologous nucleic acid molecule.

7. The recombinant yeast host cell of claim 1, wherein the second genetic modification comprises deleting the native glycerol-3-phosphate dehydrogenase-1 (GPD1) protein.

8. The recombinant yeast host cell of claim 1, wherein the third genetic modification comprises introducing the heterologous nucleic acid molecule in the recombinant yeast host cell and wherein the heterologous nucleic acid molecule comprises a first polynucleotide encoding the heterologous GPD2 protein and a second polynucleotide encoding an osmotic promoter operably linked to the first polynucleotide encoding the heterologous GPD2 protein.

9. The recombinant yeast host cell of claim 8, wherein the osmotic promoter is one or more of a promoter from a GPD1 gene, a DAK1 gene or a TPS2 gene.

10. The recombinant yeast host cell of claim 1, wherein the recombinant yeast host cell is from the species *Saccharomyces cerevisiae*.

11. A process for making a fermentation product, the process comprising contacting (i) a first fermentation medium comprising a carbohydrate with (ii) the recombinant yeast host cell of claim 1 to obtain a first fermented medium under conditions to promote the production of the fermentation product.

12. The process of claim 11, wherein the fermentation medium comprises sugarcane, a sugarcane derivative, molasses and/or a molasses derivative.

13. The process of claim 11, wherein the fermentation product is ethanol.

14. The process of claim 11, further comprising at least one fermentation cycle comprising acid washing the recombinant yeast host cell present in the fermented medium to obtain an acid washed recombinant yeast host cell and contacting the acid washed recombinant yeast host cell with a second fermentation medium comprising a carbohydrate to obtain a second fermented medium under conditions to promote the production of the fermentation product.

15. The process of claim 14 further comprising at least two or more fermentation cycles.

16. A fermentation medium comprising the recombinant yeast host cell of claim 1.

17. The recombinant yeast host cell of claim 7, wherein second genetic modification comprises deleting at least one nucleotide of the gene encoding the native GPD1 protein.

* * * * *

SEQUENCE LISTING

```
<160> NUMBER OF SEQ ID NOS: 9

<210> SEQ ID NO 1
<211> LENGTH: 1707
<212> TYPE: DNA
<213> ORGANISM: Saccharomyces cerevisiae
<220> FEATURE:
<221> NAME/KEY: CDS
<222> LOCATION: (1)..(1707)

<400> SEQUENCE: 1 atg aag gat tta aaa tta tcg aat ttc aaa ggc aaa ttt ata agc aga        48
Met Lys Asp Leu Lys Leu Ser Asn Phe Lys Gly Lys Phe Ile Ser Arg
1               5                   10                  15 acc agt cac tgg gga ctt acg ggt aag aag ttg cgg tat ttc atc act        96
Thr Ser His Trp Gly Leu Thr Gly Lys Lys Leu Arg Tyr Phe Ile Thr
```

20                  25                  30
atc gca tct atg acg ggc ttc tcc ctg ttt gga tac gac caa ggg ttg        144
Ile Ala Ser Met Thr Gly Phe Ser Leu Phe Gly Tyr Asp Gln Gly Leu
         35                  40                  45 atg gca agt cta att act ggt aaa cag ttc aac tat gaa ttt cca gca        192
Met Ala Ser Leu Ile Thr Gly Lys Gln Phe Asn Tyr Glu Phe Pro Ala
 50                  55                  60 acc aaa gaa aat ggc gat cat gac aga cac gca act gta gtg cag ggc        240
Thr Lys Glu Asn Gly Asp His Asp Arg His Ala Thr Val Val Gln Gly
 65                  70                  75                  80 gct aca acc tcc tgt tat gaa tta ggt tgt ttc gca ggt tct cta ttc        288
Ala Thr Thr Ser Cys Tyr Glu Leu Gly Cys Phe Ala Gly Ser Leu Phe
                 85                  90                  95 gtt atg ttc tgc ggt gaa aga att ggt aga aaa cca tta atc ctg atg        336
Val Met Phe Cys Gly Glu Arg Ile Gly Arg Lys Pro Leu Ile Leu Met
            100                 105                 110 ggt tcc gta ata acc atc att ggt gcc gtt att tct aca tgc gca ttt        384
Gly Ser Val Ile Thr Ile Ile Gly Ala Val Ile Ser Thr Cys Ala Phe
        115                 120                 125 cgt ggt tac tgg gca tta ggc cag ttt atc atc gga aga gtc gtc act        432
Arg Gly Tyr Trp Ala Leu Gly Gln Phe Ile Ile Gly Arg Val Val Thr
130                 135                 140 ggt gtt gga aca ggg ttg aat aca tct act att ccc gtt tgg caa tca        480
Gly Val Gly Thr Gly Leu Asn Thr Ser Thr Ile Pro Val Trp Gln Ser
145                 150                 155                 160 gaa atg tca aaa gct gaa aat aga ggg ttg ctg gtc aat tta gaa ggt        528
Glu Met Ser Lys Ala Glu Asn Arg Gly Leu Leu Val Asn Leu Glu Gly
                165                 170                 175 tcc aca att gct ttt ggt act atg att gct tat tgg att gat ttt ggg        576
Ser Thr Ile Ala Phe Gly Thr Met Ile Ala Tyr Trp Ile Asp Phe Gly
            180                 185                 190 ttg tct tat acc aac agt tct gtt cag tgg aga ttc ccc gtg tca atg        624
Leu Ser Tyr Thr Asn Ser Ser Val Gln Trp Arg Phe Pro Val Ser Met
        195                 200                 205 caa atc gtt ttt gct ctc ttc ctg ctt gct ttc atg att aaa cta cct        672
Gln Ile Val Phe Ala Leu Phe Leu Leu Ala Phe Met Ile Lys Leu Pro
210                 215                 220 gaa tcg cca cgt tgg ctg att tct caa agt cga aca gaa gaa gct cgc        720
Glu Ser Pro Arg Trp Leu Ile Ser Gln Ser Arg Thr Glu Glu Ala Arg
225                 230                 235                 240 tac ttg gta gga aca cta gac gac gcg gat cca aat gat gag gaa gtt        768
Tyr Leu Val Gly Thr Leu Asp Asp Ala Asp Pro Asn Asp Glu Glu Val
                245                 250                 255 ata aca gaa gtt gct atg ctt cac gat gct gtt aac agg acc aaa cac        816
Ile Thr Glu Val Ala Met Leu His Asp Ala Val Asn Arg Thr Lys His
            260                 265                 270 gag aaa cat tca ctg tca agt ttg ttc tcc aga ggc agg tcc caa aat        864
Glu Lys His Ser Leu Ser Ser Leu Phe Ser Arg Gly Arg Ser Gln Asn
        275                 280                 285 ctt cag agg gct ttg att gca gct tca acg caa ttt ttc cag caa ttt        912
Leu Gln Arg Ala Leu Ile Ala Ala Ser Thr Gln Phe Phe Gln Gln Phe
290                 295                 300 act ggt tgt aac gct gcc ata tac tac tct act gta tta ttc aac aaa        960
Thr Gly Cys Asn Ala Ala Ile Tyr Tyr Ser Thr Val Leu Phe Asn Lys
305                 310                 315                 320 aca att aaa tta gac tat aga tta tca atg atc ata ggt ggg gtc ttc       1008
Thr Ile Lys Leu Asp Tyr Arg Leu Ser Met Ile Ile Gly Gly Val Phe
                325                 330                 335 gca aca atc tac gcc tta tct act att ggt tca ttt ttt cta att gaa       1056

```
Ala Thr Ile Tyr Ala Leu Ser Thr Ile Gly Ser Phe Phe Leu Ile Glu
                340                 345                 350 aag cta ggt aga cgt aag ctg ttt tta tta ggt gcc aca ggt caa gca    1104
Lys Leu Gly Arg Arg Lys Leu Phe Leu Leu Gly Ala Thr Gly Gln Ala
            355                 360                 365 gtt tca ttc aca att aca ttt gca tgc ttg gtc aaa gaa aat aaa gaa    1152
Val Ser Phe Thr Ile Thr Phe Ala Cys Leu Val Lys Glu Asn Lys Glu
    370                 375                 380 aac gca aga ggt gct gcc gtc ggc tta ttt ttg ttc att aca ttc ttt    1200
Asn Ala Arg Gly Ala Ala Val Gly Leu Phe Leu Phe Ile Thr Phe Phe
385                 390                 395                 400 ggt ttg tct ttg cta tca tta cca tgg ata tac cca cca gaa att gca    1248
Gly Leu Ser Leu Leu Ser Leu Pro Trp Ile Tyr Pro Pro Glu Ile Ala
                405                 410                 415 tca atg aaa gtt cgt gca tca aca aac gct ttc tcc aca tgt act aat    1296
Ser Met Lys Val Arg Ala Ser Thr Asn Ala Phe Ser Thr Cys Thr Asn
            420                 425                 430 tgg ttg tgt aac ttt gcg gtt gtc atg ttc acc cca ata ttt att gga    1344
Trp Leu Cys Asn Phe Ala Val Val Met Phe Thr Pro Ile Phe Ile Gly
    435                 440                 445 cag tcc ggt tgg ggt tgc tac tta ttt ttt gct gtt atg aat tat tta    1392
Gln Ser Gly Trp Gly Cys Tyr Leu Phe Phe Ala Val Met Asn Tyr Leu
450                 455                 460 tac att cca gtt atc ttc ttt ttc tac cct gaa acc gcc gga aga agt    1440
Tyr Ile Pro Val Ile Phe Phe Phe Tyr Pro Glu Thr Ala Gly Arg Ser
465                 470                 475                 480 ttg gag gaa atc gac atc atc ttt gct aaa gca tac gag gat ggc act    1488
Leu Glu Glu Ile Asp Ile Ile Phe Ala Lys Ala Tyr Glu Asp Gly Thr
                485                 490                 495 caa cca tgg aga gtt gct aac cat ttg ccc aag tta tcc cta caa gaa    1536
Gln Pro Trp Arg Val Ala Asn His Leu Pro Lys Leu Ser Leu Gln Glu
            500                 505                 510 gtc gaa gat cat gcc aat gca ttg ggc tct tat gac gac gaa atg gaa    1584
Val Glu Asp His Ala Asn Ala Leu Gly Ser Tyr Asp Asp Glu Met Glu
    515                 520                 525 aaa gag gac ttt ggt gaa gat aga gta gaa gac acc tat aac caa att    1632
Lys Glu Asp Phe Gly Glu Asp Arg Val Glu Asp Thr Tyr Asn Gln Ile
530                 535                 540 aac ggc gat aat tcg tct agt tct tca aac atc aaa aat gaa gat aca    1680
Asn Gly Asp Asn Ser Ser Ser Ser Asn Ile Lys Asn Glu Asp Thr
545                 550                 555                 560 gtg aac gat aaa gca aat ttt gag ggt                                1707
Val Asn Asp Lys Ala Asn Phe Glu Gly
                565

<210> SEQ ID NO 2
<211> LENGTH: 569
<212> TYPE: PRT
<213> ORGANISM: Saccharomyces cerevisiae

<400> SEQUENCE: 2

Met Lys Asp Leu Lys Leu Ser Asn Phe Lys Gly Lys Phe Ile Ser Arg
1               5                   10                  15

Thr Ser His Trp Gly Leu Thr Gly Lys Lys Leu Arg Tyr Phe Ile Thr
                20                  25                  30

Ile Ala Ser Met Thr Gly Phe Ser Leu Phe Gly Tyr Asp Gln Gly Leu
            35                  40                  45

Met Ala Ser Leu Ile Thr Gly Lys Gln Phe Asn Tyr Glu Phe Pro Ala
        50                  55                  60
```

```
Thr Lys Glu Asn Gly Asp His Asp Arg His Ala Thr Val Val Gln Gly
 65                  70                  75                  80

Ala Thr Thr Ser Cys Tyr Glu Leu Gly Cys Phe Ala Gly Ser Leu Phe
                 85                  90                  95

Val Met Phe Cys Gly Glu Arg Ile Gly Arg Lys Pro Leu Ile Leu Met
             100                 105                 110

Gly Ser Val Ile Thr Ile Ile Gly Ala Val Ile Ser Thr Cys Ala Phe
         115                 120                 125

Arg Gly Tyr Trp Ala Leu Gly Gln Phe Ile Ile Gly Arg Val Val Thr
     130                 135                 140

Gly Val Gly Thr Gly Leu Asn Thr Ser Thr Ile Pro Val Trp Gln Ser
145                 150                 155                 160

Glu Met Ser Lys Ala Glu Asn Arg Gly Leu Leu Val Asn Leu Glu Gly
                 165                 170                 175

Ser Thr Ile Ala Phe Gly Thr Met Ile Ala Tyr Trp Ile Asp Phe Gly
             180                 185                 190

Leu Ser Tyr Thr Asn Ser Ser Val Gln Trp Arg Phe Pro Val Ser Met
         195                 200                 205

Gln Ile Val Phe Ala Leu Phe Leu Leu Ala Phe Met Ile Lys Leu Pro
     210                 215                 220

Glu Ser Pro Arg Trp Leu Ile Ser Gln Ser Arg Thr Glu Glu Ala Arg
225                 230                 235                 240

Tyr Leu Val Gly Thr Leu Asp Asp Ala Asp Pro Asn Asp Glu Glu Val
                 245                 250                 255

Ile Thr Glu Val Ala Met Leu His Asp Ala Val Asn Arg Thr Lys His
             260                 265                 270

Glu Lys His Ser Leu Ser Ser Leu Phe Ser Arg Gly Arg Ser Gln Asn
         275                 280                 285

Leu Gln Arg Ala Leu Ile Ala Ala Ser Thr Gln Phe Phe Gln Gln Phe
     290                 295                 300

Thr Gly Cys Asn Ala Ala Ile Tyr Tyr Ser Thr Val Leu Phe Asn Lys
305                 310                 315                 320

Thr Ile Lys Leu Asp Tyr Arg Leu Ser Met Ile Ile Gly Gly Val Phe
                 325                 330                 335

Ala Thr Ile Tyr Ala Leu Ser Thr Ile Gly Ser Phe Phe Leu Ile Glu
             340                 345                 350

Lys Leu Gly Arg Arg Lys Leu Phe Leu Leu Gly Ala Thr Gly Gln Ala
         355                 360                 365

Val Ser Phe Thr Ile Thr Phe Ala Cys Leu Val Lys Glu Asn Lys Glu
     370                 375                 380

Asn Ala Arg Gly Ala Ala Val Gly Leu Phe Leu Phe Ile Thr Phe Phe
385                 390                 395                 400

Gly Leu Ser Leu Leu Ser Leu Pro Trp Ile Tyr Pro Pro Glu Ile Ala
                 405                 410                 415

Ser Met Lys Val Arg Ala Ser Thr Asn Ala Phe Ser Cys Thr Asn
             420                 425                 430

Trp Leu Cys Asn Phe Ala Val Val Met Phe Thr Pro Ile Phe Ile Gly
         435                 440                 445

Gln Ser Gly Trp Gly Cys Tyr Leu Phe Phe Ala Val Met Asn Tyr Leu
     450                 455                 460

Tyr Ile Pro Val Ile Phe Phe Tyr Pro Glu Thr Ala Gly Arg Ser
465                 470                 475                 480

Leu Glu Glu Ile Asp Ile Ile Phe Ala Lys Ala Tyr Glu Asp Gly Thr
```

```
                      485                 490                 495
Gln Pro Trp Arg Val Ala Asn His Leu Pro Lys Leu Ser Leu Gln Glu
            500                 505                 510

Val Glu Asp His Ala Asn Ala Leu Gly Ser Tyr Asp Asp Glu Met Glu
            515                 520                 525

Lys Glu Asp Phe Gly Glu Asp Arg Val Glu Asp Thr Tyr Asn Gln Ile
        530                 535                 540

Asn Gly Asp Asn Ser Ser Ser Ser Asn Ile Lys Asn Glu Asp Thr
545                 550                 555                 560

Val Asn Asp Lys Ala Asn Phe Glu Gly
                565

<210> SEQ ID NO 3
<211> LENGTH: 1641
<212> TYPE: DNA
<213> ORGANISM: Candida albicans
<220> FEATURE:
<221> NAME/KEY: CDS
<222> LOCATION: (1)..(1641)

<400> SEQUENCE: 3 atg ggt ggg ttc ata gat aat att ttc aaa aga acc aca act gct gga        48
Met Gly Gly Phe Ile Asp Asn Ile Phe Lys Arg Thr Thr Thr Ala Gly
1               5                   10                  15 tta act ggt aga aaa tta cgt gca gca gtc act att act gcc aca ctt       96
Leu Thr Gly Arg Lys Leu Arg Ala Ala Val Thr Ile Thr Ala Thr Leu
            20                  25                  30 ggg ttt tca ctt ttc gga tat gat caa ggt tta atg gcc gga tta att      144
Gly Phe Ser Leu Phe Gly Tyr Asp Gln Gly Leu Met Ala Gly Leu Ile
        35                  40                  45 tct gcc gaa caa ttc aat tgg gaa ttc cct gct act aaa gat aat agt      192
Ser Ala Glu Gln Phe Asn Trp Glu Phe Pro Ala Thr Lys Asp Asn Ser
    50                  55                  60 gtt atc caa ggt gct gtt act gca tct tat gaa ttg gga tgt ttc ttt      240
Val Ile Gln Gly Ala Val Thr Ala Ser Tyr Glu Leu Gly Cys Phe Phe
65                  70                  75                  80 ggt gct att ttt gct tta ctt aga ggt gat gct tta ggt aga aaa cca      288
Gly Ala Ile Phe Ala Leu Leu Arg Gly Asp Ala Leu Gly Arg Lys Pro
                85                  90                  95 att att ttc ttt ggt gct act att att att ctt ggt aca att att tcc      336
Ile Ile Phe Phe Gly Ala Thr Ile Ile Ile Leu Gly Thr Ile Ile Ser
            100                 105                 110 gtt act cca ttt aga cca cat tgg cca tta ggt caa ttt gtg gtt ggt      384
Val Thr Pro Phe Arg Pro His Trp Pro Leu Gly Gln Phe Val Val Gly
        115                 120                 125 aga gtc atc act ggt att ggt aat ggt atg aat act gct act att cca      432
Arg Val Ile Thr Gly Ile Gly Asn Gly Met Asn Thr Ala Thr Ile Pro
    130                 135                 140 gtg tgg caa tca gaa atg tca aaa cca gaa aat aga ggt aaa ttg gtc      480
Val Trp Gln Ser Glu Met Ser Lys Pro Glu Asn Arg Gly Lys Leu Val
145                 150                 155                 160 aat tta gaa ggt gcc gtt gtg gca ttt ggt act ttt att gct tat tgg      528
Asn Leu Glu Gly Ala Val Val Ala Phe Gly Thr Phe Ile Ala Tyr Trp
                165                 170                 175 tta gat ttt ggg tta tct tat gtt gat tct tca gtt tct tgg aga ttc      576
Leu Asp Phe Gly Leu Ser Tyr Val Asp Ser Ser Val Ser Trp Arg Phe
            180                 185                 190 cca gtt gct ttc caa att ttc ttt gcc tta tgg gtt att ttt gga att      624
Pro Val Ala Phe Gln Ile Phe Phe Ala Leu Trp Val Ile Phe Gly Ile
        195                 200                 205
```

```
att caa tta cct gaa tct cct cgt tgg ttg att tct aaa gat aga aaa    672
Ile Gln Leu Pro Glu Ser Pro Arg Trp Leu Ile Ser Lys Asp Arg Lys
    210             215                 220 cca gaa gct ttt gaa gtc tta gct gct tta aat gat act act cca gat    720
Pro Glu Ala Phe Glu Val Leu Ala Ala Leu Asn Asp Thr Thr Pro Asp
225             230                 235                 240 gat gat gct att gtt gct gaa gct agt gtt att att gac gcc gtt aga    768
Asp Asp Ala Ile Val Ala Glu Ala Ser Val Ile Ile Asp Ala Val Arg
                245                 250                 255 aga aac gct aaa gtc caa gct ggt ttc aaa gat ttg ttt act ggt ggt    816
Arg Asn Ala Lys Val Gln Ala Gly Phe Lys Asp Leu Phe Thr Gly Gly
            260                 265                 270 aaa act gct cat ttc caa aga atg ctt att ggg tca tca acc caa ttt    864
Lys Thr Ala His Phe Gln Arg Met Leu Ile Gly Ser Ser Thr Gln Phe
        275                 280                 285 ttc caa caa ttc act ggt tgt aat gca gct att tat tat tcc act tta    912
Phe Gln Gln Phe Thr Gly Cys Asn Ala Ala Ile Tyr Tyr Ser Thr Leu
    290                 295                 300 ttg ttc tac gaa acc gtt ttc cat cat act aaa tac cgt tta tca atg    960
Leu Phe Tyr Glu Thr Val Phe His His Thr Lys Tyr Arg Leu Ser Met
305             310                 315                 320 att ttg ggt ggg gtg ttt gct act att tat gct tta gcc act ctt cca    1008
Ile Leu Gly Gly Val Phe Ala Thr Ile Tyr Ala Leu Ala Thr Leu Pro
                325                 330                 335 tca ttc ttt tta att gat act ttg ggt aga aga aat ttg ttt tta att    1056
Ser Phe Phe Leu Ile Asp Thr Leu Gly Arg Arg Asn Leu Phe Leu Ile
            340                 345                 350 ggt gca att ggt caa ggg att tca ttc ctt att tca ttt gct tgt ttg    1104
Gly Ala Ile Gly Gln Gly Ile Ser Phe Leu Ile Ser Phe Ala Cys Leu
        355                 360                 365 att aac cca act gaa caa aat gct aaa ggt gct gcc gtt ggt att tat    1152
Ile Asn Pro Thr Glu Gln Asn Ala Lys Gly Ala Ala Val Gly Ile Tyr
    370                 375                 380 ttg ttt att gtt ttc ttt gcc ttc acc att tta cca tta cca tgg att    1200
Leu Phe Ile Val Phe Phe Ala Phe Thr Ile Leu Pro Leu Pro Trp Ile
385             390                 395                 400 tac cca cca gaa att aat cca tta aga aca aga act act gct tct gcc    1248
Tyr Pro Pro Glu Ile Asn Pro Leu Arg Thr Arg Thr Thr Ala Ser Ala
                405                 410                 415 gtc tcc act tgt acc aat tgg tta acc aat ttc gcc gtt gtt atg ttt    1296
Val Ser Thr Cys Thr Asn Trp Leu Thr Asn Phe Ala Val Val Met Phe
            420                 425                 430 act cca cca ttt att tct gct agt ggt tgg ggt tgt tat ctt tat ttt    1344
Thr Pro Pro Phe Ile Ser Ala Ser Gly Trp Gly Cys Tyr Leu Tyr Phe
        435                 440                 445 gcc gtt atg aat ttc ttg ttt gtt cca atc atc ttt ttc ttt tat cca    1392
Ala Val Met Asn Phe Leu Phe Val Pro Ile Ile Phe Phe Phe Tyr Pro
    450                 455                 460 gaa act gct ggt aga tca tta gaa gaa att gat att att ttc gct aaa    1440
Glu Thr Ala Gly Arg Ser Leu Glu Glu Ile Asp Ile Ile Phe Ala Lys
465             470                 475                 480 gct tac gtt gaa aaa aga caa cca tgg aga gtt gct gct act tta cca    1488
Ala Tyr Val Glu Lys Arg Gln Pro Trp Arg Val Ala Ala Thr Leu Pro
                485                 490                 495 aaa tta tca tta caa gaa gtt gaa gat gaa tct aaa agc ttg ggt ctt    1536
Lys Leu Ser Leu Gln Glu Val Glu Asp Glu Ser Lys Ser Leu Gly Leu
            500                 505                 510 tat gat gat gat ttc gaa aaa gat aat ttc gaa act aaa gaa gat att    1584
Tyr Asp Asp Asp Phe Glu Lys Asp Asn Phe Glu Thr Lys Glu Asp Ile
```

-continued

```
              515                 520                 525
tct gat ggt act gcc tca aac agt aat ggt gtt ttt gaa aaa cca gaa    1632
Ser Asp Gly Thr Ala Ser Asn Ser Asn Gly Val Phe Glu Lys Pro Glu
530                 535                 540 aat gtt taa                                                        1641
Asn Val
545

<210> SEQ ID NO 4
<211> LENGTH: 546
<212> TYPE: PRT
<213> ORGANISM: Candida albicans

<400> SEQUENCE: 4

Met Gly Gly Phe Ile Asp Asn Ile Phe Lys Arg Thr Thr Thr Ala Gly
1               5                   10                  15

Leu Thr Gly Arg Lys Leu Arg Ala Ala Val Thr Ile Thr Ala Thr Leu
            20                  25                  30

Gly Phe Ser Leu Phe Gly Tyr Asp Gln Gly Leu Met Ala Gly Leu Ile
        35                  40                  45

Ser Ala Glu Gln Phe Asn Trp Glu Phe Pro Ala Thr Lys Asp Asn Ser
    50                  55                  60

Val Ile Gln Gly Ala Val Thr Ala Ser Tyr Glu Leu Gly Cys Phe Phe
65                  70                  75                  80

Gly Ala Ile Phe Ala Leu Leu Arg Gly Asp Ala Leu Gly Arg Lys Pro
                85                  90                  95

Ile Ile Phe Phe Gly Ala Thr Ile Ile Leu Gly Thr Ile Ile Ser
            100                 105                 110

Val Thr Pro Phe Arg Pro His Trp Pro Leu Gly Gln Phe Val Val Gly
        115                 120                 125

Arg Val Ile Thr Gly Ile Gly Asn Gly Met Asn Thr Ala Thr Ile Pro
130                 135                 140

Val Trp Gln Ser Glu Met Ser Lys Pro Glu Asn Arg Gly Lys Leu Val
145                 150                 155                 160

Asn Leu Glu Gly Ala Val Val Ala Phe Gly Thr Phe Ile Ala Tyr Trp
                165                 170                 175

Leu Asp Phe Gly Leu Ser Tyr Val Asp Ser Ser Val Ser Trp Arg Phe
            180                 185                 190

Pro Val Ala Phe Gln Ile Phe Phe Ala Leu Trp Val Ile Phe Gly Ile
        195                 200                 205

Ile Gln Leu Pro Glu Ser Pro Arg Trp Leu Ile Ser Lys Asp Arg Lys
    210                 215                 220

Pro Glu Ala Phe Glu Val Leu Ala Ala Leu Asn Asp Thr Thr Pro Asp
225                 230                 235                 240

Asp Asp Ala Ile Val Ala Glu Ala Ser Val Ile Ile Asp Ala Val Arg
                245                 250                 255

Arg Asn Ala Lys Val Gln Ala Gly Phe Lys Asp Leu Phe Thr Gly Gly
            260                 265                 270

Lys Thr Ala His Phe Gln Arg Met Leu Ile Gly Ser Ser Thr Gln Phe
        275                 280                 285

Phe Gln Gln Phe Thr Gly Cys Asn Ala Ala Ile Tyr Tyr Ser Thr Leu
    290                 295                 300

Leu Phe Tyr Glu Thr Val Phe His His Thr Lys Tyr Arg Leu Ser Met
305                 310                 315                 320

Ile Leu Gly Gly Val Phe Ala Thr Ile Tyr Ala Leu Ala Thr Leu Pro
```

```
                        325                 330                 335
Ser Phe Phe Leu Ile Asp Thr Leu Gly Arg Arg Asn Leu Phe Leu Ile
            340                 345                 350

Gly Ala Ile Gly Gln Gly Ile Ser Phe Leu Ile Ser Phe Ala Cys Leu
        355                 360                 365

Ile Asn Pro Thr Glu Gln Asn Ala Lys Gly Ala Ala Val Gly Ile Tyr
    370                 375                 380

Leu Phe Ile Val Phe Phe Ala Phe Thr Ile Leu Pro Leu Pro Trp Ile
385                 390                 395                 400

Tyr Pro Pro Glu Ile Asn Pro Leu Arg Thr Arg Thr Thr Ala Ser Ala
                405                 410                 415

Val Ser Thr Cys Thr Asn Trp Leu Thr Asn Phe Ala Val Val Met Phe
            420                 425                 430

Thr Pro Pro Phe Ile Ser Ala Ser Gly Trp Gly Cys Tyr Leu Tyr Phe
        435                 440                 445

Ala Val Met Asn Phe Leu Phe Val Pro Ile Ile Phe Phe Tyr Pro
    450                 455                 460

Glu Thr Ala Gly Arg Ser Leu Glu Glu Ile Asp Ile Ile Phe Ala Lys
465                 470                 475                 480

Ala Tyr Val Glu Lys Arg Gln Pro Trp Arg Val Ala Ala Thr Leu Pro
                485                 490                 495

Lys Leu Ser Leu Gln Glu Val Glu Asp Glu Ser Lys Ser Leu Gly Leu
            500                 505                 510

Tyr Asp Asp Asp Phe Glu Lys Asp Asn Phe Glu Thr Lys Glu Asp Ile
        515                 520                 525

Ser Asp Gly Thr Ala Ser Asn Ser Asn Gly Val Phe Glu Lys Pro Glu
    530                 535                 540

Asn Val
545

<210> SEQ ID NO 5
<211> LENGTH: 1713
<212> TYPE: DNA
<213> ORGANISM: Pichia sorbiophila
<220> FEATURE:
<221> NAME/KEY: CDS
<222> LOCATION: (1)..(1713)

<400> SEQUENCE: 5 atg gga ttc gaa ctt tgg gga agg acc aac aca ggt ggt ttg aga ggt      48
Met Gly Phe Glu Leu Trp Gly Arg Thr Asn Thr Gly Gly Leu Arg Gly
1               5                   10                  15 aga cct ctt cgt gtt gcc atc acc gct gtt gca act act ggt ttc tcc     96
Arg Pro Leu Arg Val Ala Ile Thr Ala Val Ala Thr Thr Gly Phe Ser
                20                  25                  30 ctt ttc ggt tat gat cag ggt ttg atg tct ggt att att acc ggt act    144
Leu Phe Gly Tyr Asp Gln Gly Leu Met Ser Gly Ile Ile Thr Gly Thr
            35                  40                  45 gaa ttt aac gag gag ttc cct cca acc tgg tcc aag cca cat tac aac    192
Glu Phe Asn Glu Glu Phe Pro Pro Thr Trp Ser Lys Pro His Tyr Asn
        50                  55                  60 gcg tct gag aag aga cat gct act gtt gtt caa ggt gct gtt aca gct    240
Ala Ser Glu Lys Arg His Ala Thr Val Val Gln Gly Ala Val Thr Ala
65                  70                  75                  80 tgt tac gaa att ggt tgt ttc ttc ggt gct ctt ttt gct ttg gtt aga    288
Cys Tyr Glu Ile Gly Cys Phe Phe Gly Ala Leu Phe Ala Leu Val Arg
                85                  90                  95
```

```
ggt gac agg atc ggt aga cgt cca ctt gtc att gtt ggt gct gtt ctt      336
Gly Asp Arg Ile Gly Arg Arg Pro Leu Val Ile Val Gly Ala Val Leu
            100                 105                 110 atc atc att ggt act gtt att tct act gct gct ttt ggt gaa cac tgg      384
Ile Ile Ile Gly Thr Val Ile Ser Thr Ala Ala Phe Gly Glu His Trp
            115                 120                 125 ggt ttg ggt caa ttc gtt att ggt aga gtt att act ggt att ggt aac      432
Gly Leu Gly Gln Phe Val Ile Gly Arg Val Ile Thr Gly Ile Gly Asn
        130                 135                 140 ggt atg aac aca gca act atc cca gtc tgg caa tct gag atc tct cgt      480
Gly Met Asn Thr Ala Thr Ile Pro Val Trp Gln Ser Glu Ile Ser Arg
145                 150                 155                 160 cca gaa aac aga ggt aag tta gtc aac ttg gaa ggt tca gtc att gcc      528
Pro Glu Asn Arg Gly Lys Leu Val Asn Leu Glu Gly Ser Val Ile Ala
            165                 170                 175 att ggt act ttc gtt gct tac tgg att gat ttc ggt ctc tcc tac gtt      576
Ile Gly Thr Phe Val Ala Tyr Trp Ile Asp Phe Gly Leu Ser Tyr Val
            180                 185                 190 aac agc tct gta caa tgg aga ttc cct gtt gcg ttc caa att gtt ttt      624
Asn Ser Ser Val Gln Trp Arg Phe Pro Val Ala Phe Gln Ile Val Phe
            195                 200                 205 gct gct gga ctt ctt gga ggt att ctt ttc atg ccg gag tct cct aga      672
Ala Ala Gly Leu Leu Gly Gly Ile Leu Phe Met Pro Glu Ser Pro Arg
210                 215                 220 tgg ttg ctc gct cat ggc aag aag gag caa gca cac ata gtc tta ggt      720
Trp Leu Leu Ala His Gly Lys Lys Glu Gln Ala His Ile Val Leu Gly
225                 230                 235                 240 gct ttg aat gat ctc gac cct aat gat gac cat gtc ctt gct gag agt      768
Ala Leu Asn Asp Leu Asp Pro Asn Asp Asp His Val Leu Ala Glu Ser
            245                 250                 255 act gtt att acc gat gct att aac aga ttc tcc agg tct caa ctt ggt      816
Thr Val Ile Thr Asp Ala Ile Asn Arg Phe Ser Arg Ser Gln Leu Gly
            260                 265                 270 ttc aag gaa ctt atg tcc ggt ggt aag aac caa cat ttt gct aga atg      864
Phe Lys Glu Leu Met Ser Gly Gly Lys Asn Gln His Phe Ala Arg Met
            275                 280                 285 gtt att ggt tct tcc act caa ttt ttc caa cag ttc act ggt tgt aat      912
Val Ile Gly Ser Ser Thr Gln Phe Phe Gln Gln Phe Thr Gly Cys Asn
        290                 295                 300 gct gcc att tac tat tca aca gtt ttg ttc gaa gag acc att ttc gtc      960
Ala Ala Ile Tyr Tyr Ser Thr Val Leu Phe Glu Glu Thr Ile Phe Val
305                 310                 315                 320 ggt gac aga aga ttg tct ttg gtt atg ggt ggt gtt ttc gct tcc gta     1008
Gly Asp Arg Arg Leu Ser Leu Val Met Gly Gly Val Phe Ala Ser Val
            325                 330                 335 tac gcc ctt gcc act att cca tct ttc ttc tta gtc gat aag ctt ggt     1056
Tyr Ala Leu Ala Thr Ile Pro Ser Phe Phe Leu Val Asp Lys Leu Gly
            340                 345                 350 aga aga aac ttg ttc ttg att ggt gct act ggt caa gct ttg tct ttc     1104
Arg Arg Asn Leu Phe Leu Ile Gly Ala Thr Gly Gln Ala Leu Ser Phe
            355                 360                 365 acc att aca ttt gct tgt ttg atc aac cca aca aag caa aat gct aag     1152
Thr Ile Thr Phe Ala Cys Leu Ile Asn Pro Thr Lys Gln Asn Ala Lys
        370                 375                 380 ggt gca gct gtt ggt atc ttc ttg ttt atc acc ttc ttc gcc ttt aca     1200
Gly Ala Ala Val Gly Ile Phe Leu Phe Ile Thr Phe Phe Ala Phe Thr
385                 390                 395                 400 att ttg cca ttg cct tgg att tac cca cca gaa atc aac cca ttg aga     1248
Ile Leu Pro Leu Pro Trp Ile Tyr Pro Pro Glu Ile Asn Pro Leu Arg
            405                 410                 415
```

```
aca aga act gtt gcc tct gcc gtt tct aca tgt acc aat tgg ctt aca   1296
Thr Arg Thr Val Ala Ser Ala Val Ser Thr Cys Thr Asn Trp Leu Thr
        420                 425                 430 aac ttt gcc gtc gtt atg ttt act cct att ttc att aac gat gct caa   1344
Asn Phe Ala Val Val Met Phe Thr Pro Ile Phe Ile Asn Asp Ala Gln
        435                 440                 445 tgg ggt tgt tac ttg ttc ttt gct tgt ttg aac tac gct ttc att cca   1392
Trp Gly Cys Tyr Leu Phe Phe Ala Cys Leu Asn Tyr Ala Phe Ile Pro
    450                 455                 460 gtt atc ttc tgg ttc tac cca gaa act gct ggc cgt tcc ttg gaa gaa   1440
Val Ile Phe Trp Phe Tyr Pro Glu Thr Ala Gly Arg Ser Leu Glu Glu
465                 470                 475                 480 att gat atc att ttc gcg aag gct tac act gat gga aga cct cca tgg   1488
Ile Asp Ile Ile Phe Ala Lys Ala Tyr Thr Asp Gly Arg Pro Pro Trp
                485                 490                 495 aga gtt gct gct acc atg cca cac ttg tct ttg aag gaa caa gag gag   1536
Arg Val Ala Ala Thr Met Pro His Leu Ser Leu Lys Glu Gln Glu Glu
                500                 505                 510 caa ggt atg caa ctc gga ctt tat gac aat gaa gct gag aaa cag aag   1584
Gln Gly Met Gln Leu Gly Leu Tyr Asp Asn Glu Ala Glu Lys Gln Lys
            515                 520                 525 ttc gag caa acc gag aac ttg atg tct tct agc tct tct gcg aag ctt   1632
Phe Glu Gln Thr Glu Asn Leu Met Ser Ser Ser Ser Ala Lys Leu
        530                 535                 540 cct gaa gag gga tct aac gta aac gag aat gag aac gaa aac acg aac   1680
Pro Glu Glu Gly Ser Asn Val Asn Glu Asn Glu Asn Glu Asn Thr Asn
545                 550                 555                 560 gaa aag gat caa aca cca aag cca act gat gtt                       1713
Glu Lys Asp Gln Thr Pro Lys Pro Thr Asp Val
                565                 570

<210> SEQ ID NO 6
<211> LENGTH: 571
<212> TYPE: PRT
<213> ORGANISM: Pichia sorbiophila

<400> SEQUENCE: 6

Met Gly Phe Glu Leu Trp Gly Arg Thr Asn Thr Gly Gly Leu Arg Gly
1               5                   10                  15

Arg Pro Leu Arg Val Ala Ile Thr Ala Val Ala Thr Thr Gly Phe Ser
            20                  25                  30

Leu Phe Gly Tyr Asp Gln Gly Leu Met Ser Gly Ile Ile Thr Gly Thr
        35                  40                  45

Glu Phe Asn Glu Glu Phe Pro Pro Thr Trp Ser Lys Pro His Tyr Asn
    50                  55                  60

Ala Ser Glu Lys Arg His Ala Thr Val Val Gln Gly Ala Val Thr Ala
65                  70                  75                  80

Cys Tyr Glu Ile Gly Cys Phe Gly Ala Leu Phe Ala Leu Val Arg
                85                  90                  95

Gly Asp Arg Ile Gly Arg Arg Pro Leu Val Ile Val Gly Ala Val Leu
            100                 105                 110

Ile Ile Ile Gly Thr Val Ile Ser Thr Ala Ala Phe Gly Glu His Trp
        115                 120                 125

Gly Leu Gly Gln Phe Val Ile Gly Arg Val Ile Thr Gly Ile Gly Asn
    130                 135                 140

Gly Met Asn Thr Ala Thr Ile Pro Val Trp Gln Ser Glu Ile Ser Arg
145                 150                 155                 160
```

```
Pro Glu Asn Arg Gly Lys Leu Val Asn Leu Glu Ser Val Ile Ala
            165                 170                 175

Ile Gly Thr Phe Val Ala Tyr Trp Ile Asp Phe Gly Leu Ser Tyr Val
        180                 185                 190

Asn Ser Ser Val Gln Trp Arg Phe Pro Val Ala Phe Gln Ile Val Phe
            195                 200                 205

Ala Ala Gly Leu Leu Gly Gly Ile Leu Phe Met Pro Glu Ser Pro Arg
210                 215                 220

Trp Leu Leu Ala His Gly Lys Lys Glu Gln Ala His Ile Val Leu Gly
225                 230                 235                 240

Ala Leu Asn Asp Leu Asp Pro Asn Asp Asp His Val Leu Ala Glu Ser
            245                 250                 255

Thr Val Ile Thr Asp Ala Ile Asn Arg Phe Ser Arg Ser Gln Leu Gly
            260                 265                 270

Phe Lys Glu Leu Met Ser Gly Gly Lys Asn Gln His Phe Ala Arg Met
        275                 280                 285

Val Ile Gly Ser Ser Thr Gln Phe Phe Gln Gln Phe Thr Gly Cys Asn
    290                 295                 300

Ala Ala Ile Tyr Tyr Ser Thr Val Leu Phe Glu Glu Thr Ile Phe Val
305                 310                 315                 320

Gly Asp Arg Arg Leu Ser Leu Val Met Gly Gly Val Phe Ala Ser Val
            325                 330                 335

Tyr Ala Leu Ala Thr Ile Pro Ser Phe Phe Leu Val Asp Lys Leu Gly
            340                 345                 350

Arg Arg Asn Leu Phe Leu Ile Gly Ala Thr Gly Gln Ala Leu Ser Phe
        355                 360                 365

Thr Ile Thr Phe Ala Cys Leu Ile Asn Pro Thr Lys Gln Asn Ala Lys
    370                 375                 380

Gly Ala Ala Val Gly Ile Phe Leu Phe Ile Thr Phe Phe Ala Phe Thr
385                 390                 395                 400

Ile Leu Pro Leu Pro Trp Ile Tyr Pro Pro Glu Ile Asn Pro Leu Arg
            405                 410                 415

Thr Arg Thr Arg Val Ala Ser Ala Val Ser Thr Cys Thr Asn Trp Leu Thr
            420                 425                 430

Asn Phe Ala Val Val Met Phe Thr Pro Ile Phe Ile Asn Asp Ala Gln
        435                 440                 445

Trp Gly Cys Tyr Leu Phe Phe Ala Cys Leu Asn Tyr Ala Phe Ile Pro
    450                 455                 460

Val Ile Phe Trp Phe Tyr Pro Glu Thr Ala Gly Arg Ser Leu Glu Glu
465                 470                 475                 480

Ile Asp Ile Ile Phe Ala Lys Ala Tyr Thr Asp Gly Arg Pro Pro Trp
            485                 490                 495

Arg Val Ala Ala Thr Met Pro His Leu Ser Leu Lys Glu Gln Glu Glu
            500                 505                 510

Gln Gly Met Gln Leu Gly Leu Tyr Asp Asn Glu Ala Glu Lys Gln Lys
        515                 520                 525

Phe Glu Gln Thr Glu Asn Leu Met Ser Ser Ser Ser Ala Lys Leu
    530                 535                 540

Pro Glu Glu Gly Ser Asn Val Asn Glu Asn Glu Asn Thr Asn
545                 550                 555                 560

Glu Lys Asp Gln Thr Pro Lys Pro Thr Asp Val
            565                 570
```

<210> SEQ ID NO 7
<211> LENGTH: 1710
<212> TYPE: DNA
<213> ORGANISM: Saccharomyces paradoxus
<220> FEATURE:
<221> NAME/KEY: CDS
<222> LOCATION: (1)..(1710)

<400> SEQUENCE: 7

| | | | | | | | | | | | | | | | | |
|---|---|---|---|---|---|---|---|---|---|---|---|---|---|---|---|---|
| atg | aag | gac | tcc | aag | ttg | tct | aag | ttc | aag | ggt | aga | ttc | atg | tcc | aga | 48 |
| Met | Lys | Asp | Ser | Lys | Leu | Ser | Lys | Phe | Lys | Gly | Arg | Phe | Met | Ser | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| act | tct | cat | tgg | ggt | ttg | act | ggt | caa | aag | ttg | aga | tac | ttc | att | acc | 96 |
| Thr | Ser | His | Trp | Gly | Leu | Thr | Gly | Gln | Lys | Leu | Arg | Tyr | Phe | Ile | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| att | gct | tct | atg | acc | ggt | ttc | tct | ttg | ttt | ggt | tat | gac | caa | ggt | ttg | 144 |
| Ile | Ala | Ser | Met | Thr | Gly | Phe | Ser | Leu | Phe | Gly | Tyr | Asp | Gln | Gly | Leu | |
| | 35 | | | | | 40 | | | | | 45 | | | | | |

| | | | | | | | | | | | | | | | | |
|---|---|---|---|---|---|---|---|---|---|---|---|---|---|---|---|---|
| atg | gcc | tct | ttg | att | act | ggt | aag | caa | ttc | aac | tac | gaa | ttc | cca | gct | 192 |
| Met | Ala | Ser | Leu | Ile | Thr | Gly | Lys | Gln | Phe | Asn | Tyr | Glu | Phe | Pro | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| acc | aaa | gaa | aac | ggt | gat | cat | gat | aga | cat | gct | acc | gtt | gtt | caa | ggt | 240 |
| Thr | Lys | Glu | Asn | Gly | Asp | His | Asp | Arg | His | Ala | Thr | Val | Val | Gln | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gct | act | act | tct | tgt | tat | gaa | ttg | ggt | tgt | ttc | gcc | ggt | tct | ttg | ttc | 288 |
| Ala | Thr | Thr | Ser | Cys | Tyr | Glu | Leu | Gly | Cys | Phe | Ala | Gly | Ser | Leu | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| gtt | atg | ttt | tac | ggt | gaa | aga | atc | ggt | aga | aag | cca | ttg | att | ttg | atg | 336 |
| Val | Met | Phe | Tyr | Gly | Glu | Arg | Ile | Gly | Arg | Lys | Pro | Leu | Ile | Leu | Met | |
| | | | 100 | | | | | 105 | | | | | 110 | | | |

| | | | | | | | | | | | | | | | | |
|---|---|---|---|---|---|---|---|---|---|---|---|---|---|---|---|---|
| ggt | tcc | att | atc | acc | att | atc | ggt | gct | gtt | att | tct | acc | tgt | gct | ttc | 384 |
| Gly | Ser | Ile | Ile | Thr | Ile | Ile | Gly | Ala | Val | Ile | Ser | Thr | Cys | Ala | Phe | |
| | | 115 | | | | | 120 | | | | | 125 | | | | |

| | | | | | | | | | | | | | | | | |
|---|---|---|---|---|---|---|---|---|---|---|---|---|---|---|---|---|
| aga | gat | tat | tgg | gct | ttg | ggt | caa | ttc | atc | gtt | ggt | aga | gtt | gtt | act | 432 |
| Arg | Asp | Tyr | Trp | Ala | Leu | Gly | Gln | Phe | Ile | Val | Gly | Arg | Val | Val | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| ggt | gtt | ggt | act | ggt | ttg | aac | act | tct | act | att | cca | gtt | tgg | caa | tcc | 480 |
| Gly | Val | Gly | Thr | Gly | Leu | Asn | Thr | Ser | Thr | Ile | Pro | Val | Trp | Gln | Ser | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gaa | atg | tct | aag | gct | gaa | aac | aga | ggt | ttg | ttg | gtt | aac | ttg | gaa | ggt | 528 |
| Glu | Met | Ser | Lys | Ala | Glu | Asn | Arg | Gly | Leu | Leu | Val | Asn | Leu | Glu | Gly | |
| | | | 165 | | | | | 170 | | | | | 175 | | | |

| | | | | | | | | | | | | | | | | |
|---|---|---|---|---|---|---|---|---|---|---|---|---|---|---|---|---|
| tcc | act | att | gct | ttc | ggt | act | atg | att | gct | tac | tgg | atc | gat | ttc | ggt | 576 |
| Ser | Thr | Ile | Ala | Phe | Gly | Thr | Met | Ile | Ala | Tyr | Trp | Ile | Asp | Phe | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| ttt | tcc | tac | act | aac | tct | tcc | gtt | caa | tgg | aga | ttt | cca | gtc | tct | atg | 624 |
| Phe | Ser | Tyr | Thr | Asn | Ser | Ser | Val | Gln | Trp | Arg | Phe | Pro | Val | Ser | Met | |
| | | 195 | | | | | 200 | | | | | 205 | | | | |

| | | | | | | | | | | | | | | | | |
|---|---|---|---|---|---|---|---|---|---|---|---|---|---|---|---|---|
| caa | atc | gtt | ttc | gcc | ttg | ttt | ttg | ttg | gcc | ttc | atg | att | aag | ttg | cca | 672 |
| Gln | Ile | Val | Phe | Ala | Leu | Phe | Leu | Leu | Ala | Phe | Met | Ile | Lys | Leu | Pro | |
| | 210 | | | | | 215 | | | | | 220 | | | | | |

| | | | | | | | | | | | | | | | | |
|---|---|---|---|---|---|---|---|---|---|---|---|---|---|---|---|---|
| gaa | tct | cca | aga | tgg | ttg | atc | tct | caa | tct | aga | act | gaa | gaa | gcc | aga | 720 |
| Glu | Ser | Pro | Arg | Trp | Leu | Ile | Ser | Gln | Ser | Arg | Thr | Glu | Glu | Ala | Arg | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| tac | ttg | gtt | ggt | act | ttg | gat | gat | act | gat | cca | aac | gat | gaa | gaa | gtt | 768 |
| Tyr | Leu | Val | Gly | Thr | Leu | Asp | Asp | Thr | Asp | Pro | Asn | Asp | Glu | Glu | Val | |
| | | | 245 | | | | | 250 | | | | | 255 | | | |

| | | | | | | | | | | | | | | | | |
|---|---|---|---|---|---|---|---|---|---|---|---|---|---|---|---|---|
| att | acc | gaa | gtt | gcc | atg | ttg | cat | gat | gcc | gtt | aat | aga | act | aag | cac | 816 |
| Ile | Thr | Glu | Val | Ala | Met | Leu | His | Asp | Ala | Val | Asn | Arg | Thr | Lys | His | |
| | | | 260 | | | | | 265 | | | | | 270 | | | |

| | | | | | | | | | | | | | | | | |
|---|---|---|---|---|---|---|---|---|---|---|---|---|---|---|---|---|
| gaa | aag | cac | tca | ttg | tca | tcc | ttg | ttt | tct | aga | ggt | aag | tcc | caa | aac | 864 |

```
Glu Lys His Ser Leu Ser Ser Leu Phe Ser Arg Gly Lys Ser Gln Asn
            275                 280                 285 ttg caa aga gct ttg att gct gct tct acc caa ttc ttc caa caa ttc    912
Leu Gln Arg Ala Leu Ile Ala Ala Ser Thr Gln Phe Phe Gln Gln Phe
        290                 295                 300 act ggt tgt aat gct gcc atc tac tac tct act gtt ttg ttc aac aag    960
Thr Gly Cys Asn Ala Ala Ile Tyr Tyr Ser Thr Val Leu Phe Asn Lys
305                 310                 315                 320 acc atc aag ttg gac cac aga ttg tcc atg att att ggt ggt gtt ttc   1008
Thr Ile Lys Leu Asp His Arg Leu Ser Met Ile Ile Gly Gly Val Phe
                325                 330                 335 gct act atc tac gcc ttg tct act att ggt tcc ttc ttc ttg atc gaa   1056
Ala Thr Ile Tyr Ala Leu Ser Thr Ile Gly Ser Phe Phe Leu Ile Glu
        340                 345                 350 aaa tta ggt aga aga aag ttg ttc ttg ttg ggt gct act ggt caa gct   1104
Lys Leu Gly Arg Arg Lys Leu Phe Leu Leu Gly Ala Thr Gly Gln Ala
            355                 360                 365 gtt tct ttc act att acc ttt gct tgc ttg gta aaa gaa aac aaa gaa   1152
Val Ser Phe Thr Ile Thr Phe Ala Cys Leu Val Lys Glu Asn Lys Glu
370                 375                 380 aat gct aga ggt gct gcc gtt ggt ttg ttc tta ttc att act ttc ttc   1200
Asn Ala Arg Gly Ala Ala Val Gly Leu Phe Leu Phe Ile Thr Phe Phe
385                 390                 395                 400 ggt ttg tcc ttg ttg tct ttg cca tgg atc tat cca cca gaa att gct   1248
Gly Leu Ser Leu Leu Ser Leu Pro Trp Ile Tyr Pro Pro Glu Ile Ala
            405                 410                 415 tca atg aag gtt aga gca tct acc aat gct ttc tct act tgt aca aac   1296
Ser Met Lys Val Arg Ala Ser Thr Asn Ala Phe Ser Thr Cys Thr Asn
        420                 425                 430 tgg ttg tgc aat ttc gcc gtt gtt atg ttc acc cca att ttc att ggt   1344
Trp Leu Cys Asn Phe Ala Val Val Met Phe Thr Pro Ile Phe Ile Gly
            435                 440                 445 caa tct ggt tgg ggt tgt tac ttg ttt ttt gcc gtt atg aac tac ttg   1392
Gln Ser Gly Trp Gly Cys Tyr Leu Phe Phe Ala Val Met Asn Tyr Leu
        450                 455                 460 tat atc cca gtt ata ttc ttt ttc tac cct gaa acc gct ggt aga tcc   1440
Tyr Ile Pro Val Ile Phe Phe Phe Tyr Pro Glu Thr Ala Gly Arg Ser
465                 470                 475                 480 ttg gaa gaa att gat att atc ttc gcc aag gcc tac gaa gat ggt act   1488
Leu Glu Glu Ile Asp Ile Ile Phe Ala Lys Ala Tyr Glu Asp Gly Thr
            485                 490                 495 caa cct tgg aga gtt gct aat cat ttg cca aag ttg tcc ttg caa gaa   1536
Gln Pro Trp Arg Val Ala Asn His Leu Pro Lys Leu Ser Leu Gln Glu
        500                 505                 510 gtt gaa gat cac gct aat gct ttg ggt tct tat gat gac gaa atg gaa   1584
Val Glu Asp His Ala Asn Ala Leu Gly Ser Tyr Asp Asp Glu Met Glu
            515                 520                 525 aag gat gat ttc gcc gaa gat aga gtc gaa gat acc tac aat caa atc   1632
Lys Asp Asp Phe Ala Glu Asp Arg Val Glu Asp Thr Tyr Asn Gln Ile
530                 535                 540 aac ggt gac aac tcc tct tcc tcc tct aat atc aaa aac gaa gat act   1680
Asn Gly Asp Asn Ser Ser Ser Ser Ser Asn Ile Lys Asn Glu Asp Thr
545                 550                 555                 560 gtt aac gac aag gcc aac tct gaa tct tga                           1710
Val Asn Asp Lys Ala Asn Ser Glu Ser
            565

<210> SEQ ID NO 8
<211> LENGTH: 569
<212> TYPE: PRT
```

<213> ORGANISM: Saccharomyces paradoxus

<400> SEQUENCE: 8

```
Met Lys Asp Ser Lys Leu Ser Lys Phe Lys Gly Arg Phe Met Ser Arg
1               5                   10                  15
Thr Ser His Trp Gly Leu Thr Gly Gln Lys Leu Arg Tyr Phe Ile Thr
            20                  25                  30
Ile Ala Ser Met Thr Gly Phe Ser Leu Phe Gly Tyr Asp Gln Gly Leu
        35                  40                  45
Met Ala Ser Leu Ile Thr Gly Lys Gln Phe Asn Tyr Glu Phe Pro Ala
    50                  55                  60
Thr Lys Glu Asn Gly Asp His Asp Arg His Ala Thr Val Val Gln Gly
65                  70                  75                  80
Ala Thr Thr Ser Cys Tyr Glu Leu Gly Cys Phe Ala Gly Ser Leu Phe
                85                  90                  95
Val Met Phe Tyr Gly Glu Arg Ile Gly Arg Lys Pro Leu Ile Leu Met
            100                 105                 110
Gly Ser Ile Ile Thr Ile Ile Gly Ala Val Ile Ser Thr Cys Ala Phe
        115                 120                 125
Arg Asp Tyr Trp Ala Leu Gly Gln Phe Ile Val Gly Arg Val Val Thr
130                 135                 140
Gly Val Gly Thr Gly Leu Asn Thr Ser Thr Ile Pro Val Trp Gln Ser
145                 150                 155                 160
Glu Met Ser Lys Ala Glu Asn Arg Gly Leu Leu Val Asn Leu Glu Gly
                165                 170                 175
Ser Thr Ile Ala Phe Gly Thr Met Ile Ala Tyr Trp Ile Asp Phe Gly
            180                 185                 190
Phe Ser Tyr Thr Asn Ser Ser Val Gln Trp Arg Phe Pro Val Ser Met
        195                 200                 205
Gln Ile Val Phe Ala Leu Phe Leu Ala Phe Met Ile Lys Leu Pro
    210                 215                 220
Glu Ser Pro Arg Trp Leu Ile Ser Gln Ser Arg Thr Glu Glu Ala Arg
225                 230                 235                 240
Tyr Leu Val Gly Thr Leu Asp Asp Thr Asp Pro Asn Asp Glu Glu Val
                245                 250                 255
Ile Thr Glu Val Ala Met Leu His Asp Ala Val Asn Arg Thr Lys His
            260                 265                 270
Glu Lys His Ser Leu Ser Ser Leu Phe Ser Arg Gly Lys Ser Gln Asn
        275                 280                 285
Leu Gln Arg Ala Leu Ile Ala Ala Ser Thr Gln Phe Gln Gln Phe
    290                 295                 300
Thr Gly Cys Asn Ala Ala Ile Tyr Tyr Ser Thr Val Leu Phe Asn Lys
305                 310                 315                 320
Thr Ile Lys Leu Asp His Arg Leu Ser Met Ile Ile Gly Gly Val Phe
                325                 330                 335
Ala Thr Ile Tyr Ala Leu Ser Thr Ile Gly Ser Phe Phe Leu Ile Glu
            340                 345                 350
Lys Leu Gly Arg Arg Lys Leu Phe Leu Leu Gly Ala Thr Gly Gln Ala
        355                 360                 365
Val Ser Phe Thr Ile Thr Phe Ala Cys Leu Val Lys Glu Asn Lys Glu
    370                 375                 380
Asn Ala Arg Gly Ala Ala Val Gly Leu Phe Leu Phe Ile Thr Phe Phe
385                 390                 395                 400
```

-continued

```
Gly Leu Ser Leu Leu Ser Leu Pro Trp Ile Tyr Pro Glu Ile Ala
            405                 410                 415

Ser Met Lys Val Arg Ala Ser Thr Asn Ala Phe Ser Cys Thr Asn
        420                 425                 430

Trp Leu Cys Asn Phe Ala Val Val Met Phe Thr Pro Ile Phe Ile Gly
        435                 440                 445

Gln Ser Gly Trp Gly Cys Tyr Leu Phe Phe Ala Val Met Asn Tyr Leu
    450                 455                 460

Tyr Ile Pro Val Ile Phe Phe Tyr Pro Glu Thr Ala Gly Arg Ser
465                 470                 475                 480

Leu Glu Glu Ile Asp Ile Ile Phe Ala Lys Ala Tyr Glu Asp Gly Thr
                485                 490                 495

Gln Pro Trp Arg Val Ala Asn His Leu Pro Lys Leu Ser Leu Gln Glu
            500                 505                 510

Val Glu Asp His Ala Asn Ala Leu Gly Ser Tyr Asp Glu Met Glu
                515                 520                 525

Lys Asp Asp Phe Ala Glu Asp Arg Val Glu Asp Thr Tyr Asn Gln Ile
        530                 535                 540

Asn Gly Asp Asn Ser Ser Ser Ser Asn Ile Lys Asn Glu Asp Thr
545                 550                 555                 560

Val Asn Asp Lys Ala Asn Ser Glu Ser
                565
```

<210> SEQ ID NO 9
<211> LENGTH: 515
<212> TYPE: PRT
<213> ORGANISM: Saccharomycopsis fibuligera

<400> SEQUENCE: 9

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205
```

```
Ala Ser Asp Ile Tyr Trp Lys Ile Ile Lys Pro Asp Leu Gln His Val
    210                 215                 220
Ser Thr His Trp Ser Thr Ser Gly Phe Asp Leu Trp Glu Glu Asn Gln
225                 230                 235                 240
Gly Thr His Phe Phe Thr Ala Leu Val Gln Leu Lys Ala Leu Ser Tyr
                245                 250                 255
Gly Ile Pro Leu Ser Lys Thr Tyr Asn Asp Pro Gly Phe Thr Ser Trp
            260                 265                 270
Leu Glu Lys Gln Lys Asp Ala Leu Asn Ser Tyr Ile Asn Ser Ser Gly
        275                 280                 285
Phe Val Asn Ser Gly Lys Lys His Ile Val Glu Ser Pro Gln Leu Ser
    290                 295                 300
Ser Arg Gly Gly Leu Asp Ser Ala Thr Tyr Ile Ala Ala Leu Ile Thr
305                 310                 315                 320
His Asp Ile Gly Asp Asp Thr Tyr Thr Pro Phe Asn Val Asp Asn
                325                 330                 335
Ser Tyr Val Leu Asn Ser Leu Tyr Tyr Leu Leu Val Asp Asn Lys Asn
                340                 345                 350
Arg Tyr Lys Ile Asn Gly Asn Tyr Lys Ala Gly Ala Ala Val Gly Arg
            355                 360                 365
Tyr Pro Glu Asp Val Tyr Asn Gly Val Gly Thr Ser Glu Gly Asn Pro
    370                 375                 380
Trp Gln Leu Ala Thr Ala Tyr Ala Gly Gln Thr Phe Tyr Thr Leu Ala
385                 390                 395                 400
Tyr Asn Ser Leu Lys Asn Lys Lys Asn Leu Val Ile Glu Lys Leu Asn
                405                 410                 415
Tyr Asp Leu Tyr Asn Ser Phe Ile Ala Asp Leu Ser Lys Ile Asp Ser
            420                 425                 430
Ser Tyr Ala Ser Lys Asp Ser Leu Thr Leu Thr Tyr Gly Ser Asp Asn
            435                 440                 445
Tyr Lys Asn Val Ile Lys Ser Leu Leu Gln Phe Gly Asp Ser Phe Leu
    450                 455                 460
Lys Val Leu Leu Asp His Ile Asp Asp Asn Gly Gln Leu Thr Glu Glu
465                 470                 475                 480
Ile Asn Arg Tyr Thr Gly Phe Gln Ala Gly Ala Val Ser Leu Thr Trp
                485                 490                 495
Ser Ser Gly Ser Leu Leu Ser Ala Asn Arg Ala Arg Asn Lys Leu Ile
            500                 505                 510
Glu Leu Leu
    515
```